(12) United States Patent
Kreft et al.

(10) Patent No.: US 7,691,884 B2
(45) Date of Patent: *Apr. 6, 2010

(54) HETEROCYCLIC SULFONAMIDE INHIBITORS OF β AMYLOID PRODUCTION

(75) Inventors: Anthony Frank Kreft, Langhorne, PA (US); Derek C. Cole, New City, NY (US); Kevin R. Woller, Ayer, MA (US); Joseph R. Stock, Monroe, NY (US); George Diamantidis, Randolph, NJ (US); Dennis M. Kubrak, Philadelphia, PA (US); Kristina M. Kutterer, Westwood, NJ (US); William J. Moore, Collegeville, PA (US); David S. Casebier, Carlisle, MA (US)

(73) Assignees: Wyeth, Madison, NJ (US); ArQule, Inc., Woburn, MA (US)

(*) Notice: Subject to any disclaimer, the term of this patent is extended or adjusted under 35 U.S.C. 154(b) by 258 days.

This patent is subject to a terminal disclaimer.

(21) Appl. No.: 11/081,784

(22) Filed: Mar. 16, 2005

(65) Prior Publication Data

US 2005/0196813 A1    Sep. 8, 2005

Related U.S. Application Data

(63) Continuation of application No. 10/455,674, filed on Jun. 5, 2003, now Pat. No. 6,878,742, which is a continuation of application No. 10/014,304, filed on Dec. 11, 2001, now Pat. No. 6,610,734.

(60) Provisional application No. 60/255,105, filed on Dec. 13, 2000.

(51) Int. Cl.
| | |
|---|---|
| *A61K 31/44* | (2006.01) |
| *A61K 31/38* | (2006.01) |
| *A61K 31/335* | (2006.01) |
| *A61K 31/34* | (2006.01) |
| *C07D 409/12* | (2006.01) |
| *C07D 333/34* | (2006.01) |
| *C07D 407/12* | (2006.01) |
| *C07D 307/34* | (2006.01) |

(52) U.S. Cl. ............ 514/336; 514/445; 514/452; 514/461; 546/280.4; 549/65; 549/370; 549/505

(58) Field of Classification Search ............ 549/65, 549/370, 505; 514/336, 445, 452, 461; 546/280.4
See application file for complete search history.

(56) References Cited

U.S. PATENT DOCUMENTS

| | | | |
|---|---|---|---|
| 5,464,853 A | 11/1995 | Chan et al. | |
| 5,506,243 A | 4/1996 | Ando et al. | |
| 5,514,691 A | 5/1996 | Chan et al. | |
| 5,561,146 A | 10/1996 | Kim et al. | |
| 5,571,821 A | 11/1996 | Chan et al. | |
| 5,591,761 A | 1/1997 | Chan et al. | |
| 5,593,846 A | 1/1997 | Schenk | |
| 5,594,021 A | 1/1997 | Chan et al. | |
| 5,624,937 A | 4/1997 | Reel | |
| 5,703,129 A | 12/1997 | Felsenstein | |
| 5,710,153 A | 1/1998 | Ohmoto et al. | |
| 5,852,007 A | 12/1998 | Chatterjee | |
| 5,877,193 A | 3/1999 | Cesura et al. | |
| 5,981,168 A | 11/1999 | Reiner | |
| 6,248,775 B1 | 6/2001 | Vazquez | |
| 6,342,610 B2 | 1/2002 | Chan et al. | |
| 6,376,523 B1 | 4/2002 | Chan et al. | |
| 6,566,536 B2 | 5/2003 | Muller et al. | |
| 6,610,734 B2 * | 8/2003 | Kreft et al. | 514/445 |
| 6,657,070 B2 | 12/2003 | Resnick | |
| 6,878,742 B2 | 4/2005 | Kreft et al. | |
| 2004/0006050 A1 | 1/2004 | Kreft et al. | |
| 2004/0198778 A1 | 10/2004 | Kreft et al. | |

FOREIGN PATENT DOCUMENTS

| | | |
|---|---|---|
| EP | 510700 A2 | 10/1992 |
| EP | 0 652 009 | 5/1995 |
| EP | 652009 | 5/1995 |
| EP | 1172361 A1 | 12/1999 |
| EP | 1088821 A1 | 4/2001 |
| JP | 5-148233 | 6/1993 |
| JP | 07-048340 | 2/1995 |
| JP | 08-053492 | 2/1996 |
| JP | 09-136878 | 5/1997 |
| JP | 09-235276 | 9/1997 |

(Continued)

OTHER PUBLICATIONS

Abstract of Japanese Patent No. JP-11-343279 Jan. 26, 2002.

(Continued)

*Primary Examiner*—Joseph R Kosack
(74) *Attorney, Agent, or Firm*—Scott K. Larsen; Howson & Howson LLP

(57) ABSTRACT

Compounds of Formula (I),

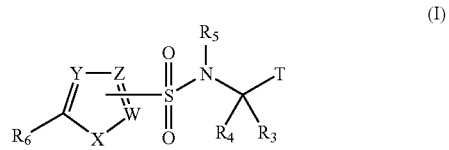

wherein $R_1, R_2, R_3, R_4, R_5, R_6$, T, W, X, Y and Z are as defined herein are provided, together with pharmaceutically acceptable salt, hydrates and/or prodrugs thereof. Methods of using these compounds for determining β-amyloid levels in a subject are described.

16 Claims, No Drawings

FOREIGN PATENT DOCUMENTS

| | | |
|---|---|---|
| JP | 10-067761 | 3/1998 |
| JP | 11-343279 | 1/2002 |
| WO | WO-95/29904 A1 | 11/1995 |
| WO | WO 97/21690 | 6/1997 |
| WO | WO 97/24340 | 7/1997 |
| WO | WO-98/03166 A1 | 1/1998 |
| WO | WO 98/16504 | 4/1998 |
| WO | WO-98/22104 A3 | 5/1998 |
| WO | WO-98/22493 | 5/1998 |
| WO | WO-98/22493 A2 | 5/1998 |
| WO | WO 99/28316 | 6/1999 |
| WO | WO 99/62880 | 12/1999 |
| WO | WO-00/09107 A2 | 2/2000 |
| WO | WO-00/50391 A1 | 8/2000 |
| WO | WO-01/23379 A1 | 4/2001 |
| WO | WO-01/27091 A1 | 4/2001 |
| WO | WO-01/27108 A1 | 4/2001 |
| WO | WO-02/057252 A1 | 7/2002 |
| WO | WO-03/050062 A1 | 6/2003 |
| WO | WO-03/050063 A1 | 6/2003 |
| WO | WO-03/103660 A1 | 12/2003 |

OTHER PUBLICATIONS

Augelli-Szafran et al., "β-amyloid as a target for Alzheimer's Disease therapy", *Annual Reports in Medicinal Chemistry* Ch. 3 1999 pp. 21-30.

Dodart et al., "The β-amyloid precursor protein and its derivatives: From biology to learning and memory process", *Reviews in the Neurosciences* 2000 11(2-3):75-93.

Esler et al., "Transition-state analogue inhibitors of β-secretase bind directly to presenilin-1", *Nature Cell Bio.* Jul. 2000 2:428-434.

Findeis et al., "Modified-peptide inhibitors of amyloid β-peptide polymerization", *Biochem.* May 1999 38(21):6791-6800.

Ghosh et al., "Design of potent inhibitors for human brain memapsin 2 (β-secretase)", *J. Am. Chem. Soc.* 2000 122:3522-3523.

Goate, A., "Monogenetic determinants of Alzheimer's Disease: APP mutations", *Cell. Mol. Lift Sci.* Sep. 1998 54:897-901.

Han et al., "Total asymmetric synthesis of highly constrained amino acids isopropyl-2', 6'-dimethyl-tyrosines", *Tetrahedron Letters* 1997 38(29):5135-5138.

John et al., "Chapter 2. Alzheimer's Disease: Recent advances on the amyloid hypothesis", *Ann. Reports Med. Chem.* 1997 32:11-20.

Larner et al., "Review—Central and peripheral nervous systems—Alzheimer's disease: Towards therapeutic manipulation of the amyloid precursor protein and amyloid peptides", *Exp. Opin. Ther. Patents* 1997 7(10):1115-1127.

Li et al., "Photoactivated β-secretase inhibitors directed to the active site covalently label presenilin 1", *Nature* Jun. 2000 405:689-694.

Li et al., "The amyloid precursor protein of Alzheimer's Disease in human brain and blood", *J. of Leuko. Bio.* Oct. 1999 66:567-574.

Moore et al., "Inhibition of β-amyloid formation as a therapeutic strategy", *Exp. Opin. Ther. Patents* 1999 9(2):135-146.

Naslund et al., "Correlation between elevated levels of amyloid β-peptide in the brain and cognitive decline", *JAMA* Mar. 2000 283(12):1571-1577.

Rishton et al., "Fenchylamine sulfonamide inhibitors of amyloid peptide production by the β-secretase proteolytic pathway: potential small-molecule therapeutic agents for the treatment of Alzheimer's Disease", *J. Med. Chem.* Jun. 15, 2000 43(12):2297-2299.

Sabbagh et al., "β-amyloid and treatment opportunities for Alzheimer's Disease", *Alzheimer's Disease Review* 1997 3:1-19.

Sinha et al., "Purification and cloning of amyloid precursor protein β-secretase from human brain", *Nature* Dec. 1999 402:537-540.

Skovronsky et al., "β-secretase revealed: Starting gate for race to novel therapies for Alzheimer's Disease", *TIPS* May 2000 21:161-163.

Small et al., "Alzheimer's Disease and the amyloid protein: What is the role of amyloid?", *J. of Neurochem.* Aug. 1999 73(2):443-449.

Testa et al., "Prodrugs revisited: The "Ad Hoc" approach as a complement to ligan design", *Med. Res.Rev.* May 1996 16(3):233-241.

Wagner et al., "Modulation of amyloid protein precursor processing as a means of retarding progression of Alzheimer's Disease", *J. Clin. Invest.* Nov. 1999 104(10):1329-1332.

Wermuth et al., "Molecular variations based on isosteric replacements", *Prac. Med. Chem.* Feb. 1996 pp. 203-237.

Wolfe et al., "A substrate-based difluoro ketone selectively inhibits Alzheimer's β-secretase activity", *J. Med. Chem.* Jan. 1, 1998 41:6-9.

Mehta, "Techniques in Diagnostic Pathology", vol. 2, Bullock et al., Eds., Academic Press: Boston, MA, pp. 99-112 (1991).

Sugihara et al., English Abstract of JP 09-235276.

Cesura and Rover, English Abstract of JP 10-067761.

Omoto et al., English Abstract of JP 09-136878.

Kim et al., English Abstract of JP 08-053492.

Ando et al., English Abstract of JP 07-048340.

\* cited by examiner

HETEROCYCLIC SULFONAMIDE INHIBITORS OF β AMYLOID PRODUCTION

CROSS-REFERENCE TO RELATED APPLICATIONS

This application is a continuation of U.S. patent application Ser. No. 10/455,674, filed Jun. 5, 2003, which is a continuation of U.S. patent application Ser. No. 10/014,304, filed Dec. 11, 2001, now U.S. Pat. No. 6,610,734, issued Aug. 26, 2003, which claims the benefit of the priority of U.S. Provisional Patent Application No. 60/255,105, filed Dec. 13, 2000.

BACKGROUND OF THE INVENTION

This invention relates to inhibitors of beta amyloid production, which have utility in the treatment of Alzheimer's disease.

Alzheimer's Disease (AD) is the most common form of dementia (loss of memory) in the elderly. The main pathological lesions of AD found in the brain consist of extracellular deposits of beta amyloid protein in the form of plaques and angiopathy and intracellular neurofibrillary tangles of aggregated hyperphosphorylated tau protein. Recent evidence has revealed that elevated beta amyloid levels in brain not only precede tau pathology but also correlate with cognitive decline. Further suggesting a causative role for beta amyloid in AD, recent studies have shown that aggregated beta amyloid is toxic to neurons in cell culture.

Beta amyloid protein is composed mainly of 39-42 amino acid peptides and is produced from a larger precursor protein called amyloid precursor protein (APP) by the sequential action of the proteases beta and gamma secretase. Although rare, cases of early onset AD have been attributed to genetic mutations in APP that lead to an overproduction of either total beta amyloid protein or its more aggregation-prone 42 amino acid isoform. Furthermore, people with Down's Syndrome possess an extra chromosome that contains the gene that encodes APP and thus have elevated beta amyloid levels and invariably develop AD later in life.

There continues to be an unmet need for compositions useful in inhibiting beta amyloid production and in the treatment of the effects of Alzheimer's Disease (AD).

SUMMARY OF THE INVENTION

The present invention provides heterocyclic sulfonamide derivatives of 2-amino-1-alcohols and related homologs that have been found to specifically inhibit the production of beta amyloid protein from APP and to be capable of passing through the blood-brain barrier. These compounds are useful for the treatment of conditions in which beta amyloid levels are elevated (e.g., AD, Down's Syndrome). Systemic administration of these compounds to subjects at risk of, or suffering from, these diseases lowers beta amyloid protein levels with subsequent reduction in the toxic beta amyloid aggregates in the brains of these patients.

In one aspect, the present invention provides a compound of Formula (I), as defined herein, pharmaceutically acceptable salts, hydrates, or prodrugs thereof. In one embodiment, the compounds of Formula (I) are thiophenesulfonamides. In another embodiment, the compounds of Formula (I) are furansulfonamides. Among the particularly desirable compounds are those having a halogen in the 5-position of the heterocycle (e.g., 5-halo thiophenesulfonamides) and β-branches in the side chain of the primary alcohol.

In another aspect, the invention provides a pharmaceutical composition containing one or more compounds of Formula (I) and a physiologically compatible carrier.

In yet another aspect, the invention provides a method of inhibiting beta amyloid production in a subject by delivering a compound of Formula (I).

In still another aspect, the invention provides a method of treating Alzheimer's Disease (AD) in a subject by administering a compound of Formula (I) to the subject in an amount sufficient to alleviate the symptoms or progress of AD.

These and other aspects of the invention will be apparent to one of skill in the art upon reading of the following detailed description of the invention.

DETAILED DESCRIPTION OF THE INVENTION

The invention consists of compounds of Formula (I), their pharmaceutical formulations, and their use in modulating beta amyloid production in subjects at risk for, or suffering from, AD or other diseases resulting from elevated levels of beta amyloid protein in the brain. The compounds of Formula (I) include pharmaceutically acceptable salts and/or hydrates or prodrugs thereof, wherein:

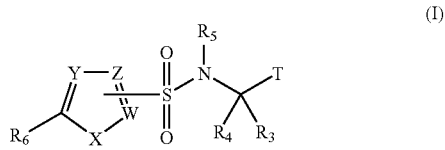

(I)

$R_1$ and $R_2$ are independently selected from the group consisting of hydrogen, alkyl, substituted alkyl, $CF_3$, alkenyl, substituted alkenyl, alkynyl, substituted alkynyl, cycloalkyl, substituted cycloalkyl, phenyl, substituted phenyl, and $(CH_2)_n(1,3)$dioxane, where n is 2 to 5;

$R_3$ is selected from the group consisting of hydrogen, alkyl, and substituted alkyl;

$R_4$ is selected from the group consisting of hydrogen, alkyl, substituted alkyl, alkylcycloalkyl, substituted alkylcycloalkyl, phenyl(substituted)alkyl, alkylOH, substituted alkylOH, alkylOBn, substituted alkylOBn, alkylpyridyl, substituted alkylpyridyl, alkylfuranyl, substituted alkylfuranyl, CH(OH)phenyl, CH(OH)substituted phenyl, alkenyl, substituted alkenyl, cycloalkyl, substituted cycloalkyl, N-substituted-piperidinyl, piperidinyl, substituted piperidinyl, tetrahydrothiopyran, substituted tetrahydrothiopyran, 2-indane, substituted 2-indane, phenyl, substituted phenyl, alkylNHR$_7$, and substituted alkylNHR$_7$;

with the proviso that $R_3$ and $R_4$ are not both hydrogen;

$R_7$ is alkyl, substituted alkyl, cycloalkyl, substituted cycloalkyl, benzyl, substituted benzyl, alkylOH, substituted alkylOH, alkylSR$_8$, or substituted alkylSR$_8$;

$R_8$ is alkyl, substituted alkyl, benzyl, or substituted benzyl; or $R_3$ and $R_4$ may be joined to form a ring;

$R_5$ is selected from the group consisting of hydrogen, lower alkyl, substituted lower alkyl, alkenyl, substituted alkenyl, alkynyl, substituted alkynyl, $CH_2$cycloalkyl, substituted $CH_2$cycloalkyl, benzyl, substituted benzyl, and $CH_2CH_2QR_9$;

Q is O, NH or S;

$R_9$ is lower alkyl, substituted lower alkyl, phenyl, or substituted phenyl;

$R_6$ is selected from the group consisting of hydrogen, halogen and $CF_3$;

T is selected from the group consisting of

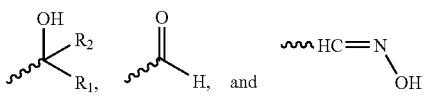

W, Y and Z are independently selected from the group consisting of C, $CR_{10}$ and N;

$R_{10}$ is selected from the group consisting of hydrogen and halogen, with the proviso that at least one of W, Y and Z must be C;

X is selected from the group consisting of O, S, $SO_2$, and $NR_{11}$;

$R_{11}$ is selected from the group consisting of hydrogen, lower alkyl, substituted lower alkyl, benzyl, substituted benzyl, phenyl, and substituted phenyl;

provided that when the compound contains one or more chiral centers, at least one of the chiral centers must be of S-stereochemistry.

The point of attachment of the W—X—Y—Z—C heterocyclic ring to the $SO_2$ group is not a limitation of the present invention. However, in one preferred embodiment, the ring is attached to the $SO_2$ group through a carbon-atom. However, the ring may be attached through O, S, or N heteroatoms.

The compounds of the invention may contain one or more asymmetric carbon atoms and some of the compounds may contain one or more asymmetric (chiral) centers and may thus give rise to optical isomers and diastereomers. While shown without respect to stereochemistry in Formula (I), when the compounds of Formula (I) contain one or more chiral centers, at least one of the chiral centers is of S-stereochemistry. Most preferably, the carbon atom to which N, T, $R_3$ and $R_4$ are attached is of S-stereochemistry. Thus, the invention includes such optical isomers and disastereomers; as well as the racemic and resolved, enantiomerically pure stereoisomers; as well as other mixtures of the R and S stereoisomers, and pharmaceutically acceptable salts, hydrates, and prodrugs thereof.

The term "alkyl" is used herein to refer to both straight- and branched-chain saturated aliphatic hydrocarbon groups having one to ten carbon atoms, preferably one to eight carbon atoms and, most preferably, one to six carbon atoms; as used herein, the term "lower alkyl" refers to straight- and branched-chain saturated aliphatic hydrocarbon groups having one to six carbon atoms; "alkenyl" is intended to include both straight- and branched-chain alkyl group with at least one carbon-carbon double bond and two to eight carbon atoms, preferably two to six carbon atoms; "alkynyl" group is intended to cover both straight- and branched-chain alkyl groups with at least one carbon-carbon triple bond and two to eight carbon atoms, preferably two to six carbon atoms.

The terms "substituted alkyl", "substituted alkenyl", and "substituted alkynyl" refer to alkyl, alkenyl, and alkynyl as just described having from one to three substituents selected from the group including halogen, CN, OH, $NO_2$, amino, aryl, heterocyclic, substituted aryl, substituted heterocyclic, alkoxy, substituted alkoxy, aryloxy, substituted alkyloxy, alkylcarbonyl, alkylcarboxy, alkylamino, arylthio. These substituents may be attached to any carbon of an alkyl, alkenyl, or alkynyl group provided that the attachment constitutes a stable chemical moiety.

The term "aryl" is used herein to refer to a carbocyclic aromatic system, which may be a single ring, or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, phenanthryl, and indane.

The term "substituted aryl" refers to aryl as just defined having one to four substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The term "substituted benzyl" refers to a benzyl group, having substituted on the benzene ring, one to five substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, isoquinolinyl, and tetrahydrothiopyran.

The term "substituted heterocyclic" is used herein to describe the heterocyclic just defined having one to four substituents selected from the group which includes halogen, CN, OH, $NO_2$, amino, alkyl, substituted alkyl, cycloalkyl, substituted cycloalkyl, alkenyl, substituted alkenyl, alkynyl, substituted alkynyl, alkoxy, substituted alkoxy, aryloxy, substituted aryloxy, alkyloxy, substituted alkyloxy, alkylcarbonyl, substituted alkylcarbonyl, alkylcarboxy, substituted alkylcarboxy, alkylamino, substituted alkylamino, arylthio, or substituted arylthio.

The term "substituted cycloalkyl" is used herein to describe a carbon-based ring having more than 3 carbonatoms which forms a stable ring and having from one to five substituents selected from the group consisting of halogen, CN, OH, $NO_2$, amino, alkyl, substituted alkyl, alkenyl, substituted alkenyl, alkynyl, alkoxy, aryloxy, substituted alkyloxy, alkylcarbonyl, alkylcarboxy, alkylamino, substituted alkylamino, arylthio, heterocyclic, substituted heterocyclic, aminoalkyl, and substituted aminoalkyl.

Where the terms "substituted alkylcycloalkyl", "substituted alkylOBn", "substituted alkylpyridyl", "substituted alkylfuranyl", "substituted alkyl $NHR_7$", "substituted alkylOH", and "substituted alkyl$SR_8$" are recited, the substitution may occur at the alkyl group or on the corresponding base compound.

As used in the definition of the $R_4$ group, an N-substituted piperidinyl group may be defined as are the substituted heterocyclic groups. Among particularly desirable substituents are N-alkyl-, N-aryl-, N-acyl-, and N-sulfonyl piperidinyl groups. One particularly suitable N-acyl-piperidinyl group is N-t-butyloxycarbonyl (BOC)-piperidine. However, other suitable substituents can be readily identified by one of skill in the art.

The term "alkoxy" is used herein to refer to the OR group, where R is alkyl or substituted alkyl. The term "aryloxy" is used herein to refer to the OR group, where R is aryl or substituted aryl. The term "alkylcarbonyl" is used herein to refer to the RCO group, where R is alkyl or substituted alkyl. The term "alkylcarboxy" is used herein to refer to the COOR group, where R is alkyl or substituted alkyl. The term "aminoalkyl" refers to both secondary and tertiary amines wherein the alkyl or substituted alkyl groups, containing one to eight carbon atoms, which may be either same or different and the point of attachment is on the nitrogen atom.

The term "halogen" refers to Cl, Br, F, or I.

The term "ring" structure, e.g., when $R_3$ and $R_4$ may form a ring structure, includes a monocyclic structure, a bridged cyclo structure, and fused cyclo structures, unless the type of ring structure is otherwise specified.

The compounds of the present invention can be used in the form of salts derived from pharmaceutically or physiologically acceptable acids or bases. These salts include, but are not limited to, the following salts with organic and inorganic acids such as acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids, and mixtures thereof. Other salts include salts with alkali metals or alkaline earth metals, such as sodium (e.g., sodium hydroxide), potassium (e.g., potassium hydroxide), calcium or magnesium.

These salts, as well as other compounds of the invention may be in the form of esters, carbamates and other conventional "pro-drug" forms, which, when administered in such form, convert to the active moiety in vivo. In a currently preferred embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

In one particularly desirable embodiment, the compounds of Formula (I) are thiophenesulfonamides, and more desirably, 5-halo thiophenesulfonamides, and most desirably, 5-halo thiophene sulfonamides with β-branches in the side chain of a primary alcohol. Thus, with respect to Formula (I), the compound of the invention desirably has a structure in which X is S, W is C (or $CR_{10}$), Y is C (or $CR_{10}$) and Z is C (or $CR_{10}$), and the sulfonamide is attached to C2 of the thiophene ring. More desirably, X is S, W is C (or $CR_{10}$), Y is C (or $CR_{10}$), Z is C (or $CR_{10}$) and $R_6$ is a halogen. Most desirably, X is S, X is C, W is C, Y is C, Z is C, $R_6$ is a halogen, and T is $C(OH)R_1R_2$, where $R_1$ and $R_2$ are hydrogen, $R_3$ is H, $R_4$ is a lower alkyl of S-stereochemistry, and $R_5$ is H. In preliminary screening assays in vitro and in vivo, compounds of these structures have been found to have unexpectedly good beta-amyloid inhibitory activity, and in many cases, better activity than compounds of Formula (I) having other heterocycles (e.g., furans, where X is O). However, other such compounds of Formula (I) are also useful for the purposes described herein.

For example, in another embodiment, the compounds of Formula (I) are furansulfonamides, in which X is O, W is C, Y is C, and Z is C. In one particularly desirable embodiment, the furansulfonamides of Formula (I) are further characterized by β-branches in the side chain of a primary alcohol. Thus, with respect to Formula (I), in these compounds T is $C(OH)R_1R_2$, in which $R_1$ and $R_2$ are hydrogen, $R_3$ is H, $R_4$ is a lower alkyl of S-stereochemistry, $R_5$ is H and $R_6$ is halogen.

In still another embodiment, the compounds of Formula (I) are characterized by being sulfonamides of Formula (I), which have β-branches in the side chain of the primary alcohol group. Thus, with respect to Formula (I), in these compounds T is $C(OH)R_1R_2$, $R_1$ and $R_2$ are hydrogen, $R_3$ is H, $R_4$ is a lower alkyl of S-stereochemistry, and $R_5$ is H.

These and the other compounds of the invention can be prepared following the Schemes illustrated below.

Synthesis

The compounds of the present invention can be prepared in a number of ways well known to one skilled in the art of organic synthesis. The compounds of the present invention can be prepared using the methods described below, together with synthetic methods known in the synthetic organic arts or variations of these methods by one skilled in the art. (See, generally, *Comprehensive Organic Synthesis*, "Selectivity, Strategy & Efficiency in Modern Organic Chemistry", ed., I. Fleming, Pergamon Press, New York (1991); *Comprehensive Organic Chemistry*, "The Synthesis and Reactions of Organic Compounds", ed. J. F. Stoddard, Pergamon Press, New York (1979)). Preferred methods include, but are not limited to, those outlined below.

A first method of preparation consists of reaction of a 2-aminoalcohol II with the appropriate sulfonyl halide in the presence of a base such as triethylamine (TEA) and in a suitable solvent to afford compounds of Formula III. For compounds where $R_2$ and $R_1$ are hydrogen, oxidation of the N-sulfonyl primary alcohol with pyridinium chlorochromate (PCC) or under Swern conditions then affords the corresponding aldehyde IV which can be reacted with Grignard reagents (RMgX, where R is an organic radical and X is a halogen) to afford the secondary alcohols V as a mixture of diastereomers which can be separated by high performance liquid chromatography (HPLC) (Scheme 1).

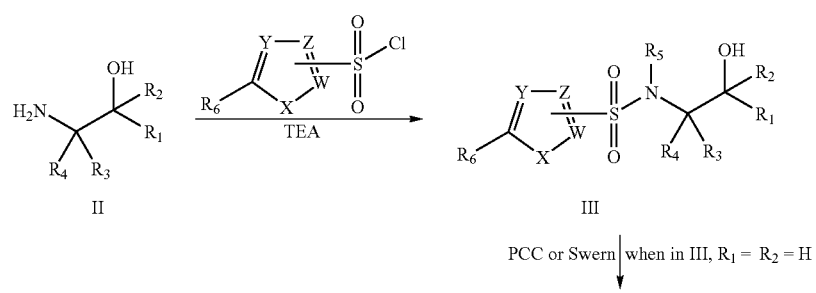

Scheme 1

-continued

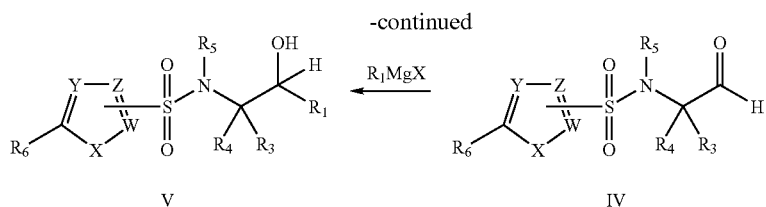

V    IV

A second method of preparation involves reaction of an α-amino acid or ester IX with the appropriate sulfonyl halide in the presence of a base such as triethylamine and in a suitable solvent to afford compounds of Formula X (Scheme 2). The intermediate N-sulfonyl acid X (Rx=H) can be converted to the corresponding primary alcohol VIII ($R_1$=$R_2$=H) utilizing standard methodology such as $LiAlH_4$, $B_2H_6$ or cyanuric chloride/$NaBH_4$. The intermediate N-sulfonyl ester X (Rx=alkyl, Bn) can also be reduced to the corresponding primary alcohol VIII ($R_1$=$R_2$=H) utilizing standard methodology such as $LiAlH_4$. Alternatively, the intermediate N-sulfonyl ester X (Rx=alkyl, Bn) can be converted to the aldehyde IV with DiBAL. Finally, the intermediate N-sulfonyl ester X (Rx=alkyl, Bn) can be reacted with 2 equivalents of Grignard reagent to afford the tertiary alcohols III with $R_1$=$R_2$. Alternatively, for tertiary alcohols III with $R_1$ not equal to $R_2$, the corresponding Weinreb amide (see Scheme 10) of the N-sulfonyl acid can be prepared and subsequently reacted with $R_1MgX$ and $R_2MgX$. For compounds of formula X (Rx=H) that have an asymmetric center at the α-amino acid carbon, the pure enantiomers can be obtained by standard resolution procedures employing recrystallization of salts formed with various chiral bases.

In a variation of the second method to prepare the primary alcohols, an α-amino acid or ester (or N-protected derivative thereof) VI is first converted to the corresponding primary 2-aminoalcohol VII (using the methodology outlined in the previous paragraph), which is subsequently, after deprotection (if necessary), reacted with the appropriate sulfonyl halide (Scheme 3) to afford compounds of Formula VIII. For preparation of compounds derived from unnatural α-amino acids containing beta branching in the amino acid side chain, a method of preparation based on the work of Hruby (*Tet. Lett.* 38: 5135-5138 (1997)) is outlined in Scheme 4. This route entails formation of the α,β-unsaturated amide XII of the Evans chiral auxiliary from an α,β-unsaturated acid XI, followed by conjugate addition of an organocuprate, trapping of the resulting enolate anion XIII with NBS, displacement of the bromide XIV with azide anion (provided by tetramethylguanidinium azide (TMGA)) to afford XV, followed by reduction to the 2-amino alcohol and subsequent sulfonylation to afford the target compound XVI. In Schemes 1 through 4, $R_5$ is H.

Scheme 2

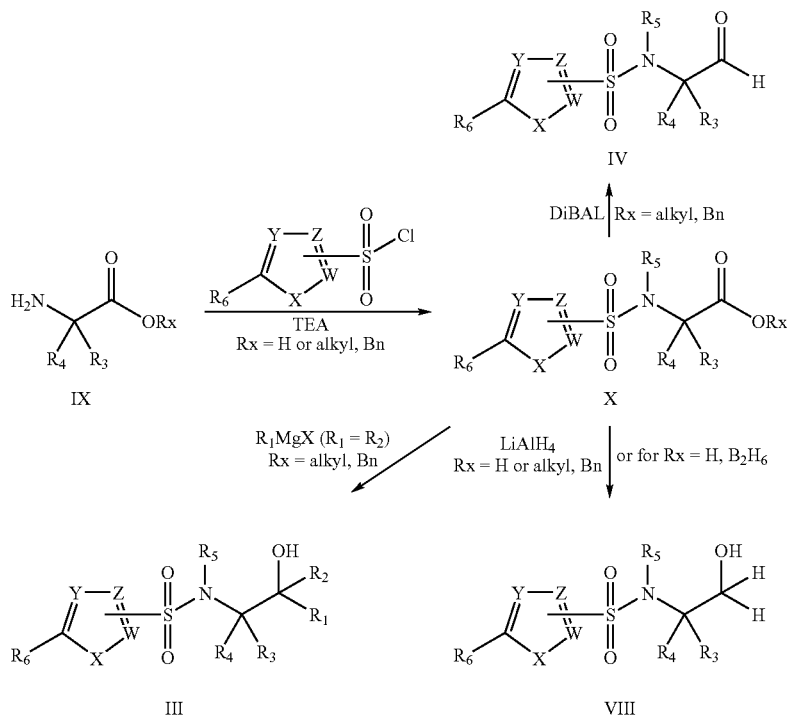

Scheme 3

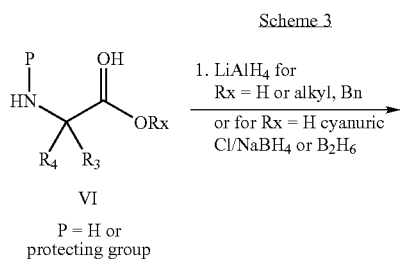
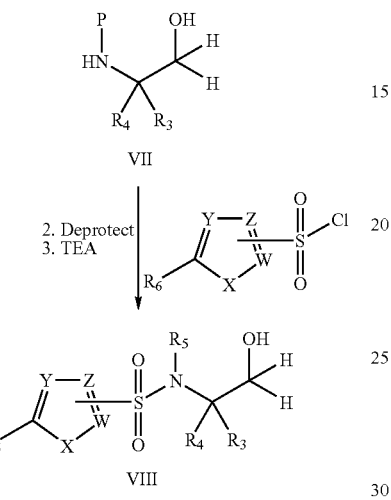

lated by either treatment with a suitable base such as potassium carbonate followed by the alkylating agent $R_5X$ or by employing Mitsunobu conditions ($R_5OH/DEAD$, TPP). $LiBH_4$ reduction of the N-alkylated sulfonamide ester affords the N-alkylated sulfonamide in the primary alcohol series VIII (Scheme 5). These primary alcohols VIII can be converted to the secondary alcohols V or aldehyde IV series by chemistry that has been outlined above. Alternatively, the N-alkylated sulfonamide esters, or their corresponding Weinreb amides, can be treated with Grignard reagents to afford the N-alkylated tertiary alcohols III.

Scheme 5

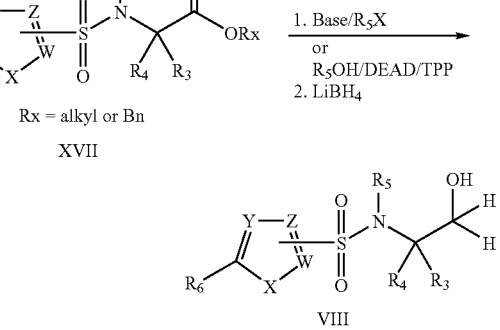

Scheme 4

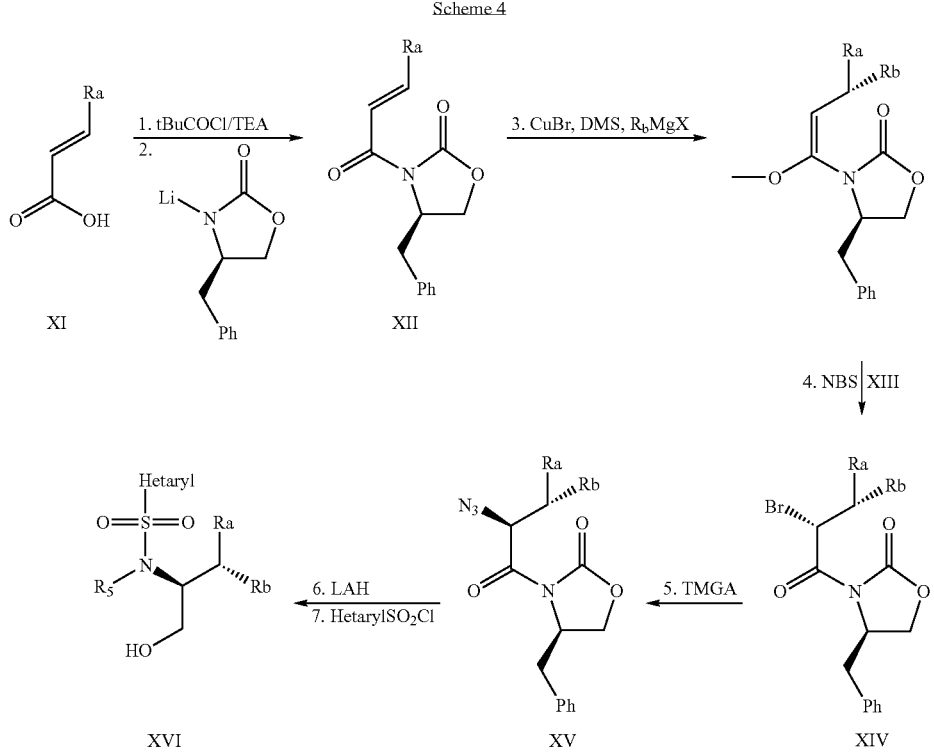

For the preparation of N-alkylated sulfonamides VIII ($R_5$=alkyl etc.), the sulfonamide ester XVII can be N-alky- When the heterocycle attached to the sulfonamide in the above alcohols is thiophene, the corresponding sulfone derivative XIX may be obtained by oxidation of the thiophene compound XVIII with MCPBA (Scheme 6).

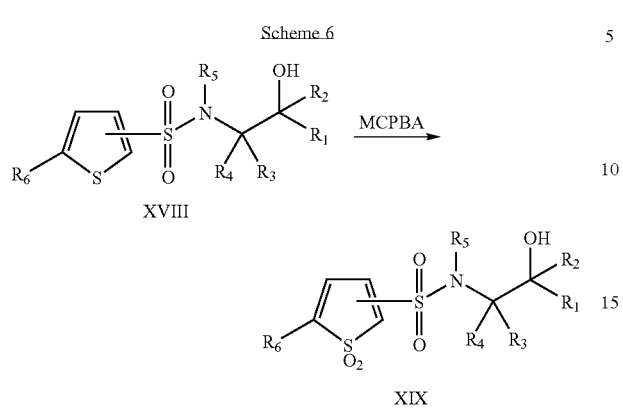

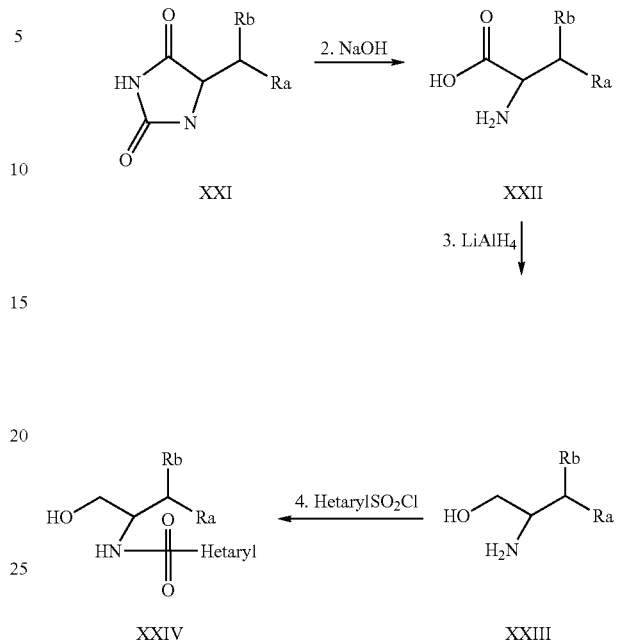

An alternate preparation of sulfonamides derived from unnatural 2-aminoalcohols utilizes the Bucherer modification of the Strecker α-amino acid synthesis (Scheme 7). In this route, an aldehyde XX is reacted with cyanide anion and ammonium carbonate to afford the hydantoin XXI, which is hydrolyzed to the α-amino acid XXII. This compound is then reduced to XXIII and sulfonylated to afford the desired compounds of Formula XXIV.

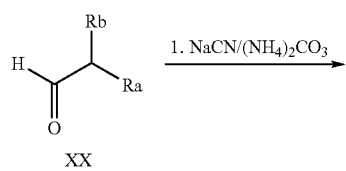

For sulfonamides derived from 2-aminoalcohols containing an N or O heteroatom in the side chain, a route has been devised starting from D-serine (Scheme 8). In this route, D-serine XXV is first sulfonylated to XXVI and subsequently converted to the ketone XXVII, which is reductively aminated to the target compounds of Formula XXVIII.

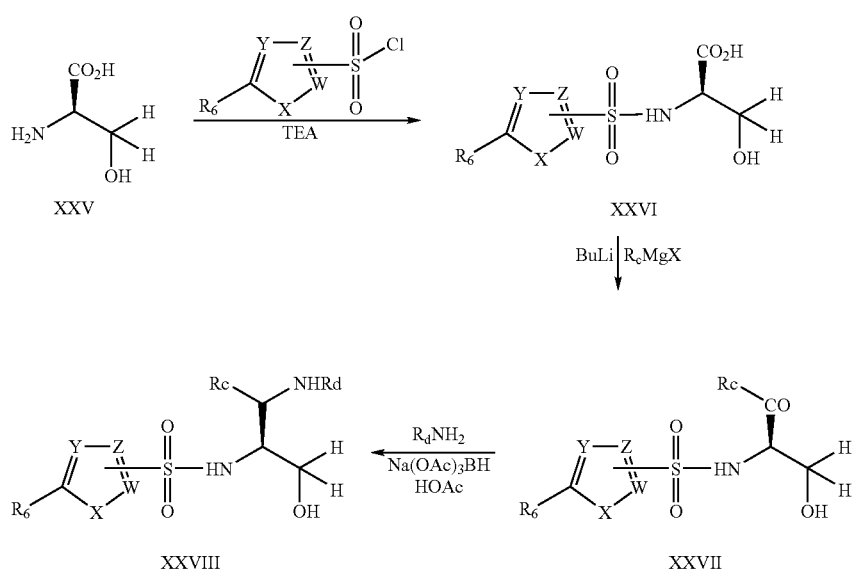

For sulfonamides derived from 2-aminoalcohols in the secondary alcohol series with $R_1$=H and $R_2$=$CF_3$ (compound XXIX), a method of preparation has been devised that is outlined in Scheme 9 starting from the aldehyde IV (prepared as in Scheme 1).

Scheme 9

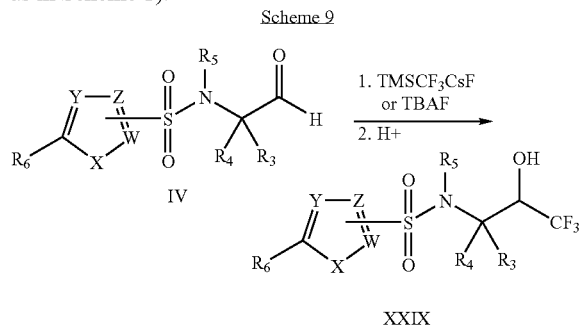

As has been mentioned in the section concerning Scheme 1, the preparation of sulfonamides derived from 2-aminoalcohols in the secondary alcohol series V results in the formation of a diastereomeric mixture. An alternate method of preparation of these compounds that results in the production of a pure diastereomer is outlined in Scheme 10 for compounds derived from L-isoleucine. This method, which utilizes chemistry previously employed by Roux (*Tetrahedron* 50: 5345-5360 (1994)), consists of addition of Grignard reagents to the Weinreb amide XXX (derived from the requisite α-amino acid) followed by stereospecific reduction of the ketone XXXI to afford a single diastereomeric N-protected 2-amino alcohol XXXII. Deprotection of this compound followed by reaction with sulfonyl chlorides affords the pure diastereomeric sulfonamide secondary alcohols of Formula XXXIII.

Scheme 10

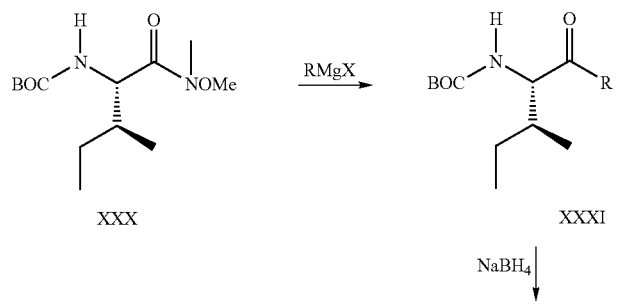

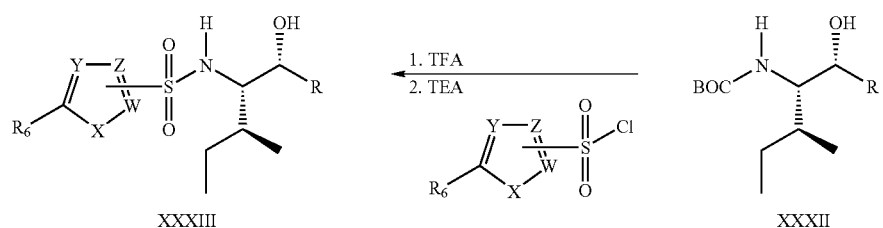

When the heterocycle attached to the sulfonamide in the above alcohols is thiophene, the corresponding 5-iodo and 5-fluoro-thiophene derivatives may be obtained by conversation of the 5-bromo-thiophene derivative XXXIV (obtained as in Scheme 1) to a 5-trialkyltin-thiophene intermediate XXXV which can be converted to either the 5-iodo-thiophene (XXXVII) by treatment with sodium iodide and chloramine T or the 5-fluoro-thiophene analog (XXXVI) by treatment with SELECTFLUOR™ (Aldrich Chemical Co) (Scheme 11).

described herein (Scheme 12). This route entails initial hydrogenation of 4-L-hydroxyphenylglycine XXXVIII, followed by sulfonylation, reduction of the carboxylic acid with diborane and formation of the N,O-acetonide XXXIX. The 4-hydroxy acetonide XXXIX is then O-alkylated using sodium hydride and an alkylating agent such as an alkyl or benzyl bromride. This is followed by removal of the protecting group by treatment with aqueous acid to afford the 4-ether derivatives of Formula XXXX. Alternatively, the 4-hydroxy

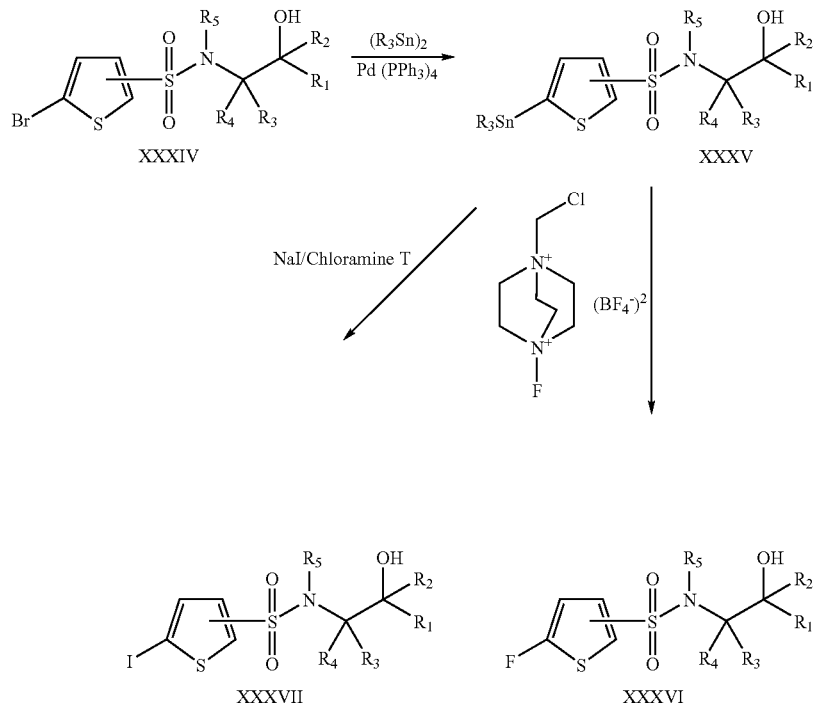

Sulfonamides derived from cyclohexylglycinol substituted by alkoxy and amino groups at the 4 position of the cyclohexane ring can be prepared according to the methods acetonide XXXIX can be oxidized to the 4-ketone which can be reductively aminated and deprotected to afford the corresponding 4-amino analogs of Formula XXXXI.

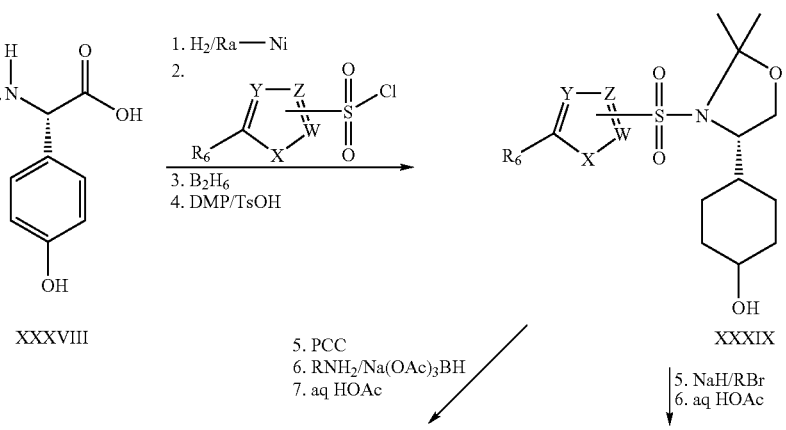

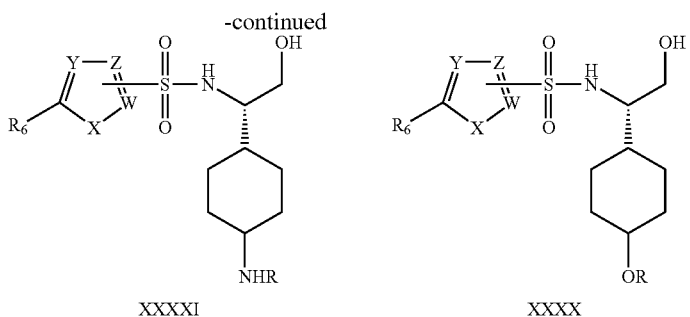

Another method of preparing chirally pure N-sulfonyl 2-amino alcohols derived from α-amino acids is outlined in Scheme 13. This method involves construction of an Evans oxazolidone chiral auxiliary XXXXIII from XXXXII, which is then converted to the corresponding enolate and electrophilically aminated with trisyl azide to afford the key intermediate XXXXIV (*J. Am. Chem. Soc.* 109: 6881-6883 (1987)). The azide intermediate XXXXIV is then hydrolyzed to the α-azido acid XXXXV and reduced to the chirally pure α-amino acid XXXXVI which can be converted to the corresponding N-sulfonyl 2-amino alcohols by methods previously described above (e.g. Scheme 2).

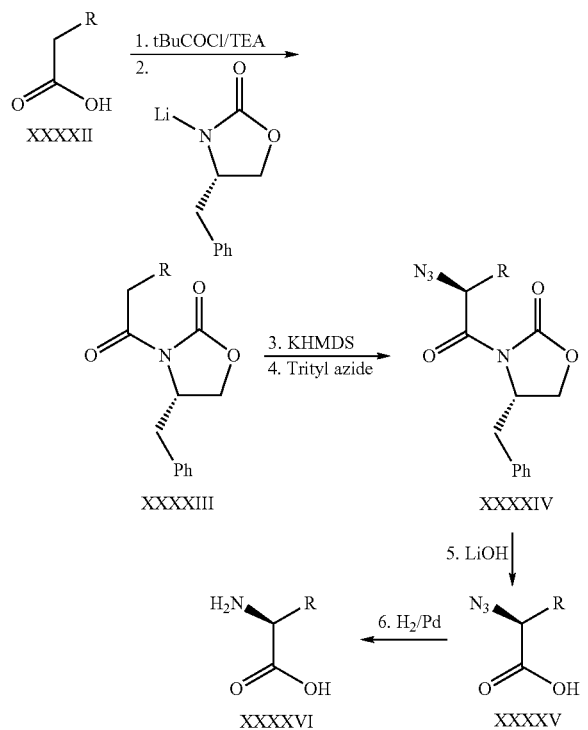

Finally, chirally pure α-amino acids XXXXVI, one of the possible synthetic precursors of chiral N-sulfonyl 2-amino alcohols as mentioned above, can also be prepared utilizing an asymmetric variant of the Strecker α-amino acid synthesis as outlined in Scheme 14 (*J. Org. Chem.* 54:1055-1062 (1989)).

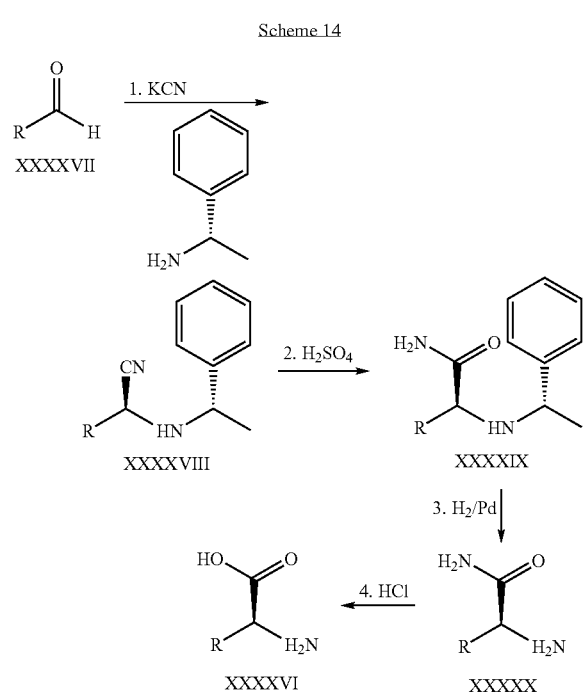

Oximes XXXXXIV can be derived from the corresponding aldehydes IV by standard methodology as depicted in Scheme 15.

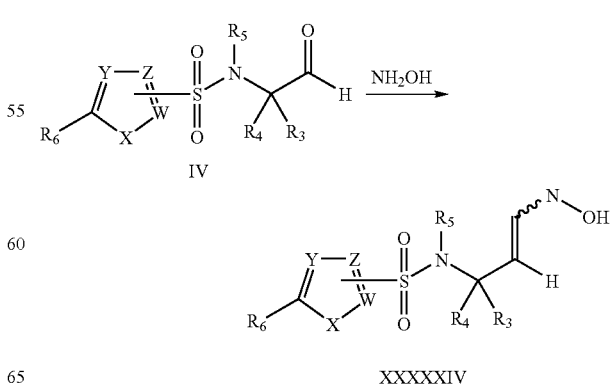

Methods of Use

Compounds of Formula (1) are inhibitors of beta amyloid production. In preliminary studies using protease specific assays, exemplary compounds of Formula (I) have been shown to exhibit specific inhibition with respect to protease activity. Thus, the compounds of the present invention are useful for treatment and prevention of a variety of conditions in which modulation of beta amyloid levels provides a therapeutic benefit. Such conditions include, e.g., amyloid angiopathy, cerebral amyloid angiopathy, systemic amyloidosis, Alzheimer's Disease (AD), hereditary cerebral hemorrhage with amyloidosis of the Dutch type, inclusion body myositis, Down's syndrome, among others.

In addition, the compounds of Formula (I) may be utilized in generating reagents useful in diagnosis of conditions associated with abnormal levels of beta amyloid. For example, the compounds of Formula (I) may be used to generate antibodies, which would be useful in a variety of diagnostic assays. Methods for generating monoclonal, polyclonal, recombinant, and synthetic antibodies or fragments thereof, are well known to those of skill in the art. (See, e.g., E. Mark and Padlin, "Humanization of Monoclonal Antibodies", Chapter 4, *The Handbook of Experimental Pharmacology*, Vol. 113, The Pharmacology of Monoclonal Antibodies, Springer-Verlag (June, 1994); Kohler and Milstein and the many known modifications thereof; PCT Patent Application No. PCT/GB85/00392; British Patent Application Publication No. GB2188638A; Amit et al., *Science,* 233:747-753 (1986); Queen et al., *Proc. Nat'l. Acad. Sci. USA,* 86:10029-10033 (1989); International Patent Publication No. WO90/07861; and Riechmann et al., *Nature,* 332:323-327 (1988); Huse et al, *Science,* 246:1275-1281 (1988)). Alternatively, the compounds of Formula (I) may themselves be used in such diagnostic assays. Regardless of the reagent selected (e.g., antibody or compound of Formula (I)), suitable diagnostic formats including, e.g., radioimmunoassays and enzyme-linked immunosorbent assays (ELISAs), are well known to those of skill in the art and are not a limitation on this embodiment of the invention.

The beta amyloid inhibitory activity of many of the compounds of the present invention has been determined using the Repressor Release Assay (RRA). See, Table 23 below. A compound is considered active in RRA if it leads to at least a 1.5 fold increase in luciferase activity at 20 µM and is nontoxic.

Additionally, cellular, cell-free and in vivo screening methods to detect inhibitors of beta amyloid production are known in the art. Such assays may include radioimmunoassays and enzyme-linked immunosorbent assay (ELISA), among others. See, e.g., P. D. Mehta, et al., Techniques in Diagnostic Pathology, vol. 2, eds., Bullock et al, Academic Press, Boston, pages 99-112 (1991), International Patent Publication No. WO 98/22493, European Patent No. 0652009, U.S. Pat. No. 5,703,129 and U.S. Pat. No. 5,593,846. Selection of an appropriate in vitro or in vivo screening assay is not a limitation of the present invention.

Pharmaceutical Formulation

The compounds of this invention may be administered to a subject by any desirable route, taking into consideration the specific condition for which it has been selected. By subject is meant any suitable mammal, including humans, domestic animals (e.g., canines and felines), and livestock, which have been recognized as having or at risk of having one or more of the conditions for which modulation of beta amyloid levels is desirable. Thus, the compounds of the invention are useful for treatment and/or prevention of a number of human and veterinary conditions. As used herein, "prevention" encompasses prevention of symptoms in a subject who has been identified as at risk for the condition, but has not yet been diagnosed with the same and/or who has not yet presented any symptoms thereof.

These compounds may be delivered or administered by any suitable route of delivery, e.g., oral, intravenous, subcutaneous, intramuscular, sublingual, intracranial, epidural, intratracheal, rectal, vaginal, among others. Most desirably, the compounds are delivered orally or by a suitable parenteral route. The compounds may be formulated in combination with conventional pharmaceutical carriers that are physiologically compatible. Optionally, one or more of the compounds of the invention may be mixed with other active agents.

Suitable physiologically compatible carriers may be readily selected by one of skill in the art. For example, suitable solid carriers include, among others, one or more substances which may also act as lubricants, solubilizers, suspending agents, fillers, glidants, compression aids, binders or tablet-disintegrating agents or an encapsulating material. In powders, the carrier is a finely divided solid, which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, starch, sugars (including, e.g., lactose and sucrose), dicalcium phosphate, cellulose (including, e.g., microcrystalline cellulose, methyl cellulose, sodium caroboxymethyl cellulose), and kaolin.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, suspending agents, thickening agents, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols, e.g., glycols) and their derivatives, and oils (e.g., fractionated coconut oil, arachis oil, corn oil, peanut oil, and sesame oil). For parenteral administration the carrier can also be an oily ester such as ethyl oleate and isopropyl myristate. Sterile liquid carriers are used in sterile liquid form compositions for parenteral administration.

Optionally, additives customarily employed in the preparation of pharmaceutical compositions may be included in the compositions of the invention. Such components include, e.g., sweeteners or other flavoring agents, coloring agents, preservatives, and antioxidants, e.g., vitamin E, ascorbic acid, BHT and BHA.

Liquid pharmaceutical compositions that are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

As described herein, a therapeutically or prophylactically useful amount of a compound of the invention is that amount of a compound which alleviates the symptoms of the disease, e.g., AD, or which prevents the onset of symptoms, or the onset of more severe symptoms. Generally, an individual dose (i.e., per unit, e.g., tablet) of a compound of the invention may be in the range from about 1 µg/kg to about 10 g/kg, more preferably 10 mg/kg to about 5 g/kg, and most preferably about 1 mg/kg to about 200 mg/kg. Desirably, these amounts are provided on a daily basis. However, the dosage to be used in the treatment or prevention of a specific cognitive deficit or other condition may be subjectively determined by the attending physician. The variables involved include the specific cognitive deficit and the size, age and response pattern of the patient. For example, based upon the activity profile and potency of the compounds of this invention, a starting dose of about 10 mg per day with gradual increase in the daily dose to about 200 mg per day may provide the desired dosage level in the human.

Alternatively, the use of sustained delivery devices may be desirable, in order to avoid the necessity for the patient to take medications on a daily basis. "Sustained delivery" is defined as delaying the release of an active agent, i.e., a compound of the invention, until after placement in a delivery environment, followed by a sustained release of the agent at a later time. Those of skill in the art know suitable sustained delivery devices. Examples of suitable sustained delivery devices include, e.g., hydrogels (see, e.g., U.S. Pat. Nos. 5,266,325; 4,959,217; and 5,292,515), an osmotic pump, such as described by Alza (U.S. Pat. No. 4,295,987 and U.S. Pat. No. 5,273,752) or Merck (European Patent No. 314,206), among others; hydrophobic membrane materials, such as ethylenemethacrylate (EMA) and ethylenevinylacetate (EVA); bioresorbable polymer systems (see, e.g., International Patent Publication No. WO 98/44964, Bioxid and Cellomeda; U.S. Pat. No. 5,756,127 and U.S. Pat. No. 5,854,388); other bioresorbable implant devices have been described as being composed of, for example, polyesters, polyanhydrides, or lactic acid/glycolic acid copolymers (see, e.g., U.S. Pat. No. 5,817,343 (Alkermes Inc.)). For use in such sustained delivery devices, the compounds of the invention may be formulated as described herein.

EXAMPLES

The following examples are provided to illustrate the production and activity of representative compounds of the invention and to illustrate their performance in a screening assay. One skilled in the art will appreciate that although specific reagents and conditions are outlined in the following examples, these reagents and conditions are not a limitation on the present invention.

Example 1

3-Bromo-5-chloro-N-[(1S,2S)-1-(hydroxymethyl)-2-methylbutyl]thiophene-2-sulfonamide

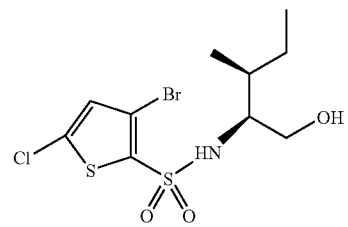

To a solution of (S)-+-isoleucinol (23 mg, 0.2 mmol) in THF (3 mL) was added triethylamine (46 µL, 0.24 mmol) and 3-bromo-5-chlorothiophene-2-sulfonyl chloride (59.2 mg, 0.2 mmol). The solution was stirred for 8-16 h, then concentrated. The residue was dissolved in MeOH (1.5 mL) and purified by semi-preparative RP-HPLC[1] to give Example 1 (20.3 mg).

The following compounds (Examples 1-7, Table 1) were prepared using 3-bromo-5-chlorothiophene-2-sulfonyl chloride, 5-bromothiophene-2-sulfonyl chloride, 3-bromo-2-chlorothiophene-5-sulfonyl chloride, 5-chlorothiophene-2-sulfonyl chloride, 2,5-dichlorothiophene-3-sulfonyl chloride, 2,3-dichlorothiophene-5-sulfonyl chloride, and 2-thiophenesulfonyl chloride and following the procedure outlined in Example 1.

TABLE 1

(LCMS[2] Data: Molecular ion and retention time)

| RSO$_2$Cl | (S)-(+)-isoleucinol |
|---|---|
| 3-bromo-5-chlorothiophene-2-sulfonyl chloride | Example 1 (377 M + H); 3.25 min |
| 5-bromothiophene-2-sulfonyl chloride | Example 2 (344 M + H); 3.01 min |
| 3-bromo-2-chlorothiophene-s-sulfonyl chloride | Example 3 (378 M + H); 3.35 min |
| 5-chlorothiophene-2-sulfonyl chloride | Example 4 (298 M + H); 2.97 min |
| 2,5-dichlorothiophene-3-sulfonyl chloride | Example 5 (332 M + H); 3.18 min |
| 2,3-dichlorothiophene-5-sulfonyl chloride | Example 6 (332 M + H); 3.33 min |
| 2-thiophenesulfonyl chloride | Example 7 (264 M + H); 2.35 min |

Example 8

5-Chloro-N-[(1S)-1-(hydroxymethyl)-2-methylpropyl]thiophene-2-sulfonamide

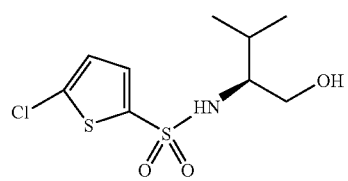

To a solution of L-valinol (25.8 mg, 0.25 mmol) in THF (3 mL) was added triethylamine (58 μL, 0.3 mmol) and 5-chlorothiophene-2-sulfonyl chloride (54 mg, 0.25 mmol). The solution was stirred for 8 to 16 h, then concentrated. The residue was dissolved in MeOH (1.5 mL) and purified by semi-preparative RP-HPLC[1] to give Example 8 (19.5 mg).

The following compounds (Examples 8-10, Table 2) were prepared using 5-thiophene-2-sulfonyl chloride and 5-bromothiophenesulfonyl chloride with L-valinol and D-valinol and following the procedure outlined in Example 8.

TABLE 2

(LCMS[2] Data: Molecular ion and retention time)

| | RSO₂Cl | |
|---|---|---|
| Amine | 5-chlorothiophene-2-sulfonyl chloride | 5-bromothiophene-2-sulfonyl chloride |
| L-valinol | Example 8 (284 M + H); 2.70 min | Example 9 (330 M + H); 2.75 min |
| D-valinol | | Example 10 (330 M + H); 2.75 min |

Example 11

4,5-Dibromo-N-[(1S)-1-(hydroxymethyl)-2-methyl-propyl]thiophene-2-sulfonamide

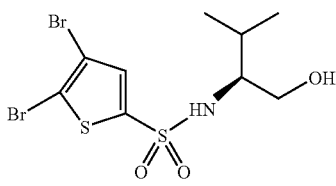

To a solution of (S)-(+)-2-amino-3-methyl-1-butanol (20.6 mg, 0.2 mmol) in THF (3 mL) was added triethylamine (46 μL, 0.24 mmol) and 4,5-dibromothiophene-2-sulfonyl chloride (68 mg, 0.2 mmol). The solution was stirred for 8 to 16 h, the solvent was removed and residue purified by RP-HPLC[1] to give Example 11 (49.6 mg).

TABLE 3

(LCMS[2] Data: Molecular ion and retention time)

| RSO₂Cl | NH₂CH(R₁)CH₂OH (S)-(+)-2-amino-3-methyl-1-butanol |
|---|---|
| 4,5-dibromothiophene-2-sulfonyl chloride | Example 11 (408 M + H); 3.22 min |

Example 12

5-Chloro-N-[(1S)-1-cyclohexyl-2-hydroxyethyl]thiophene-2-sulfonamide

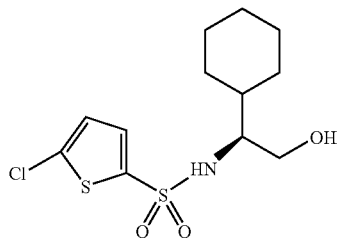

A. Part 1

To a solution of L-cyclohexyl-glycine (48.5 mg, 0.25 mmol) in THF (2 mL) was added lithium aluminum hydride (1 M solution in THF) (0.8 mL, 0.8 mmol) and the solution heated at 60° C. for 4 h. The solution was stirred at 25° C. for 8 to 16 hours. The reaction was quenched by addition of water (45 μL), 15% aqueous sodium hydroxide (45 μL) and water (105 μL) with vigorous stirring between each addition. The mixture was then filtered and concentrated.

B. Part 2

To a solution of the residue from Part 1 in THF (3 mL) was added triethylamine (69 μL, 0.50 mmol) and 5-chlorothiophene-2-sulfonyl chloride (54.3 mg, 0.25 mmol). The solution was stirred for 8 to 16 h, the solvent was removed and residue purified by RP-HPLC[1] to give Example 12 (25.9 mg).

The following compounds (Examples 12-17, Table 4) were prepared using 5-chlorothiophene-2-sulfonyl chloride, and 5-bromothiophene-2-sulfonyl chloride with L-cyclohexylglycine, β-methyl-DL-phenylalanine, and L-allo-isoleucine and following the procedure outlined in Example 12.

TABLE 4

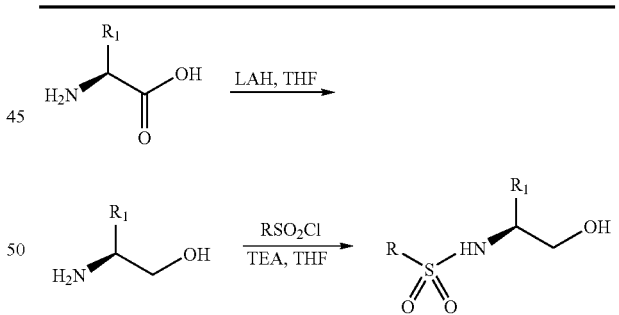

(LCMS[2] Data: Molecular ion and retention time)

| | RSO₂Cl | |
|---|---|---|
| Amino acid | 5-chlorothiophene-2-sulfonyl chloride | 5-bromothiophene-2-sulfonyl chloride |
| L-cyclohexyl-glycine | Example 12 (324 M + H); 3.07 min | Example 13 (370 M + H); 3.10 min |
| beta-methyl-DL-phenylalanine | Example 14 (346 M + H); 3.05 min | Example 15 (392 M + H); 3.08 min |
| L-allo-isoleucine | Example 16 (298 M + H); 2.78 min | Example 17 (344 M + H); 2.82 min |

Example 18

5-Bromo-N-[(1S,2S)-1-(hydroxymethyl)-2-methyl-butyl]thiophene-2-sulfonamide 1,1-dioxide

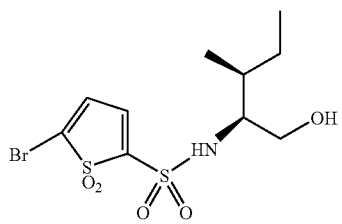

A. Part 1.

To a solution of (S)-+-isoleucinol (58.6 mg, 0.5 mmol) in DCM (5 mL) was added triethylamine (210 μL, 1.5 mmol) and 5-bromothiophene-2-sulfonyl chloride (130.8 mg, 0.5 mmol). The solution was stirred for 8 to 16 h, then concentrated.

B. Part 2.

The residue from Part 2 (0.5 mmol) was dissolved in dichloromethane (3 mL) and meta-chloroperbenzoic acid (2.5 mmol) was added. The solution was stirred for 8 to 16 h, the solvent was removed and residue purified by RP-HPLC to give Example 18 (4.3 mg). LCMS[2] Data: Molecular ion and retention time, 375.9 M+H); 3.37 min.

Example 19

5-Chloro-N-[1-(hydroxymethyl)-2,3-dimethylpentyl]thiophene-2-sulfonamide

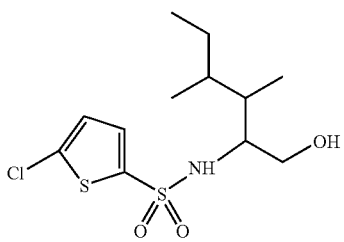

A. Part 1

To a solution of sodium cyanide (735.15 mg, 15 mmol) and ammonium carbonate (1.92 g, 20 mmol) in EtOH/H$_2$O (1:1, 35 mL) was added 2,3 dimethylpentanal (570.95 mg, 5 mmol). The solution was heated at 50° C. for 20 h, then concentrated.

B. Part 2

The residue from Part 1 (5 mmol) was dissolved in 35 mL of a 3N sodium hydroxide solution and heated at 95° C. for 22 h. Stirring was continued for an additional 8 to 16 h, then the solvent was removed.

C. Part 3

To the residue from Part 2 (2.5 mmol) in THF (10 mL) was added lithium aluminum hydride (1 M solution in THF) (5 mL, 5 mmol) and the solution heated at 60° C. for 4 h. The solution was stirred at 25° C. for 8 to 16 h. The reaction was quenched by addition of water (285 μL), 15% aqueous sodium hydroxide (285 μL), and water (665 μL) with vigorous stirring between each addition. The mixture was then filtered and concentrated.

D. Part 4

To the residue from Part 3 (0.5 mmol) in THF (5 mL) was added triethylamine (83.7 μL, 0.6 mmol) and 5-chlorothiophene-2-sulfonyl chloride (108.54 mg, 0.5 mmol). The solution was stirred for 8 to 16 h, the solvent was removed and residue purified by RP-HPLC[1] to give Example 19 (46.1 mg).

The following compounds (Examples 19-24, Table 5) were prepared using 2,3 dimethylpentanal, 2-methylvaleraldehyde, 2-ethylhexanal, 2,4,6-trimethyl-3-cyclohexene-1-carboxaldehyde, 1,2,3,6-tetrahydro-benzaldehyde, cyclopentylmethanal, and following the procedure outlined in Example 19.

TABLE 5

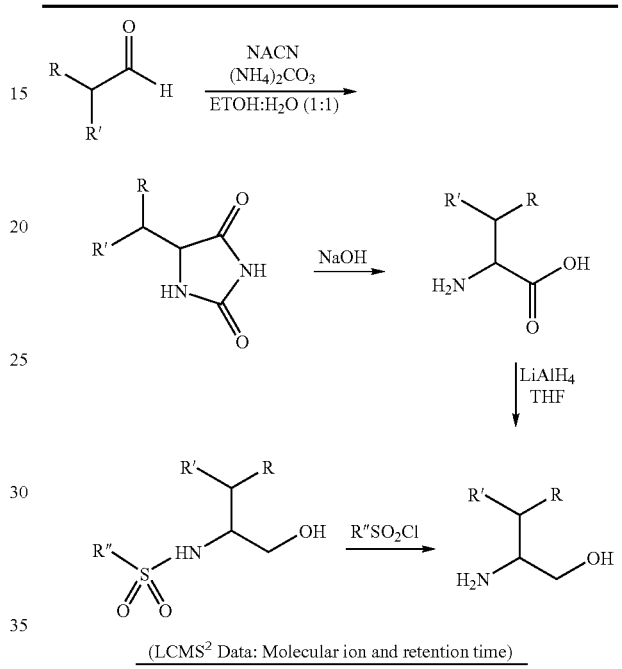

| Aldehyde | R″SO$_2$Cl<br>5-chlorothiophene-2-sulfonyl chloride |
|---|---|
| 2,3 dimethylpentanal | Example 19<br>(326 M + H); 3.47 min |
| 2-methylvaleraldehyde | Example 20<br>(312 M + H); 3.25 min |
| 2-ethylhexanal | Example 21<br>(340 M + H); 3.74 min |
| 2,4,6-trimethyl-3-cyclohexene-1-carboxaldehyde | Example 22<br>(364 M + H); 3.76 min |
| 1,2,3,6-tetrahydrobenzaldehyde | Example 23<br>(322 M + H); 3.11 min |
| Cyclopentylmethanal | Example 24<br>(310 M + H); 3.07 min |

(LCMS[2] Data: Molecular ion and retention time)

Example 25

5-Bromo-N-[(1S)-1-(hydroxymethyl)-1,2-dimethylpropyl]thiophene-2-sulfonamide

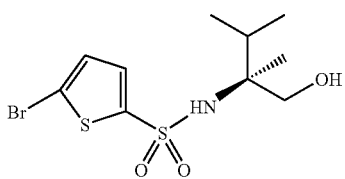

A. Part 1

To a solution of (S)-α-methyl valine (131 mg, 1 mmol) in THF (5 mL) was added lithium aluminum hydride (1M solution in THF) (2 mL, 2 mmol) and the solution was heated at 60° C. for 4 h. The solution was stirred at 25° C. for 8 to 16 h. The reaction was quenched by addition of water (114 µL), 15% aqueous sodium hydroxide (114 µL), and water (266 µL) with vigorous stirring between each addition. The mixture was then filtered and concentrated.

B. Part 2

To the residue from Part 1 (0.5 mmol) in THF (2 mL) was added triethylamine (83.7 µL, 0.6 mmol) and 5-bromothiophene-2-sulfonyl chloride (130.8 mg, 0.5 mmol). The solution was stirred for 8 to 16 h, the solvent was removed and residue purified by RP-HPLC[1] to give Example 25 (50.8 mg).

The following compounds (Examples 25-26, Table 6) were prepared using 5-bromothiophene-2-sulfonyl chloride and 5-chlorothiophene-2-sulfonyl chloride and following the procedure outlined in Example 25.

TABLE 6

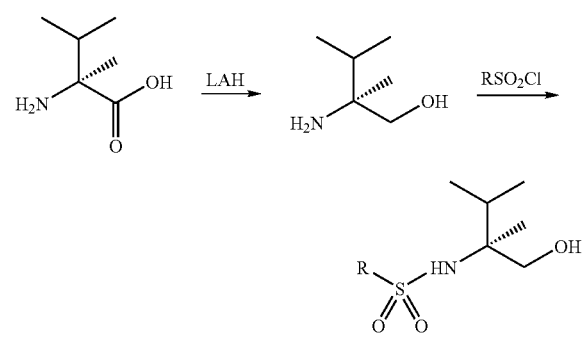

(LCMS[2] Data: Molecular ion and retention time)

| RSO$_2$Cl | S-α-methyl-valine |
| --- | --- |
| 5-bromothiophene-2-sulfonyl chloride | Example 25 (344 M + H); 2.97 min |
| 5-chlorothiophene-2-sulfonyl chloride | Example 26 (298 M + H); 2.92 min |

Example 27

5-Chloro-N-[(1S,2R)-1-(hydroxymethyl)-2,4-dimethylpentyl]thiophene-2-sulfonamide

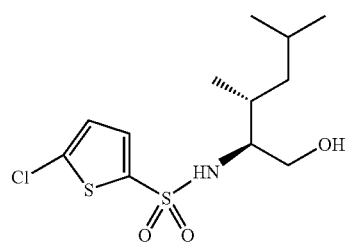

A. Part 1

A solution of 4-methyl-2-pentenoic acid (7.6 mL, 40 mmol) in THF (100 mL) was cooled to −78° C. Triethylamine (5.85 mL, 42 mmol) and trimethylacetyl chloride (pivaloyl chloride) (5.17 mL, 42 mmol) were added via syringe in that order. The dry ice bath was replaced with an ice bath and the reaction stirred at 0° C. for 1 h, then the reaction was recooled to −78° C.

In a separate flask (R)-(+)-4-benzyl-2-oxazolidinone (7.0 g, 40 mmol) was dissolved in THF (100 mL) and cooled to −78° C., then n-butyl lithium (1.6 M, 25 mL) was added via syringe. The mixture was stirred for 20 min then the above reaction mixture added by removing the septum and pouring quickly from one flask to the other (Note: attempts to transfer reaction mixture via cannula failed due to the suspended trimethylammonium chloride in the mixture).

The resulting mixture was stirred at −78° C. for 30 min then allowed to warm to 25° C. for 1 to 2 h before quenching with saturated aqueous NH$_4$Cl solution (100 mL). Volatiles were removed on the rotary evaporator and the aqueous slurry was diluted with water (200 mL) and extracted with ethyl acetate (2×200 mL). The combined organic phase was dried over anhydrous MgSO$_4$, filtered and concentrated. The product may crystallize out of solution and be of high purity. If purification is required the crude product may be purified by flash chromatography using 20 to 30% ethyl acetate in hexane.

B. Part 2

To a copper (I) bromide/dimethyl sulfide complex (246 mg, 1.2 mmol) in THF/DMS (2:1, 15 mL), cooled to −40° C., was added methyl magnesium bromide (2.4 mL, 1 M solution in THF, 2.4 mmol). The solution was allowed to stir for 10 min while warming to −15° C. The mixture was recooled to −40° C. and the product from Part 1 (245 mg, 1 mmol) in THF (6 mL) was added. The solution was stirred at 25° C. for 8 to 16 h. The solution was recooled to −78° C. and N-bromosuccinimide (356 mg, 2 mmol) in THF (2 mL) was added. The solution was allowed to warm to 0° C. and shaken at 0° C. for 3 h. The reaction was quenched with a 1:1 solution of saturated ammonium carbonate and 0.5 N potassium bisulfate (5 mL). The organic phase was decanted off and concentrated.

C. Part 3

To the product from Part 3 dissolved in acetonitrile (5 mL) was added tetramethylguanidine azide (0.6 mL, 4 mmol). The solution was stirred for 72 to 120 h. The solution was concentrated to dryness, redissolved in CH$_2$Cl$_2$ and 1 N HCl (2 mL) was added. The layers were separated and the organic layer was filtered through a pad of silica gel washed with CH$_2$Cl$_2$ (5 mL) and concentrated.

D. Part 4

To the product from Part 3 (131 mg, 1 mmol) in THF (5 mL) at 0° C. was added lithium aluminum hydride (1 M solution in THF) (2 mL, 2 mmol) and the solution stirred at 25° C. for 4 h. The reaction was quenched by addition of water (114 µL), 15% aqueous sodium hydroxide (114 µL), and water (266 µL) with vigorous stirring between each addition. The mixture was then filtered and concentrated.

E. Part 5

To the residue from Part 4 (0.5 mmol) in THF (2 mL) was added triethylamine (83.7 µL, 0.6 mmol) and 5-chlorothiophene-2-sulfonyl chloride (108 mg, 0.5 mmol). The solution was stirred for 8 to 16 h, the solvent was removed and residue purified as described for Example 1 to give 50.8 mg.

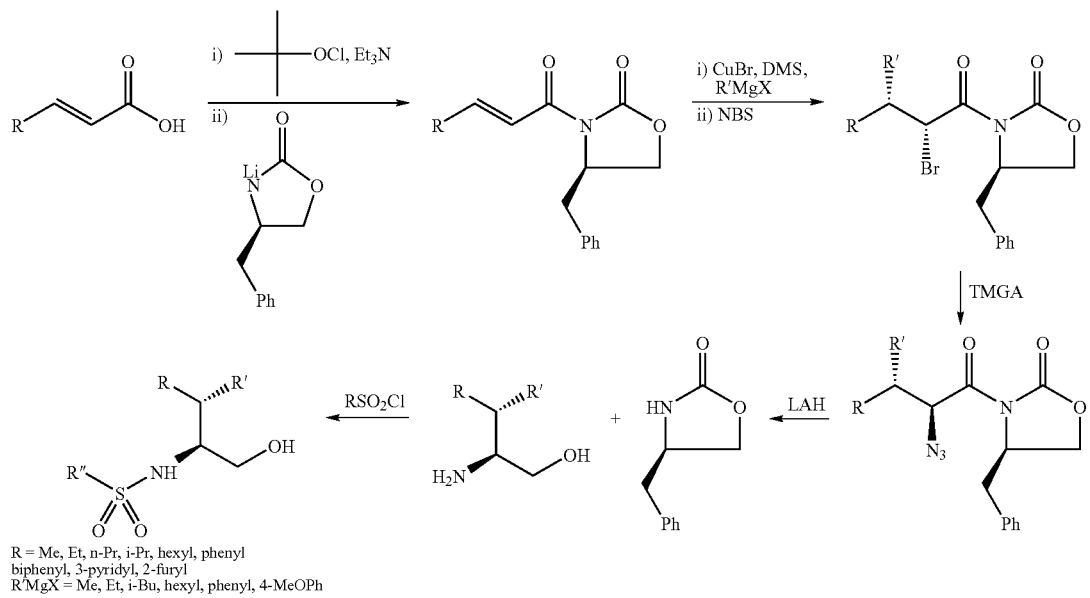

R = Me, Et, n-Pr, i-Pr, hexyl, phenyl
biphenyl, 3-pyridyl, 2-furyl
R'MgX = Me, Et, i-Bu, hexyl, phenyl, 4-MeOPh The following compounds (Examples 27-55, Table 7) were prepared using 5-chlorothiophene-2-sulfonyl chloride with crotonic acid, 2-pentenoic acid, 2-hexenoic acid, 2-octenoic acid, cinnamic acid, furylacrylic acid, 4-methyl-2-pentenoic acid, and 4-phenylcinnamic acid and methyl, ethyl, isobutyl, 4-methoxyphenyl, hexyl and phenyl magnesium bromide and following the procedure outlined in Example 27.

TABLE 7

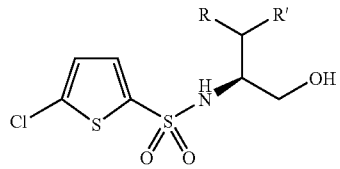

(LCMS$^2$ Data: Molecular ion and retention time)

| | R'MgX | | | | | | |
|---|---|---|---|---|---|---|---|
| R | methyl | ethyl | Isobutyl | 4-methoxyphenyl | hexyl | phenyl | n-propyl |
| methyl | | | Ex. 27 (326 M + H); 3.50 min | Ex. 28 (376 M + H); 3.13 min | Ex. 29 (354 M + H); 4.05 min | | |
| ethyl | | Ex. 30 (312 M + H); 3.18 min | Ex. 31 (340 M + H); 3.69 min | Ex. 32 (390 M + H); 3.32 min | | | |
| n-propyl | Ex. 33 (312 M + H); 3.26 min | Ex. 34 (326 M + H); 3.49 min | Ex. 35 (354 M + H); 3.93 min | Ex. 36 (404 M + H); 3.66 min | Ex. 37 (382 M + H); 4.46 min | Ex. 38 (374 M + H); 3.744 min | Ex. 39 (340 M + H); 3.6 min |
| pentyl | Ex. 40 (340 M + H); 3.79 min | Ex. 41 (354 M + H); 4.00 min | Ex. 42 (382 M + H); 4.39 min | Ex. 43 (432 M + H); 4.11 min | Ex. 44 (410 M + H); 4.57 min | Ex. 45 (402 M + H); 4.185 min | |
| phenyl | Ex. 46 (346 M + H); 3.27 min | | Ex. 47 (388 M + H); 3.91 min | | | | |

TABLE 7-continued

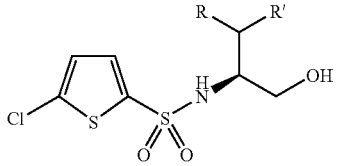

(LCMS² Data: Molecular ion and retention time)

| | R'MgX | | | | | | |
|---|---|---|---|---|---|---|---|
| R | methyl | ethyl | Isobutyl | 4-methoxy phenyl | hexyl | phenyl | n-propyl |
| 2-furyl | Ex. 48 (336 M + H); 3.00 min | Ex. 49 (350 M + H); 3.28 min | Ex. 50 (378 M + H); 3.69 min | | Ex. 51 (406 M + H); 4.19 min | | |
| i-propyl | | | | | Ex. 52 (382 4.47 min | | |
| biphenyl | Ex. 53 (422 M + H); 3.90 min | Ex. 54 (436 M + H); 4.14 min | Ex. 55 (464 M + H); 4.46 min | | | | |

The following compounds (Examples 56-76, Table 8) were prepared using 5-bromothiophene-2-sulfonyl chloride with crotonic acid, 2-pentenoic acid, 2-hexenoic acid, 2-octenoic acid, cinnamic acid, β-(3-pyridyl)-acrylic acid, furylacrylic acid, 4-methyl-2-pentenoic acid, and 4-phenylcinnamic acid and methyl, ethyl, isobutyl, 4-methoxyphenyl, hexyl and phenyl magnesium bromide and following the procedure outlined in Example 27.

TABLE 8

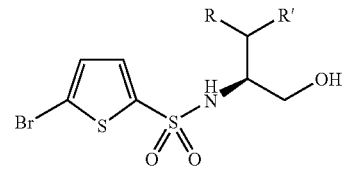

(LCMS² Data: Molecular ion and retention time)

| | R'MgX | | | | |
|---|---|---|---|---|---|
| R | methyl | ethyl | isobutyl | 4-methoxy phenyl | Hexyl |
| methyl | | | Ex. 56 (372 M + H); 3.52 min | | Ex. 57 (400 M + H); 4.07 min |
| ethyl | | Ex. 58 (358 M + H); 3.26 min | Ex. 59 (386 M + H); 3.71 min | | |
| n-propyl | | Ex. 60 (372 M + H); 3.52 min | Ex. 61 (400 M + H); 3.95 min | | |
| pentyl | | Ex. 62 (400 M + H); 4.02 min | Ex. 63 (428 M + H); 4.41 min | Ex. 64 (478 M + H); 4.12 min | Ex. 65 (456 M + H); 4.57 min |
| phenyl | Ex. 66 (392 M + H); 3.31 min | Ex. 67 (405 M + H); 3.55 min | Ex. 68 (434 M + H); 3.93 min | | |
| pyridyl | | | Ex. 69 (433 M + H); 2.67 min | | |
| 2-furyl | Ex. 70 (382 M + H); 3.04 min | Ex. 71 (395 M + H); 3.32 min | Ex. 72 (424 M + H); 3.71 min | | Ex. 73 (452 M + H); 4.21 min |

TABLE 8-continued (LCMS² Data: Molecular ion and retention time)

| | | | R'MgX | | |
|---|---|---|---|---|---|
| R | methyl | ethyl | isobutyl | 4-methoxy phenyl | Hexyl |
| i-propyl | | Ex. 74 (372 M + H); 3.49 min | Ex. 75 (400 M + H); 3.96 min | | |
| biphenyl | | Ex. 76 (482 M + H); 4.16 min | | | |

Example 77A

5-Chloro-N-[(1S,2R)-2-ethyl-1-(hydroxymethyl) octyl]thiophene-2-sulfonamide

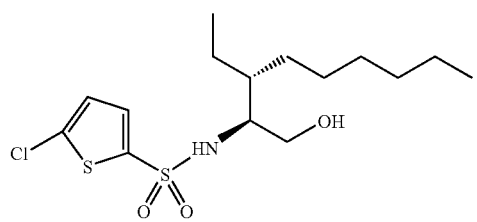

Following the procedure outlined in Example 27 (Part 1 and 2), 2-pentenoic acid was coupled with 4R-4-benzyl-2-oxazolidinone to give R-3-(2'-pentenyl)-4-benzyl-2-oxazolidinone. Addition of hexyl magnesium bromide was followed by trapping by N-bromosuccinimide. After workup, flash chromatography over silica gel using 5% ether in hexane, gave approximately a 2:1 mixture of (1R-2R)-: (1R-2S)-3-(2'-bromo-3'ethylnonanyl)-4-benzyl-2-oxazolidinone.

Each isomer was converted to the corresponding sulfonylated amino alcohol following the procedure in Example 27, (Steps 3-5).

TABLE 9

(LCMS² Data: Molecular ion and retention time)

| | 5-chlorothiophene-2-sulfonyl | 5-bromothiophene-2-sulfonyl |
|---|---|---|
| 1S-2R | Example 77A (368 M + H) 4.24 min | Example 78A (414 M + H) 4.26 min |

TABLE 9-continued (LCMS² Data: Molecular ion and retention time)

| | 5-chlorothiophene-2-sulfonyl | 5-bromothiophene-2-sulfonyl |
|---|---|---|
| 1S-2S | Example 77B (368 M + H) 4.24 min | Example 78B (414 M + H) 4.26 min |

Example 79

5-Chloro-N-[(1S)-1-(hydroxymethyl)-2-(methylamino)butyl]thiophene-2-sulfonamide

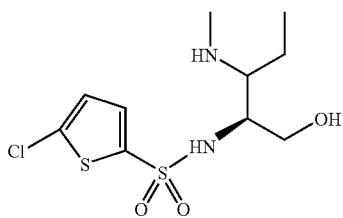

A. Part 1:

To a solution of D-serine (1.05 g, 10 mmol) in H₂O/THF (1:1, 100 mL) at 0° C. was added sodium hydroxide (2.17 g, 30 mmol) and 5-chlorothiophene-2-sulfonyl chloride (2.17 g, 10 mmol). The solution was stirred for 2 to 3 h, then the organic phase was concentrated and the aqueous phase acidified with 1 N HCl and extracted into ethyl acetate and concentrated.

B. Part 2:

To the residue from Part 1 (2.5 mmol) dissolved in THF (25 mL) at −78° C. was added ethyl magnesium bromide (7.5 mL, 7.5 mmol). The mixture was warmed to 25° C. and allowed to stir for 48 h. It was then acidified with 1 N HCl and extracted into ethyl acetate and concentrated.

C. Part 3:

To the product from Part 2 (0.1 mmol) dissolved in DMF (500 μL) was added $CH_2Cl_2$ (1.5 mL), acetic acid (12 μL, 0.2 mmol) and methyl amine (2 M solution in THF) (100 μL, 0.2 mmol). The reaction was stirred for 5 min and sodium triacetoxyborohydride (105.6 mg, 0.5 mmol) was added. The solution was allowed to stir for 8-16 h and purified by RP-HPLC[1] to give Example 79 (6.8 mg).

The following compounds (Examples 79-86, Table 10) were prepared using methyl, ethyl or pentyl magnesium bromide with methylamine (2M soln in THF), ethylamine (2M soln in THF), ethanolamine, benzylamine, and cyclopentylamine and following the procedure outlined in Example 79.

TABLE 10

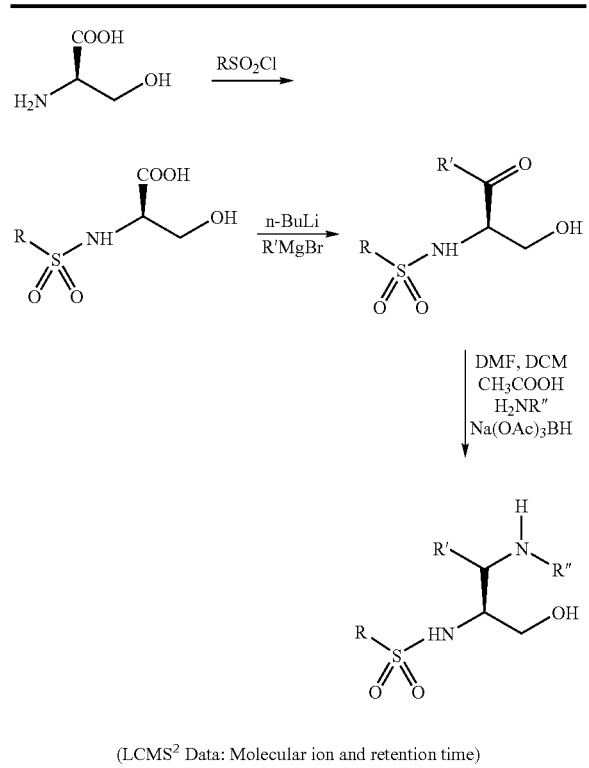

(LCMS[2] Data: Molecular ion and retention time)

| | R'MgBr | | |
|---|---|---|---|
| NHR" | methyl | ethyl | pentyl |
| Methylamine | Example 79 (313.0 M + H); 1.67 min | | |
| ethylamine | Example 80 (313.0 M + H); 1.53 min | | |
| Ethanolamine | Example 81 (329.0 M + H); 1.22 min | Example 82 (343.0 M + H); 1.73 min | Example 83 (385.0 M + H); 2.36 min |
| Benzylamine | Example 84 (375.0 M + H); 2.12 min | Example 85 (389.0 M + H); 2.25 min | |
| cyclopentylamine | Example 86 (353.0 M + H); 1.99 min | | |

Example 87

5-Chloro-N-[(1S,2S)-1-(hydroxymethyl)-2-methylbutyl]-N-(2-phenoxyethyl)thiophene-2-sulfonamide

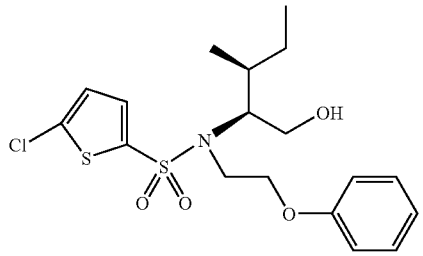

A. Part 1

To a solution of L-isoleucine methyl ester hydrochloride (1.82 g, 10 mmol) and 5-chlorothiophene-2-sulfonyl chloride (1.82 g, 10 mmol) was added triethylamine (4.18 mL, 30 mmol). The mixture was stirred at 60° C. overnight, then filtered and concentrated. The crude product was purified by flash chromatography over silica gel using 10% ethyl acetate in hexane to give 5-chlorothiophene-2-sulfonyl isoleucine methyl ester 2.53 g.

B. Part 2

To a solution of 5-chlorothiophene-2-sulfonyl isoleucine methyl ester (103 mg, 0.25 mmol) in DMF (1 mL) was added β-bromophenetole (55 mg, 0.5 mmol) and potassium carbonate (103 mg, 0.75 mmol. The reaction was shaken at 25° C. overnight, then concentrated.

C. Part 3

The residue from part 2 was dissolved in 5% methanol in THF (1 mL) and lithium borohydride (11 mg, 0.5 mmol) added. The reaction was shaken at 25° C. for 2 days then quenched by addition of water (1 mL) and extracted into ethyl acetate (3.5 mL). The organic phase was evaporated and the residue purified by RP-HPLC[1] to give Example 87 (48 mg).

The following compounds (Examples 87-88, Table 11) were prepared using β-bromophenetole, 3-chlorobenzyl bromide and following the procedure outlined in Example 87.

TABLE 11

(LCMS[2] Data: Molecular ion and retention time)

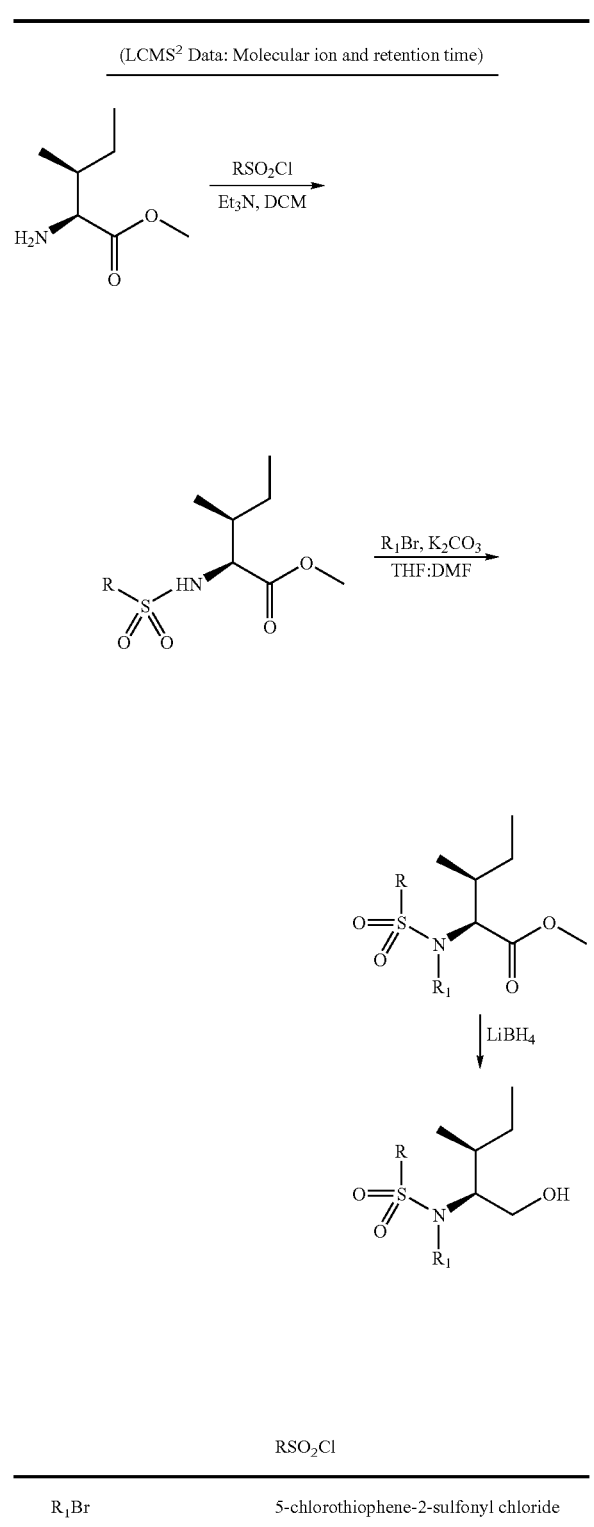

| R₁Br | RSO₂Cl |
|---|---|
|  | 5-chlorothiophene-2-sulfonyl chloride |
| β-bromophenetole | Example 87 |
|  | (418.0 M + H); 4.05 min |
| 3-chlorobenzyl bromide | Example 88 |
|  | (422.0 M + H); 4.12 min |

Example 89

5-Chloro-N-[(S)-2-hydroxy-1-phenylethyl]thiophene-2-sulfonamide

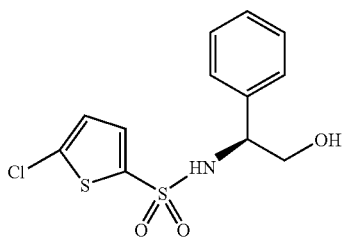

To a solution of (S)-(+)-2-phenylglycinol (6.8 mg, 0.05 mmol) in CH₃CN (200 μL) was added Et₃N (105 μL, 1M in CH₃CN) and 5-chlorothiophene-2-sulfonyl chloride (10.9 mg, 0.05 mmol) as a solution in CH₃CN (200 μL). The vial was capped and shaken for 8 to 12 h at 40° C. Solvent was removed in vacuo, and the residue dissolved in 1.6 mL DMSO (0.03 M).

The following compounds (Examples 89-117, Table 12) were prepared using 5-chlorothiophene-2-sulfonyl chloride and 5-bromothiophene-2-sulfonyl chloride with (S)-(+)-2-phenylglycinol, L-leucinol, DL-2-amino-1-hexanol, 2-amino-2-methyl-1-propanol, 2-amino-2-ethyl-1,3-propanediol, cycloleucinol, (S)-cyclohexylalaninol, L-phenylalaninol, L-methioninol, DL-2-amino-1-pentanol, L-tert-leucinol, chloramphenicol, (S)-(+)-2-amino-1-butanol, (S)-benzyl-L-cysteinol, benzyl-L-threoninol, 4-methylbenzyl-H-cysteinol, benzyl-H-tyrosinol, and L-threoninol following the procedure outlined in Example 89.

TABLE 12

(LCMS Data: Molecular ion and retention time)

| Amine | X = Cl | X = Br |
|---|---|---|
| (S)-(+)-2-phenylglycinol | Example 89 | Example 104 |
|  | (316.46 M-H), 0.95 min | (361.31 M-H); 0.98 min |
| L-leucinol | Example 90 | Example 105 |
|  | (296.48 M-H), 1.01 min | (342.41 M-H); 1.02 min |
| DL-2-amino-1-hexanol | Example 91 | Example 106 |
|  | (296.49 M-H), 1.02 min | (342.39 M-H); 1.04 min |
| 2-amino-2-methyl-1-propanol | Example 92 | Example 107 |
|  | (268.45 M-H), 0.81 min | (314.38 M-H); 0.83 min |
| 2-amino-2-ethyl-1,3-propanediol | Example 93 | Example 108 |
|  | (298.46 M-H), 0.69 min | (344.37 M-H); 0.69 min |
| cycloleucinol | Example 94 | Example 109 |
|  | (295.02 M-H), 0.92 min | (340.4 M-H); 0.93 min |

TABLE 12-continued (LCMS Data: Molecular ion and retention time)

| Amine | X = Cl | X = Br |
|---|---|---|
| (S)-cyclohexylalaninol | Example 95 (336.31 M-H), 1.19 min | Example 110 (382.41 M-H); 1.2 min |
| L-phenylalaninol | Example 96 (330.50 M-H), 1.03 min | |
| L-methioninol | | Example 111 (360.33 M-H); 0.9 min |
| DL-2-amino-1-pentanol | Example 97 (282.68 M-H), 0.92 min | (Example 112 327.07 M-H); 0.94 min |
| L-tert-leucinol | Example 98 (296.50 M-H), 1.22 min | Example 113 (341.44 M-H); 1.01 min |
| Chloramphenicol | Example 99 (391.44 M-H), 0.89 min | |
| (S)-(+)-2-amino-1-butanol | Example 100 (268.45 M-H), 0.61 min | |
| S-benzyl-L-cysteinol | Example 101 (377.77 M-H), 1.13 min | Example 114 (422.35 M-H); 1.15 min |
| benzyl-L-threoninol | Example 102 (374.49 M-H), 1.21 min | |
| 4-methylbenzyl-H-cysteinol | | Example 115 (436.31 M-H); 1.01 min |
| benzyl-H-tyrosinol | | Example 116 (480.43 M-H); 1.15 min |
| L-threoninol | Example 103 284.10 (M-H), 0.58 min | Example 117 329.99 (M-H), 0.68 min |

Example 118

5-Chloro-N-[(S,S)-1-formyl-2-methylbutyl]thiophene-2-sulfonamide

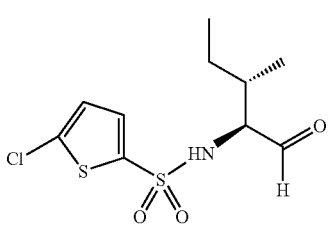

A. Part 1

To a solution of 5-chlorothiophene-2-sulfonyl chloride (11 g, 50.7 mmol) in CH$_3$CN (100 mL) and (S)-isoleucinol (6.2 g, 53 mmol) was added Et$_3$N (11 mL, 109 mmol). The reaction mixture was heated at 50° C. with stirring for 24 h. The solvent was removed and the oil was dissolved in EtOAc (100 mL). The solution was washed with water (2×100 mL), brine (1×100 mL), and dried over Na$_2$SO$_4$. The solvent was removed to give 13.85 g (88%) of the desired sulfonamide.

B. Part 2

Molecular sieves (15 g, 4 Å) were stirred in dry CH$_2$Cl$_2$ (175 mL) for 10 min. Then a mixture of pyridinium chlorochromate (8.6 g, 39.9 mmol) and silica gel (9 g) 15 was added and the mixture was stirred an additional 10 min. To the suspension was added 5-chlorothiophene-2-sulfonyl isoleucinol (4 g, 13.4 mmol) dissolved in CH$_2$Cl$_2$ (15 mL) and the resulting slurry was stirred for 2 h. The reaction mixture was filtered and the solvent was removed. The residue was subjected to a Biotage™ eluting with 20% EtOAc/hexane to give 3.22 g (81%) of the aldehyde (LCMS=294.21 (M–H), rt=1.10 min).

Example 119

5-Chloro-N-[(S,S)-1-(1-hydroxyethyl)-2-methylbutyl]thiophene-2-sulfonamide

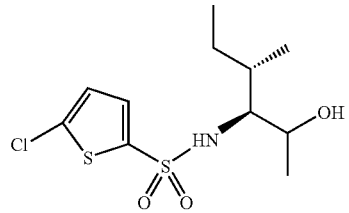

To a solution of the aldehyde from example 118 (23.7 mg, 0.08 mmol) in THF (400 μL) was added methyl magnesium bromide (400 μL, 1.0 M in THF, 5 eq). The vial was capped and agitated at 50° C. for 12 h. The reaction was quenched with sat. aqueous NH$_4$Cl (1.5 mL) and EtOAc (1 mL). The organic layer was transferred into a tarred vial and the aqueous layer was extracted with EtOAc (1 mL). The combined organics were concentrated (Savant, medium heat) and the resulting mixture of diastereomers was dissolved in DMSO such that the final concentration was 360 mM.

The following compounds (Examples 119-154, Table 13) were prepared using 5-chlorothiophene-2-sulfonyl isoleucinal (example 118) and 5-bromothiophene-2-sulfonyl isoleucinal (prepared as in example 118) with methylmagnesium bromide, cyclopentylmagnesium bromide, hexylmagnesium bromide, pentylmagnesium bromide, butylmagnesium bromide, isopropylmagnesium bromide, o-tolylmagnesium bromide, tert-butylmagnesium bromide, isobutylmagnesium bromide, vinylmagnesium bromide, allylmagnesium bromide, ethylmagnesium bromide, 4-fluorophenylmagnesium bromide, 4-chlorophenylmagnesium bromide, 2-methyl-1-propenylmagnesium bromide, isopropenylmagnesium bromide, 4-anisylmagnesium bromide, 1-methyl-1-propenylmagnesium bromide, 2-[2-(1,3-dioxanyl)]ethylmagnesium bromide, 3-butenylmagnesium bromide, 1-propynylmagnesium bromide, 4-thioanisolemagnesium bromide, and 4-N,N-dimethylanilinemagnesium bromide following the procedure outlined in example 119. Note: during the reaction sequence with the 5-bromothiophene compounds, the bromine is converted to a hydrogen on the thiophene ring.

TABLE 13

(LCMS Data: Molecular ion and retention time)

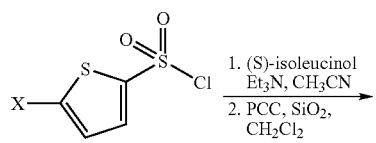

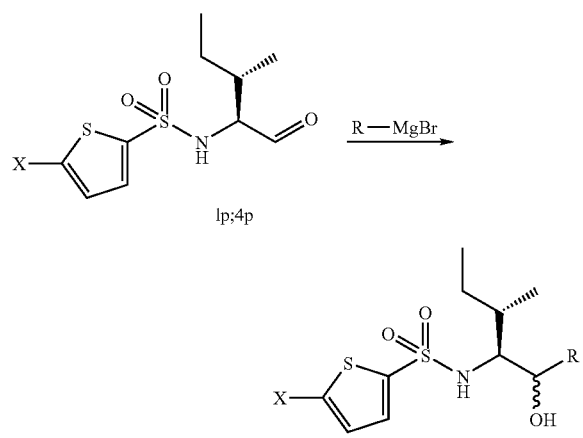

| R—MgBr | 5-chlorothiophene | thiophene |
|---|---|---|
| methylmagnesium bromide | Ex. 119 | |
| | 310.09(M − H), 1.06 min | |
| | 310.10(M − H), 1.12 min | |
| cyclopentylmagnesium bromide | Ex. 120 | Ex. 140 |
| | 364.13(M − H), 1.41 min | 330.19(M − H), 1.26 min |
| Hexylmagnesium bromide | Ex. 121 | Ex. 141 |
| | 380.16(M − H), 1.50 min | 346.24(M − H), 1.38 min |
| | 380.17(M − H), 1.54 min | 346.24(M − H), 1.42 min |
| pentylmagnesium bromide | Ex. 122 | Ex. 142 |
| | 366.15(M − H), 1.42 min | 332.19(M − H), 1.30 min |
| | 366.16(M − H), 1.47 min | 332.19(M − H), 1.35 min |
| Butylmagnesium bromide | Ex. 123 | Ex. 143 |
| | 352.15(M − H), 1.34 min | 318.18(M − H), 1.26 min |
| | 352.13(M − H), 1.40 min | |
| isopropylmagnesium bromide | Ex. 124 | |
| | 338.11(M − H), 1.31 min | |
| o-tolylmagnesium bromide | | Ex. 144 |
| | | 352.16(M − H), 1.24 min |
| tert-butylmagnesium bromide | Ex. 125 | Ex. 145 |
| | 352.14(M − H), 1.41 min | 318.2(M − H), 1.28 min |
| isobutylmagnesium bromide | Ex. 126 | |
| | 352.14(M − H), 1.33 min | |
| | 352.13(M − H), 1.38 min | |
| vinylmagnesium bromide | Ex. 127 | Ex. 146 |
| | 322.09(M − H), 1.14 min | 288.15(M − H), 0.98 min |
| | 322.10(M − H), 1.19 min | 288.15(M − H), 1.02 min |
| allylmagnesium bromide | Ex. 128 | Ex. 147 |
| | 336.11(M − H), 1.22 min | 302.17(M − H), 1.06 min |
| | 336.12(M − H), 1.27 min | 302.17(M − H), 1.11 min |
| ethylmagnesium bromide | Ex. 129 | Ex. 148 |
| | 324.10(M − H), 1.18 min | 290.18(M − H), 1.01 min |
| | 324.11(M − H), 1.22 min | 290.17(M − H), 1.06 min |
| 4-chlorophenylmagnesium bromide | Ex. 131 | |
| | 406.06(M − H), 1.36 min | |
| | 406.06(M − H), 1.41 min | |
| 2-methyl-1-propenylmagnesium bromide | Ex. 132 | |
| | 350.13(M − H), 1.25 min | |
| | 350.10(M − H), 1.31 min | |

TABLE 13-continued (LCMS Data: Molecular ion and retention time)

| R—MgBr | 5-chlorothiophene | thiophene |
|---|---|---|
| isopropenylmagnesium bromide | Ex. 133 | |
| | 336.11(M − H), 1.25 min | |
| | 336.10(M − H), 1.28 min | |
| 4-anisylmagnesium bromide | Ex. 134 | Ex. 149 |
| | 402.13(M − H), 1.25 min | 368.16(M − H), 1.14 min |
| | 402.12(M − H), 1.31 min | 368.16(M − H), 1.16 min |
| 1-methyl-1-propenylmagnesium bromide | Ex. 135 | |
| | 350.13(M − H), 1.27 min | |
| | 350.12(M − H), 1.35 min | |
| 2-[2-(1,3-dioxanyl)]ethylmagnesium bromide | Ex. 136 | Ex. 150 |
| | 410.15(M − H), 1.15 min | 376.19(M − H), 0.98 min |
| 3-butenylmagnesium bromide | Ex. 137 | Ex. 151 |
| | 350.11(M − H), 1.30 min | 316.17(M − H), 1.15 min |
| | 350.12(M − H), 1.33 min | 316.17(M − H), 1.18 min |
| 1-propynylmagnesium bromide | | Ex. 152 |
| | | 300.17(M − H), 1.20 min |
| | | (M − H), min |
| 4-thioanisolemagnesium bromide | Ex. 138 | Ex. 153 |
| | 418.11(M − H), 1.35 min | 384.13(M − H), 1.26 min |
| | 418.11(M − H), 1.39 min | (M − H), min |
| 4-N,N-dimethylanilunemagriesium bromide | Ex. 139 | Ex. 154 |
| | 415.15(M − H), 0.89 min | 381.21(M − H), 0.68 min |
| | 415.17(M − H), 0.93 min | 381.21(M − H), 0.71 min |

Example 155

5-Chloro-N-{(S,S)-1-[(S)-cyclohex-2-en-1-yl(hydroxy)methyl]-2-methylbutyl}thiophene-2-sulfonamide

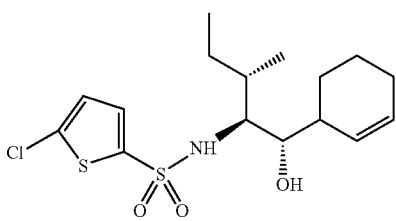

To a two dram vial containing magnesium turnings (60 mg, 2.5 mmol) suspended in THF (3 mL) was added 2-bromocyclohexene (288 µL, 2.5 mmol) followed by 5-chlorothiophene-2-sulfonyl isoleucinal (1 mL of a 1 M THF solution, 1 mmol, example 118). The vial was capped and agitated at 50° C. for 18 h. The vial was cooled and sat. aqueous $NH_4Cl$ (1 mL) was added. The vial was vortexed and the organic layer was transferred into a tarred vial and the aqueous layer was extracted with EtOAc (1 mL). The combined organics were concentrated in vacuo and the residue was submitted to semipreparative RP-HPLC using the conditions below.

Semi-preparative RP-HPLC conditions.
Column: Spring Axial compression; Kromasil C18 10 µm particle size; 50×150 mm
Solvent A: Water (0.1% TFA)
Solvent B: Acetonitrile
Solvent Gradient: 15-95% over 24 min, full cycle is 35 min
Flow Rate: 60 ml/min
The product peak was collected based on UV (or ELSD) absorption.

The following compounds (Examples 155-161, Table 14) were prepared using 2-bromocyclohexene, crotyl bromide, 1-bromo-2-pentene, 3-bromo-2-methylpropene, and cinnamyl bromide following the procedure outlined in Example 155.

TABLE 14

(LCMS Data: Molecular ion and retention time)

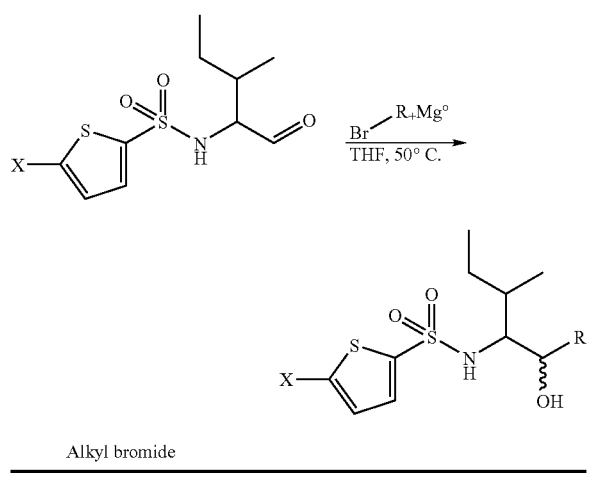

| Alkyl bromide | | |
|---|---|---|
| 2-bromocyclohexene | Example 155 | 376.70(M − H), 1.27 min |
| crotyl bromide | Example 156 | 350.50(M − H), 1.22 min |
| crotyl bromide | Example 157 | 350.70(M − H), 1.25 min |
| 1-bromo-2-pentene | Example 158 | 364.60(M − H), 1.35 min |
| 3-bromo-2-methylpropene | Example 159 | 350.60(M − H), 1.20 min |
| 3-bromo-2-methylpropene | Example 160 | 350.60(M − H), 1.24 min |
| cinnamyl bromide | Example 161 | 412.60(M − H), 1.34 min |

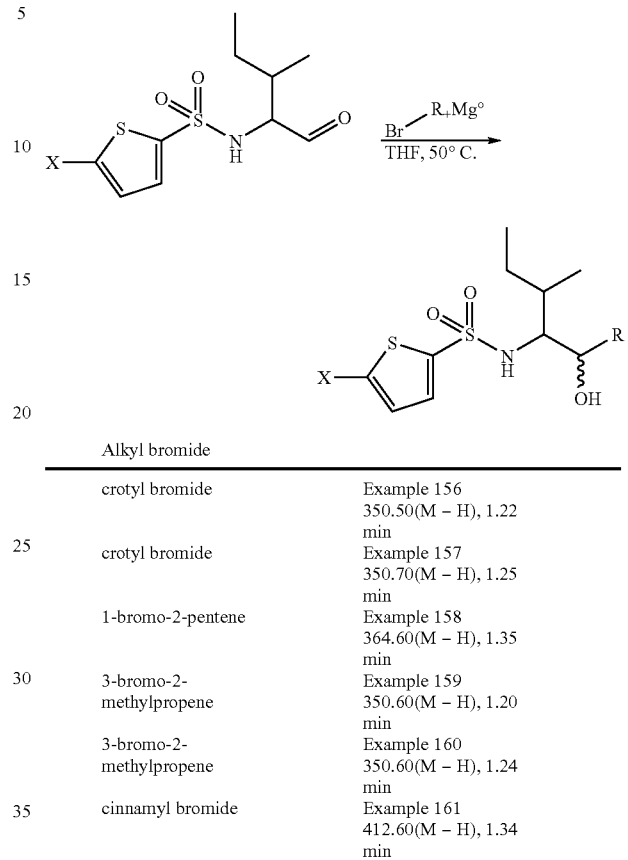

Example 162

5-Chloro-N-[(S,S)-1-(1-hydroxy-1-methylethyl)-2-methylbutyl]thiophene-2-sulfonamide

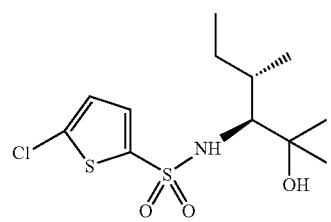

A. Part 1

To a solution of 5-chlorothiophene-2-sulfonyl chloride (1.09 g, 5 mmol) in $CH_3CN$ (20 mL) was added (L)-isoleucine methyl ester hydrochloride (908.5 mg, 5 mmol) as a solution in $CH_3CN$ (10 mL) and $Et_3N$ (1 mL, 7.2 mmol). The reaction mixture was heated at 50° C. with shaking for 3 days. The solvent was removed and the oil was dissolved in EtOAc (10 mL). The solution was washed with water (5 mL), sat. $NH_4OH$ (5 mL), and brine (5 mL), and dried over $MgSO_4$. The solvent was removed to give 1.44 g (88%) of the desired sulfonamide.

B. Part 2

To a solution of the ester from part 1 (40.7 mg, 0.125 mmol) in THF (500 µL) was added methyl magnesium bromide (333 µL, 3.0 M in THF, 8 eq). The vial was capped and agitated at 50° C. for 12 h. The reaction was quenched with sat. aqueous NH₄Cl (1.5 mL) and EtOAc (1 mL). The organic layer was transferred into a tarred vial and the aqueous layer was extracted with EtOAc (1 mL). The combined organics were concentrated (Savant, medium heat) and the product was dissolved in DMSO such that the final concentration was 30 mM.

The following compounds (Examples 162-176, Table 15) were prepared using 5-chlorothiophene-2-sulfonyl isoleucine methyl ester and 5-bromothiophene-2-sulfonyl isoleucine methyl ester (from part 2) with methylmagnesium bromide, pentylmagnesium bromide, phenylmagnesium bromide, allylmagnesium bromide, ethylmagnesium bromide, 4-chlorophenylmagnesium bromide, isopropenylmagnesium bromide, 4-anisylmagnesium bromide, 1-methyl-1-propenylmagnesium bromide, 3-butenylmagnesium bromide, 1-propynylmagnesium bromide, 1-naphthylmagnesium bromide following the procedure outlined in example 162.

TABLE 15

(LCMS Data: Molecular ion and retention time)

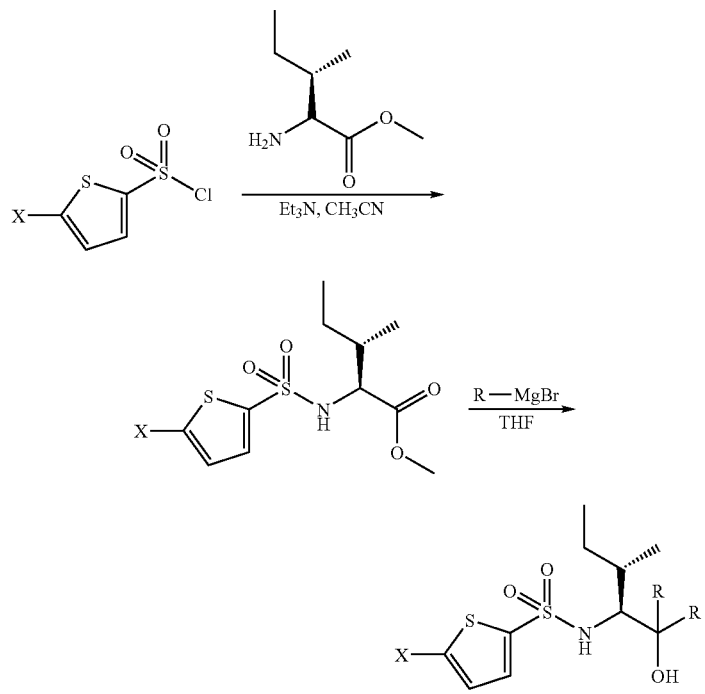

| R—MgBr | X = Cl | X = Br |
|---|---|---|
| methylmagnesium bromide | Example 162<br>324.58(M − H), 1.19 min | |
| pentylmagnesium bromide | Example 163<br>436.69(M − H), 1.79 min | |
| phenylmagnesium bromide | Example 164<br>448.60(M − H), 1.50 min | |
| Allylmagnesium bromide | Example 165<br>376.58(M − H), 1.44 min | |
| ethylmagnesium bromide | Example 166<br>352.63(M − H), 1.39 min | Example 173<br>395.49(M − H), 1.45 min |
| 4-chlorophenylmagnesium bromide | Example 167<br>516.49(M − H), 1.62 min | |
| isopropenylmagnesium bromide | Example 168<br>376.60(M − H), 1.51 min | Example 174<br>421.29(M − H), 1.39 min |
| 4-anisylmagnesium bromide | Example 169<br>508.59(M − H), 1.45 min | |

TABLE 15-continued (LCMS Data: Molecular ion and retention time)

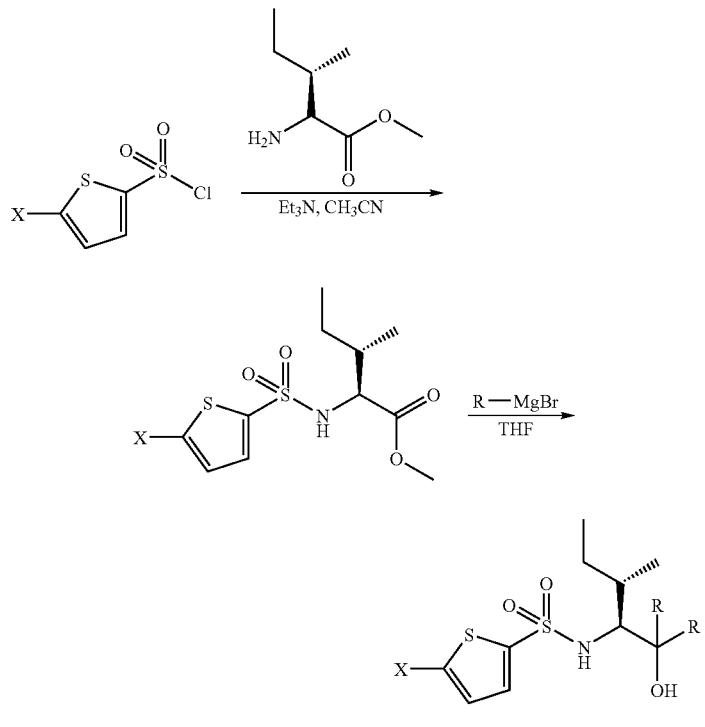

| R—MgBr | X = Cl | X = Br |
|---|---|---|
| 1-methyl-1-propenylmagnesium bromide | Example 170<br>404.61(M − H), 1.65 min | Example 175<br>447.46(M − H), 1.52 min |
| 3-butenylmagnesium bromide | Example 171<br>404.64(M − H), 1.54 min | Example 176<br>447.25(M − H), 1.26 min |
| 1-naphthylmagnesium bromide | Example 172<br>548.56(M − H), 1.64 min | |

Example 177

5-Chloro-N-[1-(hydroxymethyl)cyclohexyl]thiophene-2-sulfonamide

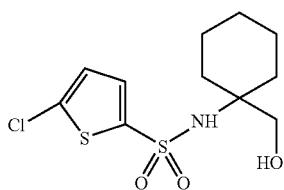

A. Part 1

To a suspension of 1-amino-1-cyclohexane carboxylic acid (5 g, 35 mmol) and THF (100 mL) was added borane dimethyl sulfide (50 mL, 2M in THF) at 0° C. The cold bath was allowed to expire and the reaction was stirred at 25° C. overnight. NaOH (3M, 100 mL) was added and the mixture was stirred for 4 h. The reaction mixture was saturated with $K_2CO_3$ and extracted with $Et_2O$ (2×100 mL). The combined organics were washed with brine (100 mL) and dried over $MgSO_4$ to give 4.35 g (96%) of the desired amino alcohol.

B. Part 2

The amino alcohol was sulfonylated as in Example 89.

The following compounds (Examples 177-183, Table 16) were prepared using the amino alcohols of 1-amino-1-cyclohexane carboxylic acid, 2-amino-2-norbornane carboxylic acid, D,L-1-aminoindane-1-carboxylic acid, and 2-aminoindane-2-carboxylic acid hydrochloride with 5-chlororothiophene-2-sulfonyl chloride and 5-bromothiophene-2-sulfonyl chloride following the procedure outlined for Example 177.

TABLE 16

(LCMS Data: Molecular ion and retention time)

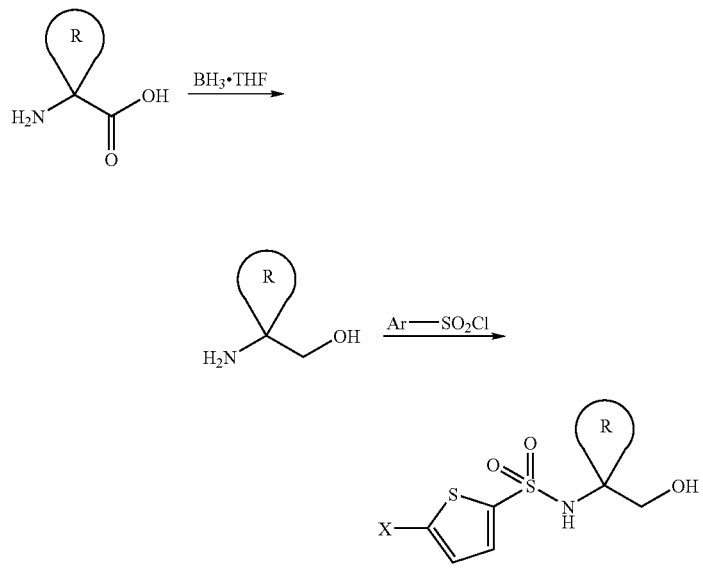

| Aminoacid | X = Cl | X = Br |
| --- | --- | --- |
| 1-amino-1-cyclohexane carboxylic acid | Example 177<br>308.14(M − H), 1.00 min | Example 181<br>353.99(M − H), 1.02 min |
| 2-amino-2-norbornane carboxylic acid | Example 178<br>320.13(M − H), 1.04 min | Example 182<br>366.03(M − H), 1.06 min |
| D,L-1-aminoindane-1-carboxylic acid | Example 179<br>342.12(M − H), 1.09 min | |
| 2-aminoindane-2-carboxylic acid HCl | Example 180<br>342.12(M − H), 1.07 min | Example 183<br>388.01(M − H), 1.08 min |

The following compounds (Examples 184-195, Table 17) were synthesized using 5-chlorothiophene-2-sulfonyl isoleucinal and 5-bromothiophene-2-sulfonyl isoleucinal with methylmagnesium bromide, n-propylmagnesium chloride, and allylmagnesium bromide following the procedure outlined for example 119. The resulting mixtures of diastereomers were isolated by semi-preparative RP-HPLC using the conditions outlined for example 155.

TABLE 17

(LCMS Data[3]: Molecular ion and retention time)

| R-MgX | X = Cl | X = Br |
| --- | --- | --- |
| methylmagnesium bromide | Example 184<br>310.41 (M-H), 0.87 min | Example 190<br>356.20 (M-H), 0.95 min |
| | Example 185<br>310.44 (M-H), 0.93 min | Example 191<br>356.15 (M-H), 1.02 min |
| n-propylmagnesium chloride | Example 186<br>338.47 (M-H), 1.06 min | Example 192<br>384.17 (M-H), 1.13 min |
| | Example 187<br>338.45 (M-H), 1.12 min | Example 193<br>384.24 (M-H), 1.18 min |
| allylmagnesium bromide | Example 188<br>336.10 (M-H), 1.2 min | Example 194<br>382.00 (M-H), 1.2 min |
| | Example 189<br>336.10 (M-H), 1.24 min | Example 195<br>382.00 (M-H), 1.25 min |

The pure synthetic diastereomer of Example 189 was prepared as follows.

A. Part 1

To a −78° C. solution of the Weinreb amide (see: F. Roux, et. Al. *Tetrahedron*, 1994, 50 (18), 5345-5360) of BOC-protected isoleucine (13.17 g, 48 mmol) was added allylmagnesium bromide (90 mL, 1M in THF). The cold bath was allowed to expire and the reaction stirred at 25° C. overnight. The reaction was quenched by the addition of cold aq. HCl (150 mL, 1M). After 30 min of stirring, the layers were separated and the aqueous layer extracted with ethyl acetate (3×75 mL). The combined organics were dried over MgSO$_4$ and the solvent removed to give 8.41 g (69%) of the desired ketone.

B. Part 2

To a solution of the ketone from part 1 (8.4 g) in MeOH (200 mL) was added NaBH$_4$ (1.5 g, 39.6 mmol) as a solid. The reaction was stirred at 25° C. for 5 h at which time the solvent was removed in vacuo. The residue was dissolved in ethyl acetate (100 mL) and washed with water (2×50 mL). The crude product was subjected to a Biotage™ eluting with 5 to 15% EtOAc/hexane to give 4.12 g (49%) of the desired alcohol.

C. Part 3

A solution of alcohol from part 2 (4.12 g, 16 mmol), $CH_2Cl_2$ (75 mL), and TFA (15 mL) was stirred at 25° C. for 15 min. The reaction was quenched with a solution of NaOH (15 mL, 1 M) and then basified to pH 12 with NaOH pellets. The resulting solution was extracted with $CH_2Cl_2$ (2×50 mL), and the combined organics were washed with water (25 mL), brine (25 mL), and dried over $MgSO_4$ to give 2.44 g (97%) of the desired amino alcohol, which was carried on to part 4 without further purification.

D. Part 4

The amino alcohol was sulfonylated as in example 89. The pure synthetic diastereomer of Example 193 was obtained as follows:

To a solution of the BOC-amino homoallyl alcohol (1.1 g, 4.27 mmol, see part 1-2 of example 188) in absolute EtOH (50 mL) was added Pd/C (110 mg). The flask was placed under an atmosphere of hydrogen (balloon) and stirred at 25° C. Following completion of the reaction (2 h), the mixture was filtered through a pad of Celite and the solvent was removed to give 1.16 g (quant) of the propyl analog. The BOC group was removed and the amine sulfonylated per the protocol outlined-for example 189.

Example 196

5-Chloro-N-[(S,S)-2-methyl-1-(2,2,2-trifluoro-1-hydroxyethyl)butyl]thiophene-2-sulfonamide

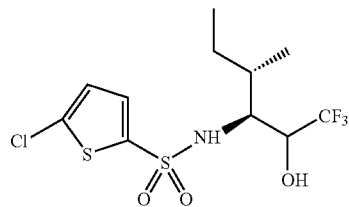

To a 0° C. solution of 5-chlorothiophene-2-sulfonyl isoleucinal (770 mg, 2.6 mmol, see Example 118, parts 1&2) in THF (5 mL) was added TMS-$CF_3$ (5 mL, 0.5M in THF). The resulting mixture was treated with TBAF (250 µL, 1M in THF). The cold bath was removed and the reaction was stirred at 25° C. overnight. The reaction was quenched with HCl (25 mL, 2M) and the resulting solution was extracted with ethyl acetate (3×15 mL). The combined organic extracts were washed with water (25 mL) and brine (25 mL) then dried over $MgSO_4$. The residue was submitted to RP-HPLC (see example 155 for procedure) to give 74 mg of the desired product (m/z=364.0 (M–H), rt=1.23 min).

The following compounds (Examples 197-198, Table 18) were synthesized using 1-amino-1-cyclohexane carboxylic acid and 5-chlorothiophene-2-sulfonyl chloride with allylmagnesium bromide and 2-methyl allylmagnesium chloride following the four step procedure outlined for examples 177 (parts 1&2), 118 (part 2), and 119 respectively.

TABLE 18

(LCMS Data: Molecular ion and retention time)

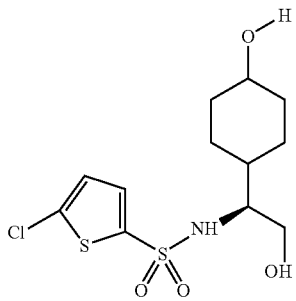

| R—MgX | |
|---|---|
| allylmagnesium bromide | Example 197<br>348.10(M – H), 1.18 min |
| 2-methylallylmagnesium chloride | Example 198<br>364.10(M – H), 1.26 min |

Example 199A

5-Chloro-N-[(S)-2-hydroxy-1-(4-hydroxycyclohexyl)ethyl]thiophene-2-sulfonamide

A. Part 1

To a solution of 4-hydroxy-L-phenylglycine (10 g, 60 mmole) in NaOH (20 mL, 3M) was added water (380 mL) and Raney nickel (30 g). The reaction mixture was hydrogenated at about 3 atm at 60 to 80° C. for 36 h in a hydrogen bomb. The reaction mixture was filtered through Celite and reduced in volume to about 80-100 mL and dioxane (100 mL) was added. The resulting mixture was cooled to 0° C. and treated with $Et_3N$ (10 mL) and 5-chlorothiophene-2-sulfonyl chloride (16 g, 72 mmoles). The reaction was allowed to warm up to 25° C. and stirred overnight. The dioxane and $Et_3N$ were removed and the remaining aqueous solution diluted with 1N aq. HCl. The resulting precipitate was collected, washed with water and diethyl ether to give the desired product as a white solid (12 g, 50% in two steps) (100% purity by ELSD, m/z=352 (M–1)).

B. Part 2

To a suspension of (S)-N-(5-Cl-thiophene-2-sulfonyl)-4-hydroxycyclohexylglycine (12 g, 33.99 mmol, part 1) in anhydrous THF was added borane-THF (110 mL, 1 M in THF, 110 mmoles) dropwise at 0° C. The resulting mixture was stirred at 25° C. over the weekend. The reaction mixture was quenched with HCl (75 mL, 1M) at 0° C. and stirred at 25° C. for 1 h. THF was removed and the precipitate was collected, washed with water (containing a small amount of diethyl ether), and dried to give a white solid as the desired product (9 g, 78%) (100% purity by ELSD, m/z=338.5 (M−1), HPLC retention time[3]=0.64 min).

Example 199

5-Chloro-N-[(S)-2-hydroxy-1-(4-methoxycyclo-hexyl)ethyl]thiophene-2-sulfonamide

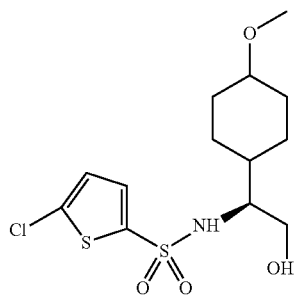

A. Part 1

A mixture of 5-chloro-N-[(S)-2-hydroxy-1-(4-hydroxycyclohexyl)ethyl]thiophene-2-sulfonamide (6.4 g, 18.83 mmol) from Example 199A, 2,2-dimethoxypropane (7 mL, 5.65 mmol), and TsOH H$_2$O (72 mg, 0.38 mmol.) in anhydrous benzene (120 mL) was refluxed. After one hour, benzene was slowly distilled under atmospheric pressure to a final volume of 10 mL. Fresh benzene (100 mL) and 2,2-dimethoxypropane (5 mL) were added and the above operation was repeated. The residue was partitioned between diethyl ether and sat. NaHCO$_3$. The aqueous layer was extracted with diethyl ether (3×100 mL), and the combined extracts were dried over MgSO$_4$. The crude product was purified by column chromatography using 1:5 EtOAc/CH$_2$Cl$_2$ as an eluent to give the N,O-acetonide (5.77 g, 81%) (100%, m/z=380 (M+1)).

B. Part 2

To a 0° C. solution of (S)-2-(5-Cl-thiophene-2-sulfonamido)-2-(4-hydroxycyclohexyl)-N,O-acetonide (379 mg, 1 mmol) in THF (7 mL) and DMF (2 mL) was added NaH (80 mg, 2 mmol). The resulting reaction was stirred at 0° C. for 10 min at which time iodomethane (311 μL, 5 mmol) was added. The reaction was allowed to warm to 25° C. and stirred for 18 h. The solvent was removed and acetic acid (80%, 15 mL) was added. The mixture was stirred at 25° C. over the weekend. Following removal of the acetic acid in vacuo, the residue was subjected to column chromatography on silica gel eluting with MeOH/CH$_2$Cl$_2$ (3:10) to give 303 mg (86%) of the desired product.

The following compounds (Examples 199-202B, Table 19) were prepared using (S)-2-(5-Cl-thiophenesulfonamido)-2-(4-hydroxycylohexyl)-N,O-acetonide (from Example 199, part 1) with iodomethane, 1-bromopropane, allyl bromide, benzyl bromide, 2-picolyl chloride hydrochloride and 3-picolyl chloride hydrochloride as outlined in Example 199.

TABLE 19

(LCMS Data[3]: Molecular ion and retention time)

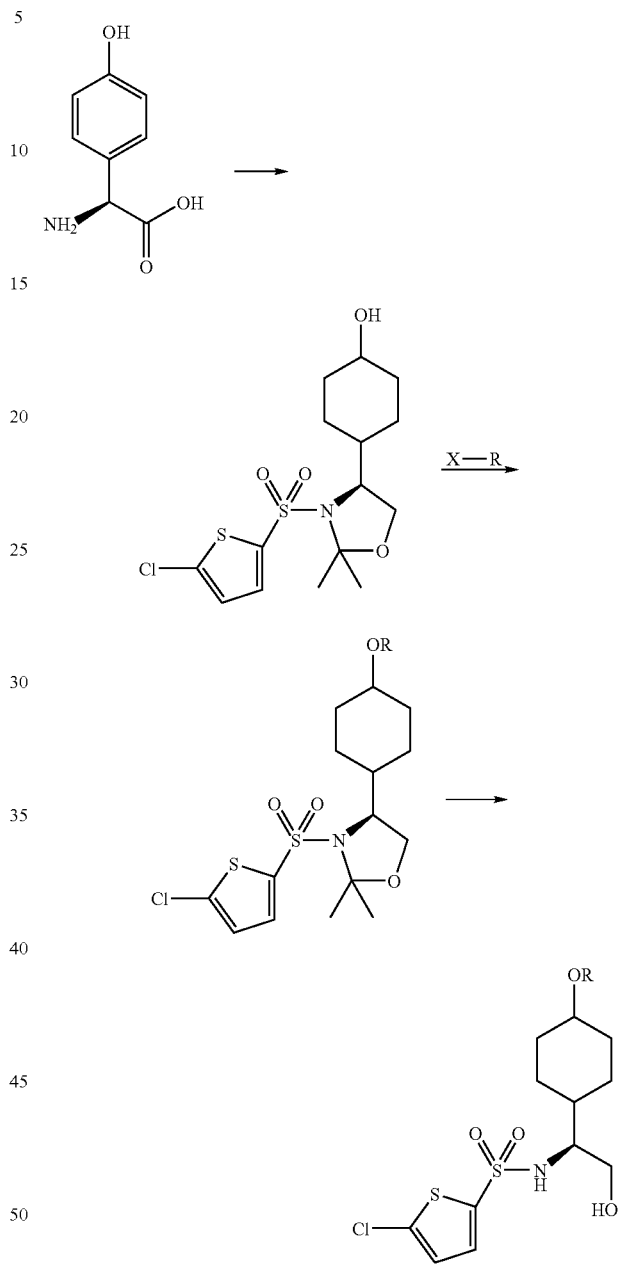

| R—X | |
|---|---|
| iodomethane | Example 199 |
| | 352.1(M − H), 0.82 min |
| 1-bromopropane | Example 200 |
| | 366.0(M − H), 0.91 min |
| allyl bromide | Example 201 |
| | 378.0(M − H), 1.01 min |
| benzyl bromide | Example 202 |
| | 428.1(M − H), 1.21 min |
| 2-picolyl chloride HCl | Example 202A |
| | 429.4(M − H), 0.57 min |
| 3-picolyl chloride HCl | Example 202B |
| | 429.0(M − H), 0.57 min |

Example 203

N-[1-Acetyl-4-(hydroxymethyl)piperidin-4-yl]-5-chlorothiophene-2-sulfonamide

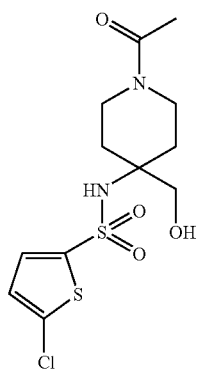

A. N-[1-Boc-4-(Carboxylic acid)piperidin-4-yl]-5-chlorothiophene-sulfonamide

Triethylamine (2.28 mL, 1.66 g, 16.45 mmol) was added to a slurry of 1-Boc-4-aminopiperidine-4-carboxylic acid (2.68 g, 10.973 mmole) in acetonitrile:water (1:1) (40 mL) at 25° C. The slurry became a neon yellow to greenish solution at the end of addition. The slurry was slightly warmed up (5 min) in order to obtain a solution. The mixture was cooled to 0° C., 5-chlorothiophene-2-sulphonyl chloride (2.62 g, 12.07 mmol) was added (5 min) dropwise as a solution in acetonitrile (8 mL). The solution was allowed to warm up to 25° C. overnight. After 19 h, an aliquot was taken. TLC (9:1 $CH_2Cl_2$:$CH_3OH$) indicated that reaction was about 90% done. The reaction was quenched by addition of water (50 mL), $CH_2Cl_2$ (50 mL) and ice cold 1N HCl (10 mL). The organic layer was washed with water and saturated NaCl. It was dried over $MgSO_4$, filtered, and concentrated to a yellow oil (2.1 g). The crude material was purified by column chromatography, silica gel 230 to 400 mesh, eluent: starting with 5% MeOH in $CH_2Cl_2$ and ending with 10% MeOH in $CH_2Cl_2$ to furnish N-[1-Boc-4-(carboxylic acid)piperidin-4-yl]-5-chlorothiophene-2-sulfonamide as a white amorphous solid (1.2 g, 25.7%). Mass Spectrum (−ESI): 423 (M−H)$^-$.

B. N-[1-Boc-4-(hydroxymethyl)piperidin-4-yl]-5-chlorothiophene-2-sulfonamide

1N Borane-THF (1.019 g, 12.14 mL, 11.86 mmol) was added dropwise over 30 min at 0° C. to a solution of N-[1-Boc-4-(carboxylic acid)piperidin-4-yl]-5-chlorothiophene-2-sulfonamide (1.2 g, 2.82 mmol) in anhydrous tetrahydrofuran (15 mL). The reaction was allowed to warm up to 25° C. overnight, and then was quenched by addition of 30 mL of 10% acetic acid in methanol. After solvent evaporation, the crude product was dissolved in ethyl acetate and washed with 1M HCl, water and 10% $NaHCO_3$. The organic layer was dried over $MgSO_4$, filtered and concentrated to obtain a crude yellow oil (1.1 g). The crude product was purified by column chromatography, silica gel 230-400 mesh, eluent: starting with 1:3 EtOAc-hexane and ending with 1:1 EtOAc-hexane to afford N-[1-Boc-4-(hydroxymethyl)piperidin-4-yl]-5-chlorothiophene-2-sulfonamide as a colorless oil (0.79 g, 68.2%). Mass Spectrum (−ESI): 409 (M−H)$^-$.

C. N-[4-(Hydroxymethyl)piperidin-4-yl]-5-chlorothiophene-2-sulfonamide HCl Salt

4N HCl (5 mL) was added to a stirred solution of N-[1-Boc-4-(hydroxymethyl)piperidin-4-yl]-5-chlorothiophene-2-sulfonamide 5 (0.7 g, 1.7 mmol) in EtOAc (4 mL). The solution was allowed to stir at 25° C. After 30 min, a cloudy solution formed. After 2 h a precipitate formed. TLC (1:1 EtOAc-hexane) indicated the reaction was complete. The solvent was reduced to ~2-3 mL, diluted with diethyl ether (6 mL) and filtered through a filter funnel. The precipitate was washed with diethyl ether (3×5 mL) to obtain N-[4-(hydroxymethyl)piperidin-4-yl]-5-chlorothiophene-2-sulfonamide as an amorphous white solid (0.48 g, 90.7%). Mass Spectrum (+ESI): 311 (M+H)$^+$.

D. N-[1-Acetyl-4-(hydroxymethyl)piperidin-4-yl]-5-chlorothiophene-2-sulfonamide

Acetyl chloride (0.15 g, 1.894 mmol) was added dropwise (5 min) as a solution in $CH_2Cl_2$ (1 mL) to a cold 0° C. solution of N-[4-(hydroxymethyl)piperidin-4-yl]-5-chlorothiophene-2-sulfonamide (0.19 g, 0.61 mmol) in $CH_2Cl_2$ (5 mL) and triethylamine (0.44 mL, 3.18 mmol) The solution was allowed to warm to 25° C. overnight (19 h). An aliquot was taken and TLC (1:1 EtOAc-hexane) indicated that reaction was complete. It was diluted with $CH_2Cl_2$ (10 mL) and the organic layer was washed with 1N HCl (50 mL), saturated aqueous $NaHCO_3$ (50 mL) and NaCl (50 mL). The organic layer was dried over $MgSO_4$, filtered, and concentrated to obtain a crude oil (175 mg). The crude product was purified by column chromatography, silica gel 230-400 mesh, eluent: starting with 1:4 EtOAc-hexane and ending with 1:1 EtOAc-hexane to afford N-[1-Acetyl-4-(hydroxymethyl)-piperidin-4-yl]-5-chlorothiophene-2-sulfonamide as yellowish color oil (62 mg, 28.9%). Mass Spectrum (+ESI): 353 (M+H)$^+$. Anal. Calc'd for $C_{12}H_{17}ClN_2O_4S_2 \cdot 1.62\ H_2O$: C, 37.29; H, 5.70; N, 7.26. Found: C, 37.62; H, 5.36; N, 7.31.

Example 204

5-Chloro-N-[(1S,2S)-1-(hydroxymethyl)-2-methylbutyl]-2-furansulfonamide

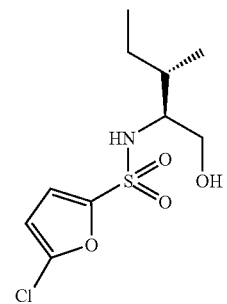

A. 2-Chlorofuran 1.6 M nBuLi (15.37 g, 150 mL, 0.24 mol) was added dropwise over 10 min at 25° C. to a solution of furan (13.6 g, 0.20 mol) in dry diethyl ether (200 mL). When the dropwise addition was completed, the reaction mixture was cooled to −70° C. At this temperature a solution of hexachloroethane (49.8 g, 0.21 mol) was added over 10 min and the temperature was not allowed to rise above −55° C. The reaction mixture was kept at −70° C. for 3 h. The reaction mixture was then warmed to 25° C., hydrolyzed with ice water and neutralized with 2.5 N hydrochloric acid. The phases were separated and the water phase extracted twice with diethyl ether (100 mL). The combined diethyl ether phases were washed once with a solution of NaHCO₃ (50 mL) and once with water (50 mL) and dried over MgSO₄. The diethyl ether was distilled off through a fractionating column and the product was collected at 78 to 79° C. to obtain 2-chlorofuran as a colorless oil (20.0 g, 97.6%). ¹H-NMR (DMSO-d₆, 400 MHz) δ 7.34 (d, 1H); 6.38 (d, 1 H); 6.21 (d, 1H).

B. 5-Chlorofuran-2-sulfonyl chloride

Phosphorus pentachloride (40.53 g, 0.1947 mol) was added portionwise (caution, foaming) over 5 min at 25° C. to chlorosulfonic acid (56.8 g, 32.4 mL, 0.487 mol) and the resulting solution was stirred at 25° C. for 10 min. Then, 2-chlorofuran (20.0 g, 20 0.1947 mol) was added in one portion and the resulting dark suspension was heated to 55° C. for 1.0 h during which time foaming occurred and subsided. The reaction mixture was then poured onto ice and the resulting suspension was extracted with CH₂Cl₂ (250 mL). The organic was filtered through a pad of celite, washed with brine (70 mL) and dried over MgSO₄. The solvent was removed in vacuo to provide 5-chlorofuran-2-sulfonyl chloride as a black oil (14.1 g, 36.02%). ¹H-NMR (DMSO-d₆, 400 MHz) δ 7.05 (d, 1H); 6.35 (d, 1 H).

C. 5-Chloro-N-[(1S,2S)-1-(hydroxymethyl)-2-methylbutyl]-2-furansulfonamide

5-Chlorofuran-2-sulfonyl chloride (3.376 g, 16.79 mmol) was added dropwise (5 min) as a solution in CH₂Cl₂ (10 mL) to a 0° C. solution of L-isoleucinol (1.5 g, 12.92 mmol) in CH₂Cl₂ (15 mL) and triethylamine (2.69 mL, 19.38 mmol). The solution was allowed to warm to 25° C. overnight (19 h). An aliquot was taken and TLC (1:1 EtOAc-hexane) indicated that reaction was complete. It was diluted with CH₂Cl₂ (100 mL) and the organic layer was washed with 1N HCl (2×50 mL), saturated aqueous NaCl (50 mL). The organic layer was dried over MgSO₄, filtered, and concentrated to obtain a crude black oil (2.69 g). The crude product was purified by column chromatography, silica gel 230 to 400 mesh, eluent: starting with 1:4 EtOAc-hexane and ending with 1:1 EtOAc-hexane to afford 5-chloro-N-[(1S,2S-1-(hydroxymethyl)-2-methylbutyl]-2-furansulfonamide as an amorphous white solid (0.98 g, 26.92%). Mass Spectrum (−ESI): 280 (M−H)⁻. Anal. Calc'd for C₁₀H₁₆ClN₂O₄S: C, 42.63; H, 5.72; N, 4.97. Found: C, 42.34; H, 5.65; N, 4.77.

Example 205

N-[(1S)-2-Butyl-1-(hydroxymethyl)hexyl]-5-chloro-2-thiophenesulfonamide

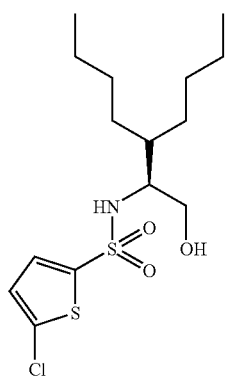

A. (4R)-4-Benzyl-3-[(E)-2-heptenoyl]-1,3-oxazolidin-2-one

Triethylamine (6.85 g, 49.15 mmol) and trimethyl acetyl chloride (6.05 mL, 49.15 mmol) were added dropwise (5 min) to a −78° C. solution of 2-heptenoic acid (6 g, 46.81 mmole) in THF (80 mL). The slurry was stirred at −78° C. for 5 min and then replaced with a 0° C. cooling system. It was stirred at this temperature for 1 h. In a separate flask, a solution of R-(+)-4-benzyl-2-oxazolidinone (8.295 g, 46.81 mmol) was cooled to −78° C. and nBuLi (1.6M, 46.8 mmol) was added dropwise over 10 min. The colorless solution was stirred at this temperature for 45 min and transferred via cannula to a −78° C. solution of the ester. The yellowish slurry was warmed to 25° C. overnight (19 h). An aliquot was taken and TLC (1:1 EtOAc-hexane) indicated that reaction was complete. It was cooled to 0° C. and the reaction was quenched by addition of H₂O (20 mL). It was diluted with ethyl acetate (200 mL) and the organic layer was separated. The organic layer was dried over MgSO₄, filtered, and concentrated to obtain a crude yellow oil (13.69 g). The crude product was purified by column chromatography, silica gel 230 to 400 mesh, eluent: 1:4 EtOAc-hexane to obtain (4R)-4-benzyl-3-[(E)-2-heptenoyl]-1,3-oxazolidin-2-one as a colorless oil (12.1 g, 92.80%). Mass Spectrum (−ESI): 288 (M−H)⁻.

B. (4R)-4-Benzyl-3-[(2R)-2-bromo-3-butylheptanoyl]-1,3-oxazolidin-2-one

A slurry of copper bromide (I) dimethyl sulfide complex (5.132 g, 24.967 mmol) in THF (60 mL) and dimethyl sulfide (30 mL) as a co-solvent was cooled to −40° C. and n-butyl magnesium chloride (25 mL, 49.93 mmol) was added dropwise for 10 min and stirred for 20 min while warming to −15° C. The black slurry was cooled to −40° C. and (4R)-4-benzyl-3-[(E)-2-heptenoyl]-1,3-oxazolidin-2-one (6 g, 20.80 mmol) was added dropwise over 10 min as a solution in THF (20 mL) at −40° C. The reaction was let warm up to 25° C. overnight (20 h). N-Bromosuccinimide (7.407 g, 41.61 mmol) was added portionwise to a cold −78° C. solution of the black slurry. It was allowed to warm to 0° C. and was stirred for an additional 3 h. The reaction was quenched with a 1:1 solution of saturated ammonium carbonate and 0.5 N potassium bisulfate. The black slurry became greenish to blue. A precipitate formed (light blue). It was filtered. The mother liquor was diluted with ethyl acetate (150 mL) and the organic was dried over MgSO₄, filtered, concentrated to obtain (4R)-4-benzyl-3-[(2R)-2-bromo-3-butylheptanoyl]-1,3-oxazolidin-2-one as a crude semi-solid (green) (8.49 g, 96.15%). Mass Spectrum (−ESI): 423 (M−H)⁻.

C. (4R)-3-[(2S)-2-Azido-3-butylheptanoyl]-4-benzyl-1,3-oxazolidin-2-one

Tetramethylguanidine azide (TMGA) (5.398 g, 37.70 mmol) was added dropwise (5 min) to a 25° C. solution of (4R)-4-benzyl-3-[(2R)-2-bromo-3-butylheptanoyl]-1,3-oxazolidin-2-one (4.0 g, 9.42 mmol) in acetonitrile (50 mL). The reaction was stirred for 4 days. An aliquot was taken and TLC (1:4 EtOAc-hexane) indicated that reaction was complete. The solvent was removed in vacuo. The resulting black semi-solid was dissolved in CH₂Cl₂ (200 mL) and quenched with 1N HCl (30 mL). The organic layer was dried over MgSO₄, filtered, and concentrated in vacuo to obtain (4R)-3-[(2S)-azido-3-butylheptanoyl]-4-benzyl-1,3-oxazolidin-2-one as a crude yellow oil (3.61 g, 99.1%). Mass Spectrum (−ESI): 385 (M−H)⁻.

D. (2S)-2-Amino-3-butyl-1-heptanol

To a slurry of LAH (1.219 g, 32.13 mmol) in THF (60 mL) was added (4R)-3-[(2S)-2-azido-3-butylheptanoyl]-4-benzyl-1,3-oxazolidin-2-one (3.6 g, 9.37 mmol) dropwise at 0° C. over 20 min. The reaction was heated to 36° C. for 18 h.

The reaction slurry (brown) was cooled to 0° C. and the reaction was quenched with H₂O (15 mL) and washed with 1N NaOH (30 mL) and H₂O (15 mL). It was let stir for 2 h to obtain an off-white slurry. The slurry was filtered and the mother liquor was further dried over MgSO₄, filtered, and concentrated in vacuo to obtain (2S)-2-amino-3-butyl-1-heptanol as a crude yellow oil (1.93 g, 73.75%). Mass Spectrum (+ESI): 188 (M+H)⁺.

E. N-[(1S)-2-Butyl-1-(hydroxymethyl)hexyl]-5-chloro-2-thiophenesulfonamide

5-Chlorothiophene-2-sulfonyl chloride (2.42 g, 11.55 mmol) was added dropwise (5 min) as a solution in CH₂Cl₂ (20 mL) to a 0° C. solution of (4R)-3-[(2S)-2-azido-3-butyl-heptanoyl]-4-benzyl-1,3-oxazolidin-one (1.9 g, 10.14 mmol) and triethylamine (2.11 mL, 15.21 mmol). The solution was allowed to warm to 25° C. overnight (19 h). An aliquot was taken and TLC (1:1 EtOAc-hexane) indicated that reaction was complete. It was diluted with CH₂Cl₂ (100 mL) and the organic layer was washed with 1N HCl (2×50 mL) and saturated aqueous NaCl (50 mL). The organic layer was dried over MgSO₄, filtered, and concentrated to obtain a crude oil (2.98 g). The crude product was purified by column chromatography, silica gel 230-400 mesh, eluent: starting with 1:3 EtOAc-hexane and ending with 1:2 EtOAc-hexane to furnish N-[(1S)-2-butyl-1-(hydroxymethyl)hexyl]-5-chloro-2-thiophenesulfonamide as an amorphous white solid (0.630 g, 16.9%). Mass Spectrum (−ESI): 366 (M−H)⁻. Anal. Calc'd for $C_{15}H_{25}NClO_3S_2$: C, 48.96; H, 7.12; N, 3.81. Found: C, 49.08, H, 6.83, N, 3.82.

Example 206

N-[(1S,2S)-1-(hydroxymethyl)-2-methylbutyl]-2-furansulfonamide

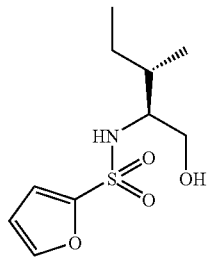

A. 2-Furansulfonyl chloride

Phosphorus pentachloride (15.29 g, 73.44 mmol) was added portionwise (caution, foaming) over 5 min at 0° C. to chlorosulfonic acid (21.39 g, 183.6 mmol) and the resulting solution was stirred at 0° C. for 10 min. Then, furan (5.0 g, 73.44 mmol) was added in one portion and the resulting dark suspension was stirred at 0° C. for 15 min during which time foaming occurred and subsided. The reaction mixture was then poured onto ice and the resulting suspension was extracted with CH₂Cl₂ (150 mL). The organic extract was filtered through a pad of celite, washed with brine and dried over MgSO₄. The solvent was removed in vacuo to provide 2-furansulfonyl chloride as a black oil (1.01 g, 7.9%). ¹H-NMR (DMSO-d₆, 400 MHz) δ 7.4 (d, 1H); 6.38 (d, 1H); 6.35 (d, 1 H).

B. N-[(1S,2S)-1-(Hydroxymethyl)-2-methylbutyl]-2-furansulfonamide

2-Furansulfonyl chloride (1.01 g, 8.69 mmol) was added dropwise (5 min) as a solution in CH₂Cl₂ (5 mL) to a 0° C. solution of L-isoleucinol (0.909 g, 7.83 mmol) in CH₂Cl₂ (20 mL) and triethylamine (2.42 mL, 17.38 mmol). The solution was allowed to warm to 25° C. overnight (19 h). An aliquot was taken and TLC (1:1 EtOAc-hexane) indicated that reaction was complete. It was diluted with CH₂Cl₂ (100 mL) and the organic layer was washed with 1N HCl (2×50 mL) and saturated aqueous NaCl (50 mL). The organic layer was dried over MgSO₄, filtered, and concentrated to obtain a crude black oil (0.65 g). The crude product was purified by column chromatography, silica gel 230-400 mesh, eluent: starting with 1:3 EtOAc-hexane and ending with 1:2 EtOAc-hexane to furnish N-[(1S,2S)-1-(hydroxymethyl)-2-methylbutyl]-2-furansulfonamide as an amorphous white solid (0.155 g, 72.12%).

Mass Spectrum (−ESI): 246 (M−H)⁻. Anal. Calc'd for $C_{10}H_{17}ClNO_4S$: C, 48.57; H, 6.93; N, 5.66. Found: C, 48.72; H, 6.78; N, 5.39.

Example 207

N-[(1S,2S)-1-(Hydroxymethyl)-2-methylbutyl]-5-iodo-2-thiophenesulfonamide

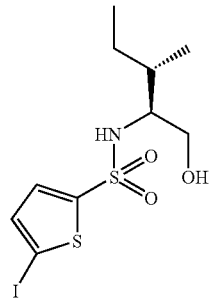

A. 5-Bromo-N-[(1S,2S)-1-(hydroxymethyl)-2-methylbutyl]-2-thiophenesulfonamide

5-Bromothiophene-2-sulfonyl chloride (5.0 g, 19.11 mmol) was added dropwise (5 min) as a solution in CH₂Cl₂ (10 mL) to a 0° C. solution of L-isoleucinol (2.108 g, 18.16 mmol) in CH₂Cl₂ (15 mL) and triethylamine (3.77 mL, 27.24 mmol). The solution was allowed to warm to 25° C. overnight (19 h). An aliquot was taken and TLC (1:1 EtOAc-hexane) indicated that reaction was complete. It was diluted in methylene chloride (100 mL) and the organic layer was washed with 1N HCl (2×50 mL) and saturated aqueous NaCl (50 mL). The organic layer was dried over MgSO₄, filtered, and concentrated to obtain a crude off-yellow solid (5.2 g). The crude product was purified by column chromatography, silica gel 230-400 mesh, eluent: starting with 1:4 EtOAc-hexane and ending with 1:1 EtOAc-hexane to furnish 5-bromo-N-[(1S,2S)-1-(hydroxymethyl)-2-methylbutyl]-2-thiophene-sulfonamide as an amorphous white solid (4.3 g, 70.49%). Mass Spectrum (−ESI): 246 (M−H)⁻.

B. N-[(1S,2S)-1-(Hydroxymethyl)-2-methylbutyl]-5-(tributylstannyl)-2-thiophenesulfonamide Bis(Tributyltin) (9.28 mL, 18.52 mmol) and tetrakis(triphenyl phosphine)palladium (0) (0.7133 g, 0.617 mmol) were added to a solution of 5-bromo-N-[(1S,2S)-1-(hydroxymethyl)-2-methylbutyl]-2-thiophenesulfonamide (4.2 g, 12.34 mmol) in 1,4-dioxane (42 mL). The brown solution was heated to reflux overnight (19 h). An aliquot was taken and TLC (1:1 EtOAc-hexane) indicated that reaction was complete. The slurry was then filtered and the solvent removed in vacuo to obtain a crude yellow oil (2.1 g). The crude product was purified by column chromatography, silica gel 230-400 mesh, eluent: 1:2 EtOAc-hexane to furnish N-[(1S,2S)-1-(hydroxymethyl)-2-methylbutyl]-5-(tributylstannyl)-2-thiophene sulfonamide as a yellow oil (0.88 g, 12.9%). Mass Spectrum (–ESI): 551 (M–H)$^-$.

C. N-[(1S,2S)-1-(Hydroxymethyl)-2-methylbutyl]-5-iodo-2-thiophenesulfonamide

To a solution of N-[(1S,2S)-1-(hydroxymethyl)-2-methylbutyl]-5-(tributylstannyl)-2-thiophene sulfonamide (0.35 g, 0.633 mmol) in methanol (4 mL) was added sequentially sodium acetate (0.104 g, 1.27 mmol), sodium iodide (0.190 g, 1.27 mmol in H$_2$O) and Chloramine T trihydrate (0.36 g, 1.27 mmol in methanol (0.5 mL)). The light-yellow solution turned red to orange upon addition of Chloramine T. The reacted was stirred at 25° C. for 2 h and then quenched by addition of 1M sodium bisulfite (10 mL). After addition of H$_2$O (10 mL), the aqueous layer was washed with diethyl ether (3×50 mL). The organic layer was dried over MgSO$_4$, filtered, concentrated to obtain a light yellow oil (0.210 g). The crude product was purified by HPLC (sil(25×0.46 cm); flow rate, 1.0 mL/min; eluent, 6% MTBE in CH$_2$Cl$_2$) to furnish N-[(1S,2S)-1-(hydroxymethyl)-2-methylbutyl]-5-iodo-2-thiophenesulfonamide as a white amorphous solid (0.125 g, 51.02%). Mass Spectrum (–ESI): 388 (M–H)$^-$. Anal. Calc'd for C$_{11}$H$_{17}$NIO$_4$S$_2$.0.07 EtOAc: C, 31.58; H, 4.21; N, 3.64. Found: C, 31.22; H, 4.22; N, 3.54.

Example 208

5-Fluoro-N-[(1S,2S)-1-(hydroxymethyl)-2-methylbutyl]-2-thiophenesulfonamide

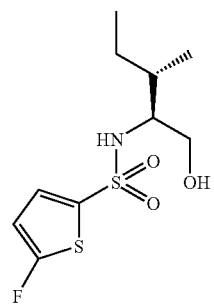

A. N-[(1S,2S)-1-(Hydroxymethyl)-2-methylbutyl]-5-(trimethylstannyl)-2-thiophenesulfonamide Hexamethylditin (5.055 g, 15.43 mmol) and tetrakis(triphenyl phosphine)palladium (0) (0.7133 g, 0.617 mmol) were added to a solution of 5-bromo-N-[(1S,2S)-1-(hydroxymethyl)-2-methylbutyl]-2-thiophenesulfonamide (prepared as in Example 199, Part A) (3.5 g, 10.27 mmol) in 1,4-dioxane (70 mL). The brown solution was heated to reflux overnight (19 h). An aliquot was taken and TLC (1:1 EtOAc-hexane) indicated that reaction was complete. The slurry was then filtered and the solvent removed in vacuo to obtain a crude yellow oil (2.1 g). The crude product was purified by column chromatography, silica gel 230-400 mesh, eluent: 1:2 EtOAc-hexane to obtain N-[(1S,2S)-1-(hydroxymethyl)-2-methyl-butyl]-5-(trimethylstannyl)-2-thiophenesulfon-amide as a yellow oil (3.1 g, 70.8%). Mass Spectrum (–ESI): 425 (M–H)$^-$. Anal. Calc'd for C$_{11}$H$_{17}$NIO$_4$S$_2$: C, 36.64; H, 5.91; N, 3.29. Found: C, 36.64; H, 5.81; N, 3.21.

B. 5-Fluoro-N-[(1S,2S)-1-(hydroxymethyl)-2-methylbutyl]-2-thiophenesulfonamide

A solution of N-[(1S,2S)-1-(hydroxymethyl)-2-methylbutyl]-5-(trimethylstannyl)-2-thiophene sulfonamide (1.0 g, 2.34 mmol) in dry acetonitrile (20 mL) was stirred under nitrogen at 25° C. Selectfluor (0.850 g, 2.40 mL) was added in one portion and the solution stirred for 19 h at 25° C. After 3 h a white precipitate began to appear. An aliquot was taken and TLC (1:1 EtOAc-hexane) indicated that reaction was not complete. Mainly, starting material was present. The reaction was heated to 80° C. for 6 h. An aliquot was taken and TLC (1:1 EtOAc-hexane) indicated that reaction was complete. The slurry was then filtered and the solvent removed in vacuo to obtain a crude yellow oil (0.6 g). The crude product was purified by column chromatography, silica gel 230-400 mesh, eluent: 1:2 EtOAc-hexane to obtain 5-fluoro-N-[(1S,2S)-1-(hydroxymethyl)-2-methyl-butyl]-2-thiophenesulfonamide as an amorphous white solid (0.102 g, 15.49%). Mass Spectrum (–ESI): 280 (M–H)$^-$. Anal. Calc'd for C$_{10}$H$_{16}$NFO$_4$S$_2$: C, 42.69; H, 5.73; N, 4.98. Found: C, 42.47; H, 5.74; N, 4.87.

Example 209

4-[1-(5-Chloro-thiophene-2-sulfonylamino)-2-hydroxy-ethyl]-piperidine-1-carboxylic acid tert-butyl ester

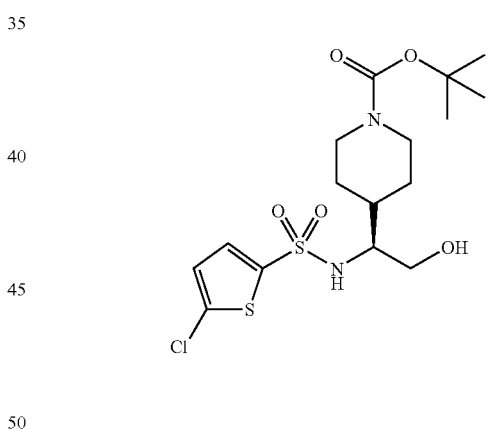

A. t-Butyl 4-((1S)-1-{[(9H-fluoren-9-ylmethoxy)carbonyl]amino}-2-hydroxyethyl)piperdine-1-carboxylate To a solution of cyanuric chloride (1.44 g, 7.80 mmol) in DME (40 mL) was added N-methyl morpholine (0.79 g, 7.80 mmol) at 25° C. A white precipitate formed and to this mixture 4-[carboxy-(9H-fluoren-9-ylmethoxycarbonylamino)-methyl]-piperidine-1-carboxylic acid tert-butyl ester (3.75 g, 7.80 mmol) was added as a solution dissolved in DME (20 mL). After 5 h, the mixture was filtered and the liquid filtrate was cooled in an ice bath to 0° C. and NaBH$_4$ (0.44 g, 11.63 mmol) previously dissolved in H$_2$O (15 mL) was added by pipet. The reaction mixture was stirred for an additional 20 min at 0° C. Diethyl ether (100 mL) was added followed by acidification using 1N HCl solution. The organic phase was then separated and washed with a 10% solution of Na$_2$CO$_3$ followed by brine and then dried over MgSO$_4$. Filtration and evaporation produced a crude glass that was flash chromatographed using ethyl acetate-hexane, 1-1 as eluent. This gave the desired product as a solid (1.03 g, 28%). MS (+ESI) 367.1 ([M+H]$^+$); 282.2; 189.1.

B. t-Butyl 4-[(1S)-1-amino-2-hydroxyethyl]-1-piperidinecarboxylate

To tert-butyl 4-((1S)-1-{[(9H-fluoren-9-ylmethoxy)carbonyl]amino}-2-hydroxyethyl)piperdine-1-carboxylate (0.95 g, 2.03 mmol) was added 20% piperidine in dimethylformamide (20 mL) all at once. The reaction was stirred overnight at 25° C. The dimethylformamide was evaporated off and the crude residue was subjected to flash chromatography using methylene chloride-methanol-ammonium hydroxide, 95-5-0.1% as eluent. This yielded the amine product as an oil that crystallized upon standing (0.392 g, 80%). MS (+ESI) 245.2 ([M+H]$^+$); 189.2; 150.2.

C. 4-[1-(5-Chloro-thiophene-2-sulfonylamino)-2-hydroxy-ethyl]-piperidine-1-carboxylic acid tert-butyl ester To a stirred mixture of tert-butyl 4-[(1S)-1-amino-2-hydroxyethyl]-1-piperidinecarboxylate (0.107 g, 0.44 mmol), triethylamine (0.046 g, 0.46 mmol) and methylene chloride (5 mL) cooled to 0° C., was added 5-chlorothiophene-2-sulfonyl chloride (0.095 g, 0.44 mmol) as a solution dissolved in 2 mL methylene chloride, dropwise by pipet. After 15 min, the ice bath was-removed and the reaction allowed to attain 25° C. and stir overnight. The reaction was quenched by pouring it into saturated sodium bicarbonate solution (25 mL) and additional methylene chloride (15 mL). The organic phase was separated and washed sequentially with 1N HCl solution, H$_2$O, brine and dried over MgSO$_4$. The organic phase was filtered and evaporated to produce a crude oil that was flash chromatographed using ethyl acetate-hexane, 1-1 as eluent. This produced the title compound as a solid (0.109 g, 58%). MS (+APCI) 442.18 ([M+NH$_4$]$^+$); 386.08; 357.01; 325.07; 307.01; 285.06. Anal. Calc'd for C$_{16}$H$_{25}$ClN$_2$O$_5$S$_2$: C, 45.22; H, 5.93; N, 6.59; Found: C, 45.31; H, 5.87; N, 6.44.

Example 210

N-[(1S,2S)-1-(Hydroxymethyl)-2-methylbutyl]thiophene-2-sulfonamide

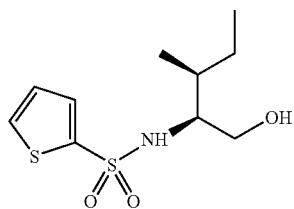

To a solution of 2-thiophenesulfonyl chloride (1 g, 5.48 mmol) in CH$_2$Cl$_2$ (5 mL) and (S)-isoleucinol (642 mg, 5.48 mmol) was added Hunig's base (1.05 mL, 6.02 mmol). The reaction mixture was stirred at 25° C. for 24 h. The solvent was removed and the oil was dissolved in EtOAc (100 mL). The solution was washed with water (2×100 mL), brine (1×100 mL), and dried over Na$_2$SO$_4$. The desired sulfonamide (m/z=264.0 (M+H), rt=0.79 min) was isolated by semi-preparative RP-HPLC using the conditions outlined for example 195.

Example 211

5-Chloro-N-[(S)-2-hydroxy-1-(4-benzylaminocyclohexyl)ethyl]thiophene-2-sulfonamide

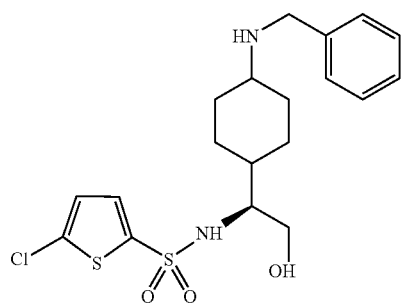

A. Part 1

A solution of (S)-2-(5-Cl-thiophenesulfonamido)-2-(4-hydroxycyclohexyl)-N,O-acetonide (4.8 g, 12.7 mmol, see example 199 part 1-3) in CH$_2$Cl$_2$ (50 mL) was added to a slurry of PCC (5.46 g, 25.3 mmol), silica gel (5.46 g) and sodium acetate (1 g, 12.2 mmol) in CH$_2$Cl$_2$ (30 mL). The resulting reaction mixture was stirred at 25° C. overnight. The mixture was diluted with Et$_2$O and filtered. The solid was washed with diethylether (3×50 mL) and the combined organic extracts were dried over MgSO$_4$. The solvent was removed in vacuo, and the residue was purified by column chromatography using 1:1 EtOAc/Hexane as the eluent to give the ketone as a white solid (4 g, 84%) (100% purity).

B. Part 2

To a solution of (S)-2-(5-Cl-thiophenesulfonamido)-2-(4-cyclohexanone)-N,O-acetonide (340 mg, 0.9 mmol) in 1,2-dichloroethane (6 mL) was added benzylamine (118 μL, 1.08 mmol), sodium triacetoxyborohydride (286 mg, 1.35 mmol), and acetic acid (52 μL, 0.9 mmol). The reaction was stirred at 25° C. overnight whereupon the reaction was quenched with aqueous NaHCO$_3$ and extracted with diethyl ether and evaporated. To the resulting residue was slowly added acetic acid (10 mL of 80%) and the reaction was heated at 40° C. for nine days. The acetic acid was removed and the residue purified by column chromatography (MeOH/CH$_2$Cl$_2$/0.5-1% NH$_4$OH) to furnish the desired compound (254 mg, 66%) as a mixture of diastereomers.

The following compounds (Examples 211-220, Table 20) were prepared using (S)-2-(5-Cl-thiophenesulfonamido)-2-(4-cyclohexanone)-N,O-acetonide (from Example 211, part 1) with benzylamine, methylamine, ethylamine, propylamine, allylamine, 3-(aminomethyl)pyridine, morpholine, 4-(aminomethyl)pyridine, 2-(aminomethyl)pyridine, and glycine ethyl ester as outlined in Example 211.

TABLE 20

(LCMS Data[3]: Molecular ion and retention time)

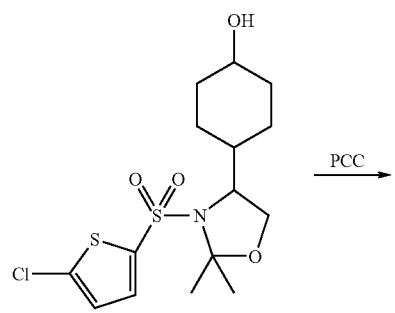

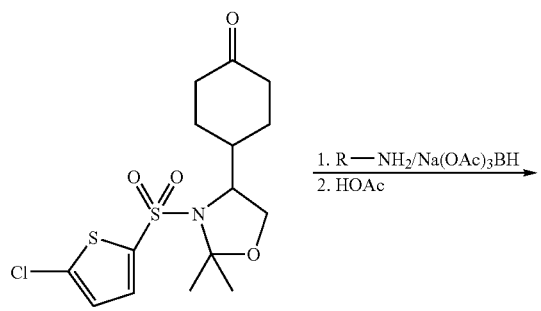

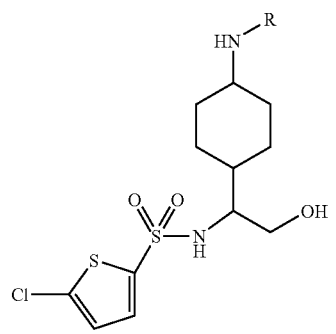

| R—NH$_2$ | |
|---|---|
| benzylamine | Ex. 211 |
| | 427.2(M − H), 0.62 min |
| | 427.2(M − H), 0.66 min |
| methylamine | Ex. 212 |
| | 351.2(M − H), 0.39 min |
| | 351.1(M − H), 0.45 min |
| ethylamine | Example 213 |
| | 365.2(M − H), 0.47 min |
| | 365.2(M − H), 0.53 min |
| n-propylamine | Ex. 214 |
| | 379.2(M − H), 0.55 min |
| | 379.2(M − H), 0.59 min |
| allylamine | Ex. 215 |
| | 376.9(M − H), 0.42 min |
| | 376.9(M − H), 0.47 min |

TABLE 20-continued (LCMS Data[3]: Molecular ion and retention time)

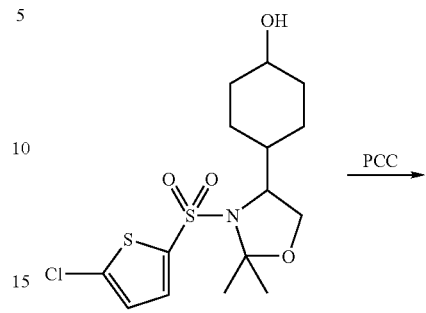

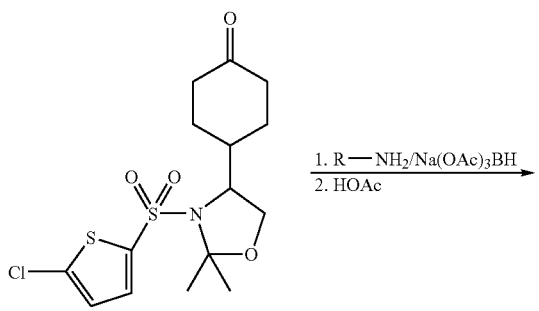

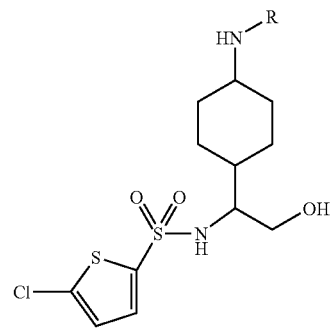

| R—NH$_2$ | |
|---|---|
| 3-(aminomethyl) pyridine | Ex. 216 |
| | 427.9(M − H), 0.35 min |
| | 427.9(M − H), 0.41 min |
| morpholine | Ex. 217 |
| | 406.9(M − H), 0.40 min |
| | 406.9(M − H), 0.44 min |
| 4-(aminomethyl) pyridine | Ex. 218 |
| | 428.0(M − H), 0.49 min |
| | 428.0(M − H), 0.51 min |
| 2-(aminomethyl) pyridine | Ex. 219 |
| | 428.0(M − H), 0.36 min |
| | 428.0(M − H), 0.37 min |
| glycine ethyl ester | Ex. 220 |
| | 423.0(M − H), 0.47 min |
| | 423.0(M − H), 0.51 min |

Example 221A

Method 1

5-Chloro-N-[(S)-2-ethyl-1-formylbutyl]thiophene-2-sulfonamide

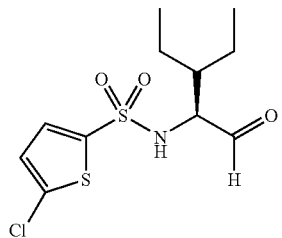

A. 5-(1-Ethyl-propyl)-imidazolidine-2,4-dione

Sodium cyanide (12.0 g, 244.8 mmol) and 2-ethylbutyraldehyde (10.0 mL, 81.3 mmol) were added to ammonium carbonate (25.4 g, 325.3 mmol) in H$_2$O (300 mL). Ethanol (300 mL) was added and salts precipitated. The reaction mixture was heated to 90° C. After 1 h, the mixture became homogeneous and was stirred at 90° C. for 18 h. After cooling to 25° C., about 500 mL of solvent was removed in vacuo. Concentrated HCl was added to acidify the mixture to pH 1-2 and a precipitate formed. It was filtered and the precipitate was recrystallized from EtOAc to afford 5-(1-ethyl-propyl)-imidazolidine-2,4-dione as a white solid (12.9 g, 93%). Mass Spectrum (−ESI): 169 (M−H)$^-$.

B. N-[(5-Chloro-2-thienyl)sulfonyl]-3-ethylnorvaline 5-(1-Ethyl-propyl)-imidazolidine-2,4-dione (12.3 g, 72.3 mmol) was dissolved in a 150 mL solution of aqueous NaOH (11.6 g, 289.2 mmol). The solution was heated by microwave in a sealed vessel for 1 h. (Microwave conditions: 15 min @ 100% power, 150° C., 50 psi, then 5 min 0% power, then 15 min @ 100% power, 150° C., 50 psi, then repeat sequence.) Water and ammonium hydroxide were removed from the reaction mixture in vacuo and the resulting crude amino acid and NaOH mixture was used in the next reaction without further purification.

The crude amino acid and NaOH mixture was dissolved in 300 mL of water. The mixture was cooled to 0° C. in an ice bath. 5-Chlorothiophene-2-sulfonyl chloride (17.3 g, 79.5 mmol) was dissolved in 100 mL of THF and added dropwise to the reaction mixture over 0.5 h. After 1 h the reaction mixture was allowed to warm gradually to 25° C. and stirred for 16 h. THF was removed in vacuo and then the mixture was acidified to pH 1 with 1N HCl. After about 15 min, a precipitate began to crash out of the milky white solution. After 1 h, the mixture was cooled in a refrigerator for 1 h and then filtered. The precipitate was washed with 1 N HCl to provide N-[(5-chloro-2-thienyl)sulfonyl]-3-ethylnorvaline as a white solid (18.5 g, 78%). Mass Spectrum (−ESI): 325 (M−H)$^-$.

C. N-[(5-Chloro-2-thienyl)sulfonyl]-3-ethyl-L-norvaline (+)-(1S,2R)-Ephedrine hemihydrate (16.7 g, 95.6 mmol) was added to a suspension of N-[(5-chloro-2-thienyl)sulfonyl]-3-ethylnorvaline (31.2 g, 95.6 mmol) in 185 mL of EtOH. The mixture was heated slightly to dissolve solids and a precipitate formed. After cooling at 5° C. for 18 h the resulting-suspension was filtered and the precipitate was washed with cold EtOH and EtOAc to give 27% yield of the diastereomeric salt. The salt was recrystallized from boiling EtOAc (420 mL), then filtered off. The resulting white solid was then dissolved in 300 mL of EtOAc and 300 mL of 1N HCl. The layers were separated and the organic extract was washed with 1N HCl (2×200 mL), dried (Na$_2$SO$_4$), and concentrated to give N-[(5-chloro-2-thienyl)sulfonyl]-3-ethyl-L-norvaline as a white solid (5.6 g, 18%). Chiral HPLC [chiralpak AD (25×0.46 cm), 8:2 hexane (0.1% TFA):isopropanol, L-isomer elutes at 9.6 min and D-isomer elutes at 13.1 min] indicated 96% chiral purity. [α]$_D^{25}$=+44.5° (c=1% SOLUTION, MeOH). Mass Spectrum (−ESI): 325 (M−H)$^-$. Anal. Calc'd for C$_{11}$H$_{16}$ClNO$_4$S$_2$: C, 40.55; H, 4.95; N, 4.30. Found: C, 40.30; H, 4.78; N, 4.16.

D. 5-Chloro-N-[(S)-2-ethyl-1-(hydroxymethyl)butyl]-2-thiophenesulfonamide

To N-[(5-Chloro-2-thienyl)sulfonyl]-3-ethyl-L-norvaline (5.6 g, 17.2 mmol) in THF (150 mL) at 0° C. was added a solution of 1 M borane tetrahydrofuran complex in THF (69 mL, 69 mmol) dropwise via addition funnel. After 15 min, the reaction mixture was warmed to 25° C. and stirred for 18 h. It was then quenched with 90 mL of 10% AcOH in MeOH slowly. Volatiles were removed in vacuo. The residue was then dissolved in EtOAc (300 mL) and washed with sat. aqueous NaHCO$_3$ (3×200 mL), dried (Na$_2$SO$_4$), and concentrated to a white precipitate (5.1 g, 96% yield, 96% chiral purity). The precipitate was recrystallized with heptane/EtOAc, 4:1, to give optically pure 5-chloro-N-[(S)-2-ethyl-1-(hydroxymethyl)butyl]-2-thiophenesulfonamide as white needles (4.4 g, 81% yield). [α]$_D^{25}$=+4.5° (c=1% SOLUTION, DMSO). Mass Spectrum (−ESI): 310 (M−H)$^-$. Anal. Calc'd for C$_{11}$H$_{18}$ClNO$_3$S$_2$: C, 42.37; H, 5.82; N, 4.49. Found: C, 42.37; H, 5.79; N, 4.38.

E. 5-Chloro-N-[(S)-2-ethyl-1-formylbutyl]thiophene-2-sulfonamide

Pyridinium dichromate (2.4 g, 6.4 mmol) was added to a solution of 5-chloro-N-[(S)-2-ethyl-1-(hydroxymethyl)butyl]-2-thiophenesulfonamide (0.5 g, 1.6 mmol) in CH$_2$Cl$_2$ (20 mL). After 18 h, the reaction mixture was filtered through a plug of Celite. The filtrate was concentrated and the resulting residue was purified by silica gel column chromatography (eluant: 1:4 EtOAc-hexane) to give 5-chloro-N-[(S)-2-ethyl-1-formylbutyl]thiophene-2-sulfonamide as a white solid (303 mg, 61%). [α]$_D^{25}$=+136.76° (c=1% SOLUTION, CHCl$_3$). Mass Spectrum (−ESI): 308 (M−H)$^-$. Anal. Calc'd for C$_{11}$H$_{16}$ClNO$_3$S$_2$: C, 42.64; H, 5.21; N, 4.52. Found: C, 42.57; H, 5.24; N, 4.52.

Example 221B

Method 2

5-Chloro-N-[(S)-2-ethyl-1-formylbutyl]thiophene-2-sulfonamide

A. (S)-3-Ethyl-2-{[(S)-1-phenylethyl]amino}pentanenitrile

To (S)-(−)-α-methylbenzylamine hydrochloride salt (1.2 g, 7.6 mmol) in 80 mL of 1:1 MeOH/H$_2$O was added potassium cyanide (0.5 g, 7.6 mmol) and 2-methylbutyraldehyde (0.94 mL, 7.6 mmol). A precipitate formed after 30 min. After 20 h, the suspension was filtered and washed with H$_2$O to give (S)-3-ethyl-2-{[(S)-1-phenylethyl]amino}pentanenitrile as a white powder (1.29 g, 74%). Mass Spectrum (+ESI): 310 (M+H)$^+$. Anal. Calc'd for C$_{15}$H$_{22}$N$_2$: C, 78.21; H19.63; N, 12.16. Found: C, 77.90; H, 9.75; N, 12.32.

B. 3-Ethyl-N$^2$-[(S)-1-phenylethyl]-L-norvalinamide

To 25 mL of sulfuric acid at 0° C. was added (S)-3-ethyl-2-{[(S)-1-phenylethyl]amino}pentanenitrile (2.7 g, 11.6 mmol) portionwise. The mixture was warmed to 25° C. After 2 days, the reaction mixture was poured over about 100 g of crushed ice. Concentrated NH$_4$OH was added to neutralize the acid. This mixture was extracted with EtOAc (3×100 mL), dried over Na$_2$SO$_4$, filtered and concentrated to give 3-ethyl-N$^2$-[(S)-1-phenylethyl]-L-norvalinamide (2.6 g, 90%), which was used in the next step without purification. Mass Spectrum (+ESI): 249 (M+H)$^+$. Anal. Calc'd for C$_{15}$H$_{24}$N$_2$O: C, 72.54; H, 9.74; N, 11.28. Found: C, 72.24; H, 10.04; N, 11.01

C. 3-Ethyl-L-norvalinamide

A mixture of 3-ethyl-N$^2$-[(S)-1-phenylethyl]-L-norvalinamide (2.6 g, 10.5 mmol) and 5% Pd/C (800 mg) was shaken for 24 h in a Parr apparatus under 3 atm of H$_2$. The mixture was filtered through a plug of Celite and the solvent was removed in vacuo to give 3-ethyl-L-norvalinamide as a white solid (1.4 g, 93%), which was used in the next reaction without further purification. Mass Spectrum (+ESI): 145 (M+H)$^+$.

D. N-[(5-Chloro-2-thienyl)sulfonyl]-3-ethyl-L-norvaline

3-Ethyl-L-norvalinamide (1.2 g, 4.8 mmol) was dissolved in conc. HCl (10 mL) and heated to 100° C. for 16 h. The reaction mixture was concentrated to a white solid consisting of the amino acid hydrochloride salt and one equivalent of NH$_4$Cl, which was used in the next reaction without purification.

Amino acid hydrochloride salt with 1 equivalent of NH$_4$Cl (0.28 g, 1.19 mmol) was dissolved in 6 mL of H$_2$O and then NaOH (0.24 g, 6.00 mmol) was added. The solution was cooled to 0° C. and then 5-chlorothiophene-2-sulfonyl chloride (0.29 g, 1.32 mmol) in 6 mL of THF was added dropwise. The mixture was warmed to 25° C. After 19 h, THF was removed in vacuo. The remaining solution was diluted with 10 mL of H$_2$O and washed with EtOAc (2×10 mL). The solution was acidified with 1N HCl and a precipitate formed. This was filtered to give N-[(5-chloro-2-thienyl)sulfonyl]-3-ethyl-L-norvaline as a white solid (0.17 g, 44%). Chiral HPLC indicates that only the S enantiomer is present.

5-Chloro-N-[(S)-2-ethyl-1-(hydroxymethyl)butyl]-2-thiophenesulfonamide and 5-Chloro-N-[(S)-2-ethyl-1-formylbutyl]thiophene-2-sulfonamide were then prepared from N-[(5-Chloro-2-thienyl)sulfonyl]-3-ethyl-L-norvaline according to method 1 of Example 221A.

Example 221C

5-Chloro-N-[(S)-2-ethyl-1-(hydroxymethyl)butyl]-2-thiophenesulfonamide

Into a 3L 3-necked flask equipped with a nitrogen inlet tube, a mechanical stirrer, and an addition funnel with a stopper was placed lithium borohydride (145 mL of a 2 M solution in THF, 0.29 mol). The solution was placed under nitrogen and cooled to 0° C. Chlorotrimethylsilane (73.8 mL, 0.58 mol) was added dropwise over a period of 30 min. The ice bath was removed and the resulting slurry was stirred at room temperature for 30 min. The reaction mixture was cooled to 0° C. and the 2-(S)-amino-3-ethyl-pentanoic acid (21.1 g, 0.145 mol), which was prepared according to Scheme 13, was added in portions as a solid over a period of 15 min. The reaction mixture was allowed to warm slowly to room temperature as the ice bath melted. After 3 days at room temperature, the reaction mixture was cooled to 0° C., and methanol (217 mL) was carefully added over a period of 80 min. The solution was stirred at room temperature for an additional 40 min, then concentrated under reduced pressure in a water bath at 60° C. The resulting slurry was made basic with 20% sodium hydroxide (37.5 mL). Water (37.5 mL) was added, and the entire aqueous layer was extracted with methylene chloride (300 mL), and dried (Na$_2$SO$_4$). Concentration under reduced pressure gave 2(S)-amino-3-ethylpentanol as an oil (17.3 g, 91%), which was used immediately or stored in the freezer overnight: Opt. Rot. [α]$_D^{25}$=−3.7° (1% solution, DMSO); $^1$H NMR (DMSO-d$^6$, 500 MHz): δ 4.38 (broad s, 1H), 3.35 (dd overlapping with a broad s at δ 3.32, J=4.5, 10.3 Hz, 3H), 3.14 (dd, J=7.9, 10.2 Hz, 1H), 2.63 (m, 1H), 1.45-1.05 (m, 5H), 0.82 and 0.81 (two overlapping triplets, J=7.4 Hz, 6H); MS(+ESI): [M+H]$^+$, 132 (60%).

A mixture of 2(S)-amino-3-ethylpentanol (34.1 g, 0.26 mol) and methylene chloride (700 mL) was placed under Argon, and cooled to 0° C. Triethylamine (36.2 mL, 0.26 mol) was added, followed by the dropwise addition of 5-chlorothiophene-2-sulfonyl chloride (56.4 g, 0.26 mol) in methylene chloride (400 mL). The reaction mixture was allowed to warm slowly to room temperature as the ice bath melted. After 3 days at room temperature, the reaction mixture was divided into two-0.6 L portions. Each portion was diluted with ethyl acetate (1L), and washed three times with saturated potassium phosphate monohydrate (200 mL), once with brine (200 mL), and dried (Na$_2$SO$_4$). Concentration under reduced pressure gave a white solid (74.5 g, 92%). The product (87.98 g) from several runs were combined and recrystallized from hot heptane:ethyl acetate (4:1, 775 mL) to give the title compound as crystals (74.9 g, 85%): mp 115-117.6° C.; Opt. Rot. [α]$_D^{25}$=+10.81° (1% solution, MeOH); $^1$H NMR (DMSO-d$^6$, 500 MHz): δ 7.71 (d, J=8.1 Hz, 1H), 7.44 (d, J=4.1 Hz, 1H), 7.22 (d, J=4.1 Hz, 1H), 4.56 (t, J=5.2 Hz, OH), 3.31-3.15 (m, 3H), 1.40-1.115 (m, 4H), 1.07 (m, 1H), 0.79 and 0.76 (two overlapping triplets, J=7.3 Hz, 6H); $^{13}$C NMR (DMSO-d$^6$, 100 MHz): δ 141.75, 133.73, 130.95, 127.60, 60.41, 56.89, 41.57, 21.31, 20.80, 11.79, 11.51; MS(−ESI): [M−H]$^-$, 1 chlorine isotope pattern, 310 (100%), 312 (30%); Anal. Calc. for C$_{11}$H$_{18}$ClNO$_3$S$_2$: C, 42.37, H, 5.82, N, 4.49. Found: C, 42.34, H, 5.65, N, 4.43. Chiral HPLC (Chiralpak A D, 25×0.46 cm, eluant 8:2 hexane/isopropanol containing 0.1% TFA, flow rate 0.5 mL/min, UV detection at 254 nm, retention times for the S and R isomers are 10.95 min and 11.95 min, respectively) revealed an S/R ratio of 100.0:0.0.

Example 222

5-Chloro-N-[(S)-2-ethyl-1-(1-hydroxyethyl)butyl]thiophene-2-sulfonamide

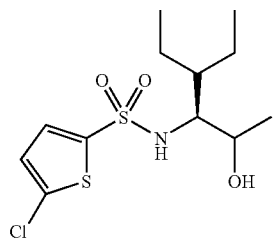

A solution of methylmagnesium bromide (1.4 M, 7.0 mL, 9.7 mmol) in toluene/THF (75:25) was added to a 0° C. solution of 5-chloro-N-[(S)-2-ethyl-1-formylbutyl]thiophene-2-sulfonamide (Example 221, 1.0 g, 3.2 mmol) in THF (30 mL). The mixture was warmed to 25° C. and after 2 h was quenched carefully with saturated aqueous ammonium chloride (25 mL). The mixture was extracted with EtOAc (3×25 mL). The organic extract was dried over $Na_2SO_4$, filtered and concentrated to give a colorless oil. The product was purified by column chromatography (Biotage), eluant: 1:4 EtOAc-hexane, to afford 5-chloro-N-[(S)-2-ethyl-1-(1-hydroxyethyl)butyl]thiophene-2-sulfonamide as a white solid (876 mg, 83%). The product is a diastereomeric mixture with a ratio of 3:7. mp 95-98° C. Anal. Calc'd for $C_{12}H_{20}ClNO_3S_2$: C, 44.23; H, 6.19; N, 4.30. Found: C, 44.25 H, 6.35; N, 4.29. Mass Spectrum (-ESI): 324 (M-H)⁻.

Example 223

5-Chloro-N-[(S)-2-ethyl-1-(1-hydroxy-1-methylethyl)butyl]thiophene-2-sulfonamide

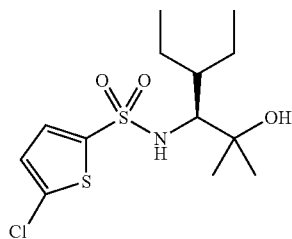

A. N-[(5-Chloro-2-thienyl)sulfonyl]-3-ethyl-L-norvaline methyl ester

Trimethylsilyldiazomethane (3.1 mL, 6.1 mmol) was added to a solution of N-[(5-chloro-2-thienyl)sulfonyl]-3-ethyl-L-norvaline (1.0 g, 3.1 mmol) in THF (20 mL) and MeOH (5 mL). After 2 h the mixture was concentrated to give N-[(5-chloro-2-thienyl)sulfonyl]-3-ethyl-L-norvaline methyl ester as a white solid (1.0 g, 99%). Mass Spectrum (-ESI): 338.00 (M-H)⁻.

B. 5-Chloro-N-[(S)-2-ethyl-1-(1-hydroxy-1-methylethyl)butyl]thiophene-2-sulfonamide A solution of methylmagnesium bromide (1.4 M, 9.5 mL, 13.2 mmol) in toluene/THF (75:25) was added to a 0° C. solution of N-[(5-chloro-2-thienyl)sulfonyl]-3-ethyl-L-norvaline methyl ester (0.90 g, 2.65 mmol) in THF (26 mL). The solution was allowed to warm to 25° C., then heated to 55° C. and stirred for 18 h. It was then cooled to 0° C. and quenched slowly with saturated aqueous $NH_4Cl$. EtOAc (75 mL) was added and the phases were separated. The organic layer was dried over $Na_2SO_4$, filtered and concentrated to give a yellow oil. The crude product was purified by column chromatography (Biotage), eluant: 1:4 EtOAc-hexane, to afford 5-chloro-N-[(S)-2-ethyl-1-(1-hydroxy-1-methylethyl)butyl] thiophene-2-sulfonamide as a colorless oil (0.72 g, 80%). Mass Spectrum (-ESI): 338 (M-H)⁻. Anal. Calc'd for $C_{13}H_{22}ClNO_3S_2$: C, 45.94; H, 6.52; N, 4.12. Found: C, 46.10; H, 6.63; N, 4.04.

Example 224

5-Chloro-N-(2-hydroxy-1-tetrahydro-H-thiopyran-4-ylethyl)thiophene-2-sulfonamide

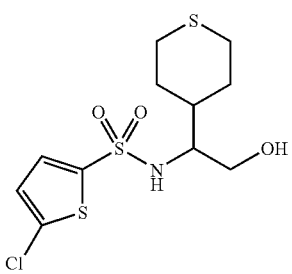

A. (5-Chloro-thiophene-2-sulfonylamino)-(tetrahydro-thiopyran-4-yl)-acetic acid

Sodium hydroxide (0.20 g, 5.04 mmol) was added to a mixture of N-Fmoc-amino-(4-tetrahydrothiopyranyl)acetic acid (0.50 g, 1.26 mmol) in MeOH:water, 2:1 (15 mL) at 25° C. The reaction mixture was allowed to stir for 20 h. TLC (1:9 MeOH/CHCl₃) indicated that the reaction was complete. The mixture was diluted with water and washed with EtOAc. The water layer was concentrated to give a white solid with NaOH remaining. This white solid was redissolved in $H_2O$:THF, 1:2 (15 mL) and cooled to 0° C. 5-chlorothiophene-2-sulfonyl chloride (0.683 g, 3.15 mmol) was dissolved in THF (2 mL) and added to the mixture dropwise which was then warmed to 25° C. overnight. Aqueous 1 N HCl was added to acidify the mixture to pH 1. EtOAc was added and the layers were separated. The organic extract was washed with 1 N HCl, and $H_2O$, dried over $Na_2SO_4$, filtered and concentrated to give (5-chloro-thiophene-2-sulfonylamino)-(tetrahydro-thiopyran-4-yl)-acetic acid as a reddish black solid (0.14, 31%), which was used in the next reaction without purification. Mass Spectrum (+ESI): 357 (M+H)⁺.

B. 5-Chloro-N-(2-hydroxy-1-tetrahydro-H-thiopyran-4-ylethyl)thiophene-2-sulfonamide (5-Chloro-thiophene-2-sulfonylamino)-(tetrahydro-thiopyran-4-yl)-acetic acid (0.14 g, 0.40 mmol) was dissolved in THF (2 mL) and cooled to 0° C. A solution of borane tetrahydrofuran complex (1 M, 3.2 mL, 3.2 mmol) in THF was added dropwise and the mixture was allowed to warm to 25° C. overnight. The volatile solvents were removed in vacuo and the resulting orange oil was diluted with EtOAc and washed with $H_2O$, 1 N HCl, and saturated aqueous $NaHCO_3$. The organic extract was dried over $Na_2SO_4$, filtered and concentrated. The resulting residue was purified by column chromatography (Biotage), eluant: 1:1 EtOAc:hexane, to afford 5-chloro-N-(2-hydroxy-1-tetrahydro-H-thiopyran-4-ylethyl)thiophene-2-sulfonamide (40 mg, 30%) as a white solid. mp 108-110° C. Mass Spectrum (-ESI): 340 (M-H)⁻. Anal. Calc'd for $C_{11}H_{16}ClNO_3S_3$: C, 38.64; H, 4.72; N, 4.10. Found: C, 38.80; H, 4.69; N, 3.88.

Example 225

5-Chloro-N-[(S)-2-hydroxy-1-piperidin-4-ylethyl]thiophene-2-sulfonamide

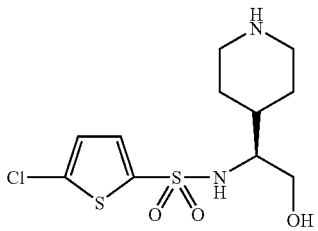

To a solution of 4-[1-(5-chloro-thiophene-2-sulfonylamino)-2-hydroxy-ethyl]-piperidine-1-carboxylic acid tert-butyl ester (0.204 g, 0.48 mmol (see example 209)) dissolved in dichloromethane (2 mL) at 0° C. was added trifluoroacetic acid (0.5 mL). The reaction was allowed to warm to 25° C. and stir overnight. The mixture was then concentrated and dichloromethane was added and evaporated 6 times to yield a crude solid. Purification by HPLC (C-18 column, (21×75 mm) with elution system 60-100% acetonitrile-water+0.1% TFA, 20 min gradient) gave the product as an oil (0.0166 g, 11%). MS (ESI) m/z 325 ([M+H]+).

Example 226

N-[(S)-2-Ethyl-1-(hydroxymethyl)butyl]thiophene-2-sulfonamide

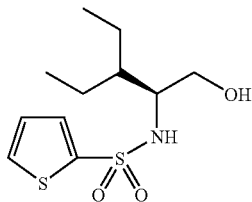

A. N-[(1S)-2-Ethyl-1-(hydroxymethyl)butyl]-5-(trimethylstannyl)thiophene-2-sulfonamide A solution of 5-bromo-N-[(1S)-2-ethyl-1-(hydroxymethyl)butyl]thiophene-2-sulfonamide (0.71 g, 2.0 mmol), hexamethylditin (0.983 g, 3.0 mmol), tetrakis(triphenylphosphine)palladium (0.115 g, 0.10 mmol) and 1,4-dioxane (15 mL) was refluxed for 16 h under a nitrogen atmosphere. After cooling to 25° C., dichloromethane (10 mL) was added and the mixture filtered and evaporated to give the product as a crude oil (0.49 g), that was used without purification in the next step, part B. MS (–ESI) 439.20 ([M–H]–).

B. N-[(S)-2-Ethyl-1-(hydroxymethyl)butyl]thiophene-2-sulfonamide

To a stirred mixture of anhydrous acetonitrile (6 mL) and N-[(1S)-2-ethyl-1-(hydroxymethyl)butyl]-5-(trimethylstannyl)thiophene-2-sulfonamide (0.24 g, 0.56 mmol) was added Selectfluor (Aldrich) (0.204 g, 0.57 mmol) all at once. The mixture was heated to 75° C. under a nitrogen atmosphere, stirred 16 h and then cooled to 25° C. and filtered. Evaporation of the solvent produced a crude solid that was taken up in ethyl acetate and again filtered to remove insoluble solids. Evaporation of the remaining solvent produced an oil that was purified by flash chromatography using hexane-ethyl acetate 2-1 as eluant, producing the title compound as the major product (0.051 g, 33%). MS (–ESI) 276.20 ([M–H]–).

Example 227

N-[(S)-2-Ethyl-1-(hydroxymethyl)butyl]-5-fluorothiophene-2-sulfonamide

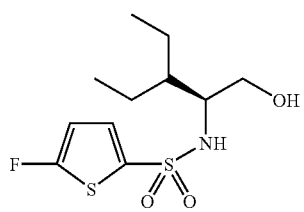

This compound was synthesized as a side product using the procedure found in example 226 (parts A and B) and was isolated from the same flash chromatography column as a solid (0.024 g, 15%). MS (–ESI) 294.20 ([M–H]–).

Example 228

5-Chloro-N-[(1S)-1-(2,3-dihydro-1H-inden-2-yl)-2-hydroxyethyl]thiophene-2-sulfonamide

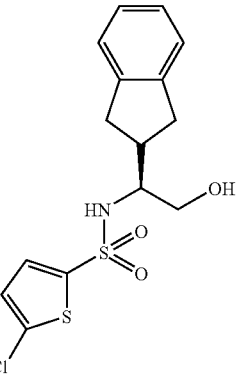

A. 9H-Fluoren-9-ylmethyl-(1S)-1-(2,3-dihydro-1H-inden-2-yl)-2-hydroxyethylcarbamate 1N Borane-THF (24.18 mL) was added dropwise over 30 min at 0° C. to a solution of (2S-2,3-dihydro-1H-indene-2-yl [[(9H-fluoren-9-ylmethoxy)carbonyl]amino)ethanoic acid (2.0 g, 4.84 mmol) in anhydrous tetrahydrofuran (20 mL). The reaction was allowed to warm to 25° C. overnight, and then was quenched by addition of 10.0 mL of 10% acetic acid in methanol. After solvent evaporation, the crude product was dissolved in ethyl acetate and washed with 1N HCl, water and 10% NaHCO3. The organic layer was dried over MgSO4, filtered and concentrated to obtain a crude yellow oil (1.8 g). The crude product was purified by column chromatography, silica gel 230-400 mesh, eluant: 1:2 EtOAc-hexane. This produced the title compound as an amorphous solid (1.05 g, 54.4%). Mass Spectrum (–ESI): 398 (M–H)–. (+ESI): 400 (M+H)+.

B. (2S)-2-Amino-2-(2,3-dihydro-1H-inden-2-yl)ethanol

20% Piperidine in DMF (15 mL) was added to a solution of 9H-fluoren-9-ylmethyl-(1S)-1-(2,3-dihydro-1H-inden-2- yl)-2-hydroxyethylcarbamate (1.05 g, 2.63 mmol) in DMF (5 mL). The reaction was stirred at 25° C. for 19 h. After solvent evaporation, the crude product was dissolved in ethyl acetate (50 mL) and dried over MgSO$_4$, filtered and concentrated to obtain a crude yellow oil (1.05 g). Mass Spectrum (+ESI): 179 (M+H)$^+$.

C. 5-Chloro-N-[(1S)-1-(2,3-dihydro-1H-inden-2-yl)-2-hydroxyethyl]thiophene-2-sulfonamide 5-Chlorothiophene-2-sulfonyl chloride (0.856 g, 3.94 mmol) was added dropwise (5 min) as a solution in CH$_2$Cl$_2$ (5 mL) to a 0° C. solution of (2S)-2-amino-2-(2,3-dihydro-1H-inden-2-yl)ethanol (0.46 g, 2.63 mmol) in CH$_2$Cl$_2$ (5 mL) and triethylamine (3.8 mL, 5.26 mmol). The solution was allowed to warm to 25° C. overnight (19 h). An aliquot was taken and TLC (1:1 EtOAc-hexane) indicated that reaction was complete. It was diluted with CH$_2$Cl$_2$ (50 mL) and the organic layer was washed with 1N HCl (2×50 mL), saturated aqueous NaCl (50 mL). The organic layer was dried over MgSO$_4$, filtered and concentrated to obtain a crude oil (0.89 g). The crude product was purified by column chromatography, silica gel 230-400 mesh, eluant: 1:4 EtOAc-hexane to afford 5-chloro-N-[(1S)-1-(2,3-dihydro-1H-inden-2-yl)-2-hydroxy-ethyl]thiophene-2-sulfonamide as an amorphous white solid (0.361 g, 38.4%). Mass Spectrum (–ESI): 356 (M–H)$^-$. Anal. Calc'd for C$_{15}$H$_{10}$ClNO$_3$S$_2$: C: 50.34 H: 4.51 N: 3.91 Found: C: 50.28 H: 4.36 N: 3.77.

Example 229

5-Chloro-N-{(1S,2S)-1-[(Z)-(hydroxyimino)methyl]-2-methylbutylthiophene-2-sulfonamide

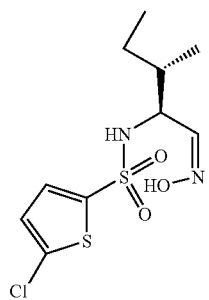

A solution of 5-chloro-N-[(1S,2S)-1-formyl-2-methylbutyl]thiophene-2-sulfonamide (Example 118, 1.0 g, 3.4 mmol), hydroxylamine hydrochloride (0.464 g, 6.78 mmol) and sodium acetate (0.556 g, 6.78 mmol) in methanol (10 mL) was stirred under reflux for 19 h. After evaporation of the solvent, the residue was diluted with aqueous K$_2$CO$_3$ (20 mL) and then extracted with CH$_2$Cl$_2$ (2×40 mL). The combined reaction extracts were washed with brine, dried over MgSO$_4$, filtered and concentrated to obtain a crude oil (0.89 g). The crude product was purified by column chromatography, silica gel 230-400 mesh, eluant: 1:4 EtOAc-hexane. This produced the title compound (Z-isomer) as an amorphous white solid (32 mg, 3.1%). Mass Spectrum (–ESI): 309 (M–H)$^-$. Anal. Calc'd for C$_{10}$H$_{15}$ClN$_2$O$_3$S$_2$. 0.10 C$_4$H$_8$O$_2$: C: 39.08 H: 4.98 N: 8.76 Found: C: 38.72 H: 4.67 N: 8.43.

Example 230

5-chloro-N-{(S,S)-1-[(E)-(hydroxyimino)methyl]-2-methylbutylthiophene-2-sulfonamide

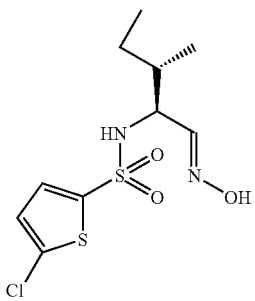

A solution of 5-chloro-N-[(1R,2S)-1-formyl-2-methylbutyl]thiophene-2-sulfonamide (Example 118, 1.0 g, 3.4 mmol), hydroxylamine hydrochloride (0.464 g, 6.78 mmol) and sodium acetate (0.556 g, 6.78 mmol) in methanol (10 mL) was stirred under reflux for 19 h. After evaporation of the solvent, the residue was diluted with aqueous K$_2$CO$_3$ (20 mL) and then extracted with CH$_2$Cl$_2$ (2×40 mL). The combined reaction extracts were washed with brine, dried over MgSO$_4$, filtered, and concentrated to obtain a crude oil (0.89 g). The crude product was purified by column chromatography, silica gel 230-400 mesh, eluant: 1:4 EtOAc-hexane This produced the title compound (E-isomer) as an amorphous white solid (300 mg, 28.3%). Mass Spectrum (–ESI): 309 (M–H)$^-$. Anal. Calc'd for C$_{10}$H$_{15}$ClN$_2$O$_3$S$_2$.0.40 C$_4$H$_8$O$_2$: C: 40.26 H: 5.30 N: 8.09 Found: 39.78 H: 5.23 N: 7.77

A. Diethyl-3-ethyl-5-oxopyrrolidine-2,2-dicarboxylate

To 150 mg of sodium dissolved in 150 mL of absolute ethanol was added diethyl acetamidomalonate (5.3 g, 25 mmol) and ethyl-(2E)-pent-2-enoate (3.5 g, 27.3 mmol). The reaction mixture was then refluxed for 20 h. After this period of time, 2 mL of glacial acetic acid was added, volatiles were removed under pressure with the aid of a water aspirator and heating bath. On cooling the residue solidified. The residue was dissolved in 50 mL of toluene and to this was added 20 mL of petroleum ether. The product precipitated when the mixture was cooled. The crystals were collected and washed with water and further dried in vacuo to obtain a white solid (5.6 g, 79.77%). Mass Spectrum (+ESI): 258 (M+H)$^+$.

B. 3-Ethylglutamic acid 5.6 g of Diethyl-3-ethyl-5-oxopyrrolidine-2,2-dicarboxylate (21.76, 84.67 mmol) was refluxed in 80 mL of 49% fuming HBr for 4 h. After this time, the contents were placed in vacuo and the volatile constituents were removed. The gummy residue was dissolved in 25 mL of distilled water and the water was removed as before. The process was repeated once more. The residue was dissolved in 20 mL of water and the pH of the solution was adjusted to pH 3 with concentrated ammonia (2 mL) solution. At this point precipitation of the ethyl glutamic acid was encouraged by cooling on an ice bath or by diluting the aqueous solution with 100 mL of absolute ethanol. Precipitation from the water-ethanol mixture is complete in 48 h. Care must be taken to add the ethanol slowly to prevent the precipitation of an undesired side product. The compound was purified by crystallization from water-ethanol (1:1) mixture. This produced the title compound as an amorphous white solid (3.5 g, 99%). Mass Spectrum (+ESI): 176 (M+H)$^+$.

C. 3-Ethyl-2-methylpentane-1,5-diol

To a slurry of LAH (2.06 g, 54.29 mmol) in THF (60 mL) was added 3-ethylglutamic acid (3.5 g, 21.71 mmol) dropwise at 0° C. over 20 min. The reaction was heated to 36° C. for 18 h. The reaction slurry (gray) was cooled to 0° C. and quenched with H$_2$O (3 mL) then washed with 1N NaOH (9 mL) and H$_2$O (3 mL). It was then stirred for 6 h at 25° C. to obtain an off-white slurry. The slurry was filtered and the mother liquor was further dried over MgSO$_4$, filtered and concentrated in vacuo to obtain 3-ethyl-2-methylpentane-1, 5-diol as a crude yellow oil (2.85 g, 89.17%). Mass Spectrum (+ESI): 170 (M+Na)$^+$.

D. 5-Chloro-N-[2-ethyl-4-hydroxy-1-(hydroxymethyl) butyl]thiophene-2-sulfonamide 5-Chlorothiophene-2-sulfonyl chloride (6.4 g, 24.48 mmol) was added dropwise (5 min) as a solution in CH$_2$Cl$_2$ (5 mL) to a 0° C. solution of 3-ethyl-2-methylpentane-1,5-diol (2.85 g, 19.34 mmol) in CH$_2$Cl$_2$ (30 mL) and triethylamine (5.66 mL, 40.81 mmol). The solution was allowed to warm to 25° C. overnight (19 h). An aliquot was taken and TLC (1:1 EtOAc-hexane) indicated that reaction was complete. It was diluted with CH$_2$Cl$_2$ (50 mL) and the organic layer was washed with 1N HCl (2×50 mL) and saturated aqueous NaCl (50 mL). The organic layer was dried over MgSO$_4$, filtered and concentrated to obtain a crude oil (4.9 g). The crude product was purified by column chromatography, silica gel 230-400 mesh, eluant: 1:4 EtOAc-hexane to afford 5-chloro-N-[2-ethyl-4-hydroxy-1-(hydroxymethyl)butyl]thiophene-2-sulfonamide as an amorphous white solid (0.450 g, 7.3%). Mass Spectrum (−ESI): 326 (M−H)$^-$.

1. Semi-Preparative RP-HPLC Conditions:

Gilson Semi-Preparative HPLC system with Unipoint Software.

Column: Phenomenex C18 Luna 21.6 mm×60 mm, 5μ

Solvent A: Water (0.02% TFA buffer)

Solvent B: Acetonitrile (0.02% TFA buffer)

Solvent Gradient: Time 0: 10% B; 2.5 min: 10% B; 14 min: 90% B.

Flow Rate: 22.5 mL/min

The product peak was collected based on UV absorption and concentrated.

2. Analytical LCMS Conditions:

Hewlett Packard 1100 MSD with ChemStation Software

Column: YMC ODS-AM 2.0 mm×50 mm 5μ column at 23° C.,

3 μL injection;

Solvent A: Water (0.02% TFA buffer)

Solvent B: Acetonitrile (0.02% TFA buffer)

Gradient: Time 0: 95% A; 0.3 min: 95% A; 4.7 min: 10% A; 4.9 min: 95% A.

Flow rate 1.5 mL/min;

Detection: 254 nm DAD;

API-ES Scanning Mode Positive 150-700; Fragmentor 70 mV.

3. Analytical LCMS Conditions:

ZMD (Waters) or Platform (Micromass) or LCZ (Micromass)

Column: Zorbax SB-C8

Solvent: Acetonitrile+H$_2$O containing 0.1% TTA or 0.1% FA

Gradient: Gradient: 2.5 min 15% Acetonitrile—95% Acetonitrile

Flow rate 3 ml\min

Detection: ELSD detection (SEDEX 55)

UV 253 detection (Schimadzu)

Example 233

Repressor Release Assay (RRA)

The compounds generated as described in Examples 1 through 220 were tested in the RRA in accordance with published techniques [Shuey, D. J., Sheiffele, P., Jones, D., Cockett, M. I., and Quinet, E. M. (1999), "Repressor release: a useful tool for monitoring amyloid precursor protein (APP) proteolysis in mammalian cells", *Society for Neuroscience Abstracts*, Vol. 25, 29$^{th}$ Annual Meeting of Society for Neuroscience, Miami Beach, Fla., Oct. 23-28, 1999]. Briefly, this assay is performed as follows.

A. Cell Culture

CHO-K1 cells are cultured in whole DMEM media (DMEM—High Glucose with 10% fetal bovine serum, 1% Non-essential Amino Acids, and 1% Penicillin-Streptomycin) at 37° C. with 5% CO$_2$. Two million cells are plated into 10-cm dishes 24 hrs prior to transfection.

Transient transfections are completed as recommended by Gibco BRL using their Lipofectamine Plus system. First, 6 μg of pRSVO-luc and 6 μg of APP-lacI construct DNA are added to 460 μL Opti-Mem transfection media and incubated with 30 μL Plus reagent for 15 minutes. Then, a lipid mixture of 40 μL Lipofectamine reagent and 460 μL Opti-Mem transfection media is incubated with the DNA-Plus reagent mixture for 15 minutes. During the DNA-lipid incubation, the CHO-K1 cells are washed once and covered in 5.0 mL DMEM media without Penicillin-Streptomycin. The DNA-lipid preparation is then layered onto these cells and incubated at 37° C. overnight.

One and one half million transfected cells per well (100 μL total volume) are plated into sterile, opaque Packard 96-well Cultur-Plates in clear DMEM whole media (DMEM—without phenol red) and incubated at 37° C. with 5% CO$_2$ for 3-5 hours.

B. Compound Dilution

Compounds are diluted using two different protocols; one protocol is used for compounds supplied neat (weighed powder in vial) and the other protocol is used for compounds supplied in solution (20 mM in DMSO in 96-well plates). For both protocols, 25 mM Hepes and 25 mM Hepes/1% DMSO are prepared fresh to be used as diluent. The Hepes/DMSO is used as the diluent control on all experimental plates.

The following table depicts the steps for compound dilution (please note that the last step is the addition of compound to cells/media in tissue culture plate):

TABLE 21

|  | Concentration | Dilution |
| --- | --- | --- |
| Stock Solution | 10 mg/mL | x mg compound (vial) diluted with 100% DMSO |
| Dilution 1 | 1 mg/mL | 20 μL stock solution 180 μL 25 mM Hepes |
| Dilution 2 | 200 μg/mL | 60 μL Dilution 1 240 μL 25 mM Hepes |
| Dilution 3 (in Cell Plate) | 20 μg/mL | 11.3 μL Dilution 2 (in 100 μL cells/well) |

Because some compounds arrive in 96-well format at 20 mM, the following represents the protocol for their dilution (note that an average molecular weight of these compounds was used to calculate these dilutions and as above, the last step is the addition of compound to cells/media in tissue culture plate):

TABLE 22

|  | Concentration | Dilution |
|---|---|---|
| Stock Solution (original conc.) | — | 20 mM Solution |
| Dilution 1 | ~200 μg/mL | 6 μL stock solution 194 μL 25 mM Hepes |
| Dilution 2 (in Cell Plate) | ~20 μg/mL | 11.3 μL Dilution 2 (in 100 μL cells/well) |

Once compounds are diluted, they are applied in duplicate on cells in tissue culture plates (prepared above). Cells are incubated with compound at 37° C. with 5% $CO_2$ for an additional 36-48 hours.

C. Assay Measurement

Luciferase assays (LucLite reagent, Packard) are performed and are read on a Packard TopCount instrument. Media is removed from each 96-well plate and replaced with 100 μL PBS per well (with $Mg^{2+}$ and $Ca^{2+}$). An equal volume (100 μL) of the LucLite lysis/substrate buffer is added to each well and the plates are sealed and mixed in the dark on a rotary shaker for 15-30 minutes at room temperature. Luciferase readings are then taken on the TopCount instrument. Measurements are expressed as relative light units (RLU) and are calculated and analyzed in MS Excel as follows.

D. Analysis of Data

The results of the assay with respect to the compounds exemplified herein are provided in the following table. A compound is considered active in RRA if it leads to at least a 1.5 fold increase in luciferase activity at 20 μM and is non-toxic, as determined by loss of signal (<0.75 fold increase). Fold increase is the amount of luciferase activity (measured in relative light units) over diluent control. SEM represents the standard error of the mean for fold increase (not shown). All compounds tested were found to be non-toxic.

TABLE 23

| Ex # | Conc (μg/mL) | APPI Fold Increase | Name |
|---|---|---|---|
| 1 | 10 | 1.57 | 3-bromo-5-chloro-N-[(1S,2S)-1-(hydroxymethyl)-2-methylbutyl]thiophene-2-sulfonamide |
| 2 | 10 | 3.2 | 5-bromo-N-[(1S,2S)-1-(hydroxymethyl)-2-methylbutyl]thiophene-2-sulfonamide |
|  | 3 | 2.34 |  |
|  | 10 | 3.06 |  |
|  | 10 | 4.26 |  |
|  | 1 | 1.79 |  |
|  | 20 | 4.5 |  |
|  | 20 | 5.5 |  |
|  | 20 | 6.3 |  |
|  | 3 | 2.96 |  |
|  | 1 | 1.54 |  |
| 3 | 10 | 1 | 4-bromo-5-chloro-N-[(1S,2S)-1-(hydroxymethyl)-2-methylbutyl]thiophene-2-sulfonamide |
|  | 20 | 1.5 |  |
|  | 20 | 25.4 |  |
| 4 | 10 | 3.3 | 5-chloro-N-[(1S,2S)-1-(hydroxymethyl)-2-methylbutyl]thiophene-2-sulfonamide |
|  | 3 | 2.98 |  |
|  | 3 | 3.52 |  |
|  | 20 | 4 |  |
|  | 20 | 4 |  |
|  | 20 | 5.4 |  |
|  | 20 | 3.3 |  |
|  | 20 | 5.1 |  |
|  | 1 | 2.22 |  |
|  | 10 | 5.03 |  |
| 5 | 3 | 1.1 | 2,5-dichloro-N-[(1S,2S)-1-(hydroxymethyl)-2-methylbutyl]thiophene-3-sulfonamide |
|  | 1 | 0.9 |  |
|  | 0.3 | 0.9 |  |
|  | 10 | 1.1 |  |
| 6 | 10 | 1.1 | 4,5-dichloro-N-[(1S,2S)-1-(hydroxymethyl)-2-methylbutyl]thiophene-2-sulfonamide |
|  | 20 | 1.5 |  |
|  | 20 | 2.9 |  |
| 7 | 20 | 3.2 | N-[(1S,2S)-1-(hydroxymethyl)-2-methylbutyl]thiophene-2-sulfonamide |
| 8 | 10 | 3.7 | 5-chloro-N-[(1S)-1-(hydroxymethyl)-2-methylpropyl]thiophene-2-sulfonamide |
|  | 3 | 2.5 |  |
|  | 20 | 3.3 |  |
|  | 20 | 5 |  |
|  | 20 | 3.8 |  |
|  | 1 | 1.5 |  |
| 9 | 10 | 1.81 | 5-bromo-N-[(1S)-1-(hydroxymethyl)-2-methylpropyl]thiophene-2-sulfonamide |
|  | 20 | 4.1 |  |
| 10 | 20 | 1.2 | 5-bromo-N-[(1R)-1-(hydroxymethyl)-2-methylpropyl]thiophene-2-sulfonamide |
|  | 20 | 6.4 |  |
|  | 20 | 1.7 |  |
| 11 | 20 | 2 | 4,5-dibromo-N-[(1S)-1-(hydroxymethyl)-2-methylpropyl]thiophene-2-sulfonamide |
|  | 20 | 4.9 |  |
| 12 | 3 | 3.07 | 5-chloro-N-[(1S)-1-cyclohexyl-2-hydroxyethyl]thiophene-2-sulfonamide |
|  | 1 | 2.58 |  |
|  | 10 | 4.2 |  |
|  | 20 | 4.3 |  |
|  | 3 | 3.1 |  |

TABLE 23-continued

| Ex # | Conc (µg/mL) | APPI Fold Increase | Name |
|---|---|---|---|
|  | 20 | 8.6 |  |
|  | 1 | 2 |  |
|  | 10 | 3.9 |  |
| 13 | 10 | 3.94 | 5-bromo-N-[(1S)-1-cyclohexyl-2- |
|  | 1 | 2.17 | hydroxyethyl]thiophene-2-sulfonamide |
|  | 3 | 4.02 |  |
| 14 | 10 | 3.45 | 5-chloro-N-[1-(hydroxymethyl)-2- |
|  | 3 | 1.87 | phenylpropyl]thiophene-2-sulfonamide |
|  | 3 | 3.33 |  |
| 15 | 10 | 3.08 | 5-bromo-N-[ 1 -(hydroxymethyl)-2- |
|  |  |  | phenylpropyl]thiophene-2-sulfonamide |
| 16 | 10 | 4.19 | 5-chloro-N-[(1S,2R)-1-(hydroxymethyl)-2- |
|  | 0.3 | 1.7 | methylbutyl]thiophene-2-sulfonamide |
|  | 1 | 1.9 |  |
|  | 3 | 3.1 |  |
|  | 20 | 3.7 |  |
|  | 20 | 14.2 |  |
|  | 20 | 4.8 |  |
|  | 20 | 3.2 |  |
|  | 20 | 5.6 |  |
|  | 20 | 6.1 |  |
|  | 10 | 3.2 |  |
|  | 1 | 2.56 |  |
|  | 3 | 4.47 |  |
| 17 | 1 | 2.38 | 5-bromo-N-[(1S,2R)-1-(hydroxymethyl)-2- |
|  | 3 | 3.47 | methylbutyl]thiophene-2-sulfonamide |
|  | 10 | 3.29 |  |
|  | 20 | 6.1 |  |
|  | 20 | 3.5 |  |
| 18 | 10 | 5.23 | 5-bromo-N-[(1S,2S)-1-(hydroxymethyl)-2- |
|  | 20 | 5.7 | methylbutyl]thiophene-2-sulfonamide 1,1-dioxide |
|  | 3 | 2.19 |  |
|  | 20 | 3 |  |
| 19 | 20 | 6 | 5-chloro-N-[1-(hydroxymethyl)-2,3- |
|  |  |  | dimethylpentyl]thiophene-2-sulfonamide |
| 20 | 20 | 5 | 5-chloro-N-[1-(hydroxymethyl)-2- |
|  |  |  | methylpentyl]thiophene-2-sulfonamide |
| 21 | 20 | 3.3 | 5-chloro-N-[2-ethyl-1- |
|  |  |  | (hydroxymethyl)hexyl]thiophene-2-sulfonamide |
| 22 | 20 | 7 | 5-chloro-N-[2-hydroxy-1-(2,4,6-trimethylcyclohex-3- |
|  |  |  | en-1-yl)ethyl]thiophene-2-sulfonamide |
| 23 | 20 | 6.4 | 5-chloro-N-(1-cyclohex-3-en-1-yl-2- |
|  |  |  | hydroxyethyl)thiophene-2-sulfonamide |
| 24 | 20 | 6 | 5-chloro-N-(1-cyclopentyl-2-hydroxyethyl)thiophene- |
|  |  |  | 2-sulfonamide |
| 25 | 20 | 7.5 | 5-bromo-N-[(1S)-1-(hydroxymethyl)-1,2- |
|  |  |  | dimethylpropyl]thiophene-2-sulfonamide |
| 26 | 20 | 5 | 5-chloro-N-[(1S)-1-(hydroxymethyl)-1,2- |
|  |  |  | dimethylpropyl]thiophene-2-sulfonamide |
| 27 | 20 | 8.7 | 5-chloro-N-[(1S,2R)-1-(hydroxymethyl)-2,4- |
|  |  |  | dimethylpentyl]thiophene-2-sulfonamide |
| 28 | 20 | 7 | 5-chloro-N-[(1S,2R)-1-(hydroxymethyl)-2-(4- |
|  |  |  | methoxyphenyl)propyl]thiophene-2-sulfonamide |
| 29 | 20 | 2.6 | 5-chloro-N-[(1S,2R)-1-(hydroxymethyl)-2- |
|  |  |  | methyloctyl]thiophene-2-sulfonamide |
| 30 | 20 | 6.7 | 5-chloro-N-[(1S)-2-ethyl-1- |
|  | 20 | 4.4 | (hydroxymethyl)butyl]thiophene-2-sulfonamide |
| 31 | 20 | 4.4 | 5-chloro-N-[(1S,2R)-2-ethyl-1-(hydroxymethyl)-4- |
|  |  |  | methylpentyl]thiophene-2-sulfonamide |
| 32 | 20 | 5 | 5-chloro-N-[(1S,2R)-1-(hydroxymethyl)-2-(4- |
|  |  |  | methoxyphenyl)butyl]thiophene-2-sulfonamide |
| 33 | 20 | 6.5 | 5-chloro-N-[(1S,2S)-1-(hydroxymethyl)-2- |
|  |  |  | methylpentyl]thiophene-2-sulfonamide |
| 34 | 20 | 5.9 | 5-chloro-N-[(1S,2S)-2-ethyl-1- |
|  |  |  | (hydroxymethyl)pentyl]thiophene-2-sulfonamide |
| 35 | 20 | 3.7 | 5-chloro-N-[(1S,2R)-1-(hydroxymethyl)-4-methyl-2- |
|  |  |  | propylpentyl]thiophene-2-sulfonamide |
| 36 | 20 | 3.8 | 5-chloro-N-[(1S,2R)-1-(hydroxymethyl)-2-(4- |
|  |  |  | methoxyphenyl)pentyl]thiophene-2-sulfonamide |
| 37 | 20 | 4.8 | 5-chloro-N-[(1S,2R)-1-(hydroxymethyl)-2- |
|  |  |  | propyloctyl]thiophene-2-sulfonamide |
| 38 | 20 | 4.1 | 5-chloro-N-[(1S,2R)-1-(hydroxymethyl)-2- |
|  |  |  | phenylpentyl]thiophene-2-sulfonamide |
| 39 | 20 | 5.7 | 5-chloro-N-[(1S,2S)-1-(hydroxymethyl)-2- |
|  |  |  | methylheptyl]thiophene-2-sulfonamide |

TABLE 23-continued

| Ex # | Conc (µg/mL) | APPI Fold Increase | Name |
|---|---|---|---|
| 40 | 20 | 3.9 | 5-chloro-N-[(1S)-2-propyl-1-(hydroxymethyl)pentyl]thiophene-2-sulfonamide |
| 41 | 20 | 4.7 | 5-chloro-N-[(1S,2S)-2-ethyl-1-(hydroxymethyl)heptyl]thiophene-2-sulfonamide |
| 42 | 20 | 3.4 | 5-chloro-N-[(1S,2R)-1-(hydroxymethyl)-2-isobutylheptyl]thiophene-2-sulfonamide |
| 43 | 20 | 1.7 | 5-chloro-N-[(1S,2R)-1-(hydroxymethyl)-2-(4-methoxyphenyl)heptyl]thiophene-2-sulfonamide |
| 44 | 20 | 1.6 | 5-chloro-N-[(1S,2R)-1-(hydroxymethyl)-2-pentyloctyl]thiophene-2-sulfonamide |
| 45 | 20 | 2.1 | 5-chloro-N-[(1S,2R)-1-(hydroxymethyl)-2-phenylheptyl]thiophene-2-sulfonamide |
| 46 | 20 | 5.8 | 5-chloro-N-[(1S,2S)-1-(hydroxymethyl)-2-phenylpropyl]thiophene-2-sulfonamide |
| 47 | 20 | 5.4 | 5-chloro-N-[(1S,2S)-1-(hydroxymethyl)-4-methyl-2-phenylpentyl]thiophene-2-sulfonamide |
| 48 | 20 | 4.7 | 5-chloro-N-[(1S,2R)-2-(2-furyl)-1-(hydroxymethyl)propyl]thiophene-2-sulfonamide |
| 49 | 20 | 6.1 | 5-chloro-N-[(1S,2R)-2-(2-furyl)-1-(hydroxymethyl)butyl]thiophene-2-sulfonamide |
| 50 | 20 | 7.7 | 5-chloro-N-[(1S,2R)-2-(2-furyl)-1-(hydroxymethyl)-4-methylpentyl]thiophene-2-sulfonamide |
| 51 | 20 | 4 | 5-chloro-N-[(1S,2R)-2-(2-furyl)-1-(hydroxymethyl)octyl]thiophene-2-sulfonamide |
| 52 | 20 | 7 | 5-chloro-N-[(1S,2S)-1-(hydroxymethyl)-2-isopropyloctyl]thiophene-2-sulfonamide |
| 53 | 20 | 3.9 | N-[(1S,2S)-2-[1,1'-biphenyl]-4-yl-1-(hydroxymethyl)propyl]-5-chlorothiophene-2-sulfonamide |
| 54 | 20 | 3.3 | N-[(1S,2S)-2-[1,1'-biphenyl]-4-yl-1-(hydroxymethyl)butyl]-5-chlorothiophene-2-sulfonamide |
| 55 | 20 | 1.9 | N-[(1S,2S)-2-[1,1'-biphenyl]-4-yl-1-(hydroxymethyl)-4-methylpentyl]-5-chlorothiophene-2-sulfonamide |
| 56 | 20 | 6.8 | 5-bromo-N-[(1S,2R)-1-(hydroxymethyl)-2,4-dimethylpentyl]thiophene-2-sulfonamide |
| 57 | 20 | 6.4 | 5-bromo-N-[(1S,2R)-1-(hydroxymethyl)-2-methyloctyl]thiophene-2-sulfonamide |
| 58 | 20 | 10 | 5-bromo-N-[(1S)-2-ethyl-1-(hydroxymethyl)butyl]thiophene-2-sulfonamide |
| 59 | 20 | 4.5 | 5-bromo-N-[(1S,2R)-2-ethyl-1-(hydroxymethyl)-4-methylpentyl]thiophene-2-sulfonamide |
| 60 | 20 | 6.9 | 5-bromo-N-[(1S,2S)-2-ethyl-1-(hydroxymethyl)pentyl]thiophene-2-sulfonamide |
| 61 | 20 | 5.7 | 5-bromo-N-[(1S,2R)-1-(hydroxymethyl)-4-methyl-2-propylpentyl]thiophene-2-sulfonamide |
| 62 | 20 | 4.5 | 5-bromo-N-[(1S,2S)-2-ethyl-1-(hydroxymethyl)heptyl]thiophene-2-sulfonamide |
| 63 | 20 | 3.3 | 5-bromo-N-[(1S,2R)-1-(hydroxymethyl)-2-isobutylheptyl]thiophene-2-sulfonamide |
| 64 | 20 | 2.9 | 5-bromo-N-[(1S,2R)-1-(hydroxymethyl)-2-(4-methoxyphenyl)heptyl]thiophene-2-sulfonamide |
| 65 | 20 | 1.9 | 5-bromo-N-[(1S,2R)-1-(hydroxymethyl)-2-pentyloctyl]thiophene-2-sulfonamide |
| 66 | 20 | 5.3 | 5-bromo-N-[(1S,2S)-1-(hydroxymethyl)-2-phenylpropyl]thiophene-2-sulfonamide |
| 67 | 20 | 4.7 | 5-bromo-N-[(1S,2S)-1-(hydroxymethyl)-2-phenylbutyl]thiophene-2-sulfonamide |
| 68 | 20 | 2.3 | 5-bromo-N-[(1S,2S)-1-(hydroxymethyl)-4-methyl-2-phenylpentyl]thiophene-2-sulfonamide |
| 69 | 20 | 1.5 | 5-bromo-N-[(1S,2S)-1-(hydroxymethyl)-4-methyl-2-pyridin-3-ylpentyl]thiophene-2-sulfonamide |
| 70 | 20 | 4.6 | 5-bromo-N-[(1S,2R)-2-(2-furyl)-1-(hydroxymethyl)propyl]thiophene-2-sulfonamide |
| 71 | 20 | 5.2 | 5-bromo-N-[(1S,2R)-2-(2-furyl)-1-(hydroxymethyl)butyl]thiophene-2-sulfonamide |
| 72 | 20 | 6.4 | 5-bromo-N-[(1S,2R)-2-(2-furyl)-1-(hydroxymethyl)-4-methylpentyl]thiophene-2-sulfonamide |
| 73 | 20 | 1.9 | 5-bromo-N-[(1S,2R)-2-(2-furyl)-1-(hydroxymethyl)octyl]thiophene-2-sulfonamide |
| 74 | 20 | 5.1 | 5-bromo-N-[(1S,2S)-2-ethyl-1-(hydroxymethyl)-3-methylbutyl]thiophene-2-sulfonamide |
| 75 | 20 | 4.7 | 5-bromo-N-[(1S,2S)-1-(hydroxymethyl)-2-isopropyl-4-methylpentyl]thiophene-2-sulfonamide |

TABLE 23-continued

| Ex # | Conc (μg/mL) | APPI Fold Increase | Name |
|---|---|---|---|
| 76 | 20 | 3.2 | N-[(1S,2S)-2-[1,1'-biphenyl]-4-yl-1-(hydroxymethyl)butyl]-5-bromothiophene-2-sulfonamide |
| 77A | 20 | 3.1 | 5-chloro-N-[(1S,2R)-2-ethyl-1-(hydroxymethyl)octyl]thiophene-2-sulfonamide |
| 77B | 20 | 16.9 | 5-chloro-N-[(1S,2S)-2-ethyl-1-(hydroxymethyl)octyl]thiophene-2-sulfonamide |
| 78A | 20 | 5.8 | 5-bromo-N-[(1S,2R)-2-ethyl-1-(hydroxymethyl)octyl]thiophene-2-sulfonamide |
| 78B | 20 | 23.0 | 5-bromo-N-[(1S,2S)-2-ethyl-1-(hydroxymethyl)octyl]thiophene-2-sulfonamide |
| 79 | 20 | 1.6 | 5-chloro-N-[(1S)-1-(hydroxymethyl)-2-(methylamino)butyl]-2-thiophenesulfonamide |
| 80 | 20 | 1.8 | 5-chloro-N-[(1S)-2-(ethylamino)-2-(hydroxymethyl)propyl]-2-thiophenesulfonamide |
| 81 | 20 | 1.5 | 5-chloro-N-[(1S)-2-[(2-hydroxyethyl)amino]-1-(hydroxymethyl)propyl]-2-thiophenesulfonamide |
| 82 | 20 | 2.2 | 5-chloro-N-[(1S)-2-[(2-hydroxyethyl)amino]-1-(hydroxymethyl)butyl]-2-thiophenesulfonamide |
| 83 | 20 | 1.7 | 5-chloro-N-[(1S)-2-[(2-hydroxyethyl)amino]-1-(hydroxymethyl)heptyl]-2-thiophenesulfonamide |
| 84 | 20 | 3.8 | N-[(1S)-2-(benzylamino)-1-(hydroxymethyl)propyl]-5-chloro-2-thiophenesulfonamide |
| 85 | 20 | 8.9 | N-[(1S)-2-(benzylamino)-1-(hydroxymethyl)butyl]-5-chloro-2-thiophenesulfonamide |
| 86 | 20 | 20 | 5-chloro-N-[(1S)-2-(cyclopentylamino)-1-(hydroxymethyl)propyl]-2-thiophenesulfonamide |
| 87 | 20 | 3.1 | 5-chloro-N-[(1S,2S)-1-(hydroxymethyl)-2-methylbutyl]-N-(2-phenoxyethyl)thiophene-2-sulfonamide |
| 88 | 20 | 4.9 | 5-chloro-N-(3-chlorobenzyl)-N-[(1S,2S)-1-(hydroxymethyl)-2-methylbutyl]thiophene-2-sulfonamide |
| 89 | 20 | 2.3 | 5-chloro-N-[(S)-2-hydroxy-1-phenylethyl]thiophene-2-sulfonamide |
| 90 | 10 | 3.82 | 5-chloro-N-[(S)-1-(hydroxymethyl)-3-methylbutyl]thiophene-2-sulfonamide |
|  | 20 | 3.6 |  |
|  | 3 | 1.74 |  |
| 91 | 20 | 2 | 5-chloro-N-[1-(hydroxymethyl)pentyl]thiophene-2-sulfonamide |
| 92 | 20 | 1.5 | 5-chloro-N-(2-hydroxy-1,1-dimethylethyl)thiophene-2-sulfonamide |
| 93 | 20 | 2 | N-[1,1-bis(hydroxymethyl)propyl]-5-chlorothiophene-2-sulfonamide |
| 94 | 10 | 2.4 | 5-chloro-N-[1-(hydroxymethyl)cyclopentyl]thiophene-2-sulfonamide |
|  | 20 | 2 |  |
|  | 20 | 3.4 |  |
|  | 20 | 2.2 |  |
|  | 20 | 2.2 |  |
|  | 20 | 5.8 |  |
| 95 | 10 | 1.9 | 5-chloro-N-[(S)-2-cyclohexyl-1-(hydroxymethyl)ethyl]thiophene-2-sulfonamide |
|  | 20 | 4.1 |  |
|  | 20 | 3.8 |  |
|  | 20 | 1.9 |  |
| 96 | 20 | 1.5 | N-[(S)-1-benzyl-2-hydroxyethyl]-5-chlorothiophene-2-sulfonamide |
| 97 | 20 | 1.8 | 5-chloro-N-[1-(hydroxymethyl)butyl]thiophene-2-sulfonamide |
| 98 | 10 | 2.43 | 5-chloro-N-[(S)-1-(hydroxymethyl)-2,2-dimethylpropyl]thiophene-2-sulfonamide |
|  | 20 | 2.8 |  |
|  | 20 | 4.9 |  |
|  | 20 | 2.4 |  |
| 99 | 20 | 1.5 | 5-chloro-N-[(R,R)-2-hydroxy-1-(hydroxymethyl)-2-(4-nitrophenyl)ethyl]thiophene-2-sulfonamide |
| 100 | 20 | 1.5 | 5-chloro-N-[(S)-1-(hydroxymethyl)propyl]thiophene-2-sulfonamide |
| 101 | 20 | 2.7 | N-[R-2-(benzylthio)-1-(hydroxymethyl)ethyl]-5-chlorothiophene-2-sulfonamide |
| 102 | 20 | 1.6 | N-[(R,S)-2-(benzyloxy)-1-(hydroxymethyl)propyl]-5-chlorothiophene-2-sulfonamide |
| 103 | 20 | 2.3 | 5-chloro-N-[(R,R)-2-hydroxy-1-(hydroxymethyl)propyl]thiophene-2-sulfonamide |
| 104 | 20 | 2.5 | 5-bromo-N-[(S)-2-hydroxy-1-phenylethyl]thiophene-2-sulfonamide |

TABLE 23-continued

| Ex # | Conc (μg/mL) | APPI Fold Increase | Name |
|---|---|---|---|
| 105 | 10 | 3.93 | 5-bromo-N-[(S)-1-(hydroxymethyl)-3-methylbutyl]thiophene-2-sulfonamide |
|  | 3 | 2.23 |  |
|  | 1 | 1.57 |  |
|  | 20 | 2.4 |  |
|  | 20 | 1.5 |  |
| 106 | 20 | 2.4 | 5-bromo-N-[1-(hydroxymethyl)pentyl]thiophene-2-sulfonamide |
| 107 | 20 | 1.5 | 5-bromo-N-(2-hydroxy-1,1-dimethylethyl)thiophene-2-sulfonamide |
| 108 | 20 | 2 | N-[1,1-bis(hydroxymethyl)propyl]-5-bromothiophene-2-sulfonamide |
| 109 | 10 | 2 | 5-bromo-N-[1-(hydroxymethyl)cyclopentyl]thiophene-2-sulfonamide |
|  | 3 | 1.8 |  |
|  | 20 | 2.5 |  |
|  | 20 | 1.7 |  |
|  | 20 | 2.7 |  |
|  | 20 | 4.3 |  |
|  | 20 | 4.8 |  |
| 110 | 10 | 1.71 | 5-bromo-N-[(S)-2-cyclohexyl-1-(hydroxymethyl)ethyl]thiophene-2-sulfonamide |
|  | 20 | 2.9 |  |
|  | 20 | 2.3 |  |
|  | 20 | 3.6 |  |
| 111 | 20 | 1.8 | 5-bromo-N-[(S)-1-(hydroxymethyl)-3-(methylthio)propyl]thiophene-2-sulfonamide |
| 112 | 20 | 1.6 | 5-bromo-N-[1-(hydroxymethyl)butyl]thiophene-2-sulfonamide |
| 113 | 10 | 2.86 | 5-bromo-N-[(S)-1-(hydroxymethyl)-2,2-dimethylpropyl]thiophene-2-sulfonamide |
|  | 20 | 3.7 |  |
|  | 20 | 1.7 |  |
|  | 20 | 3 |  |
| 114 | 20 | 1.8 | N-[R-2-(benzylthio)-1-(hydroxymethyl)ethyl]-5-bromothiophene-2-sulfonamide |
| 115 | 20 | 4.4 | 5-bromo-N-(R-2-hydroxy-1-{[(3-methylbenzyl)thio]methyl}ethyl)thiophene-2-sulfonamide |
| 116 | 20 | 2.2 | N-{(S)-1-[4-(benzyloxy)benzyl]-2-hydroxyethyl}-5-bromothiophene-2-sulfonamide |
| 117 | 20 | 2.6 | 5-bromo-N-[(R,R)-2-hydroxy-1-(hydroxymethyl)propyl]thiophene-2-sulfonamide |
| 118 | 20 | 4.8 | 5-chloro-N-[(S,S)-1-formyl-2-methylbutyl]thiophene-2-sulfonamide |
| 119 | 10 | 4.1 | 5-chloro-N-[(S,S)-1-(1-hydroxyethyl)-2-methylbutyl]thiophene-2-sulfonamide |
|  | 0.3 | 1.54 |  |
|  | 3 | 2.49 |  |
|  | 10 | 3.76 |  |
| 120 | 10 | 8.83 | 5-chloro-N-{(S,S)-1-[cyclopentyl(hydroxy)methyl]-2-methylbutyl}thiophene-2-sulfonamide |
|  | 10 | 5.24 |  |
|  | 3 | 1.9 |  |
| 121 | 10 | 1.74 | 5-chloro-N-{(S)-2-hydroxy-1-[(S)-1-methylpropyl]octyl}thiophene-2-sulfonamide |
|  | 10 | 1.5 |  |
|  | 10 | 1.56 |  |
| 122 | 10 | 1.68 | 5-chloro-N-{(S)-2-hydroxy-1-[(S)-1-methylpropyl]heptyl}thiophene-2-sulfonamide |
|  | 10 | 1.8 |  |
| 123 | 10 | 2.14 | 5-chloro-N-{(S)-2-hydroxy-1-[(S)-1-methylpropyl]hexyl}thiophene-2-sulfonamide |
|  | 10 | 1.76 |  |
| 124 | 10 | 2.32 | 5-chloro-N-{(S)-2-hydroxy-3-methyl-1-[(S)-1-methylpropyl]butyl}thiophene-2-sulfonamide |
|  | 10 | 2.42 |  |
| 125 | 10 | 6.52 | 5-chloro-N-{(S)-2-hydroxy-3,3-dimethyl-1-[(S)-1-methylpropyl]butyl}thiophene-2-sulfonamide |
|  | 3 | 1.58 |  |
|  | 10 | 3.94 |  |
| 126 | 10 | 5.25 | 5-chloro-N-{(S)-2-hydroxy-4-methyl-1-[(S)-1-methylpropyl]pentyl}thiophene-2-sulfonamide |
|  | 10 | 3.31 |  |
| 127 | 10 | 4.27 | 5-chloro-N-{(S)-2-hydroxy-1-[(S)-1-methylpropyl]but-3-enyl}thiophene-2-sulfonamide |
| 128 | 10 | 5.62 | 5-chloro-N-{(S)-2-hydroxy-1-[(S)-1-methylpropyl]pent-4-enyl}thiophene-2-sulfonamide |
|  | 1 | 1.52 |  |
|  | 20 | 5.9 |  |
|  | 3 | 2.48 |  |
|  | 10 | 3.86 |  |
| 129 | 10 | 7.43 | 5-chloro-N-{(S)-2-hydroxy-1-[(S)-1-methylpropyl]butyl}thiophene-2-sulfonamide |
|  | 3 | 1.61 |  |
|  | 10 | 4.59 |  |
| 130 | 10 | 1.85 | 5-chloro-N-{(S,S)-1-[(4-fluorophenyl)(hydroxy)methyl]-2-methylbutyl}thiophene-2-sulfonamide |

TABLE 23-continued

| Ex # | Conc (µg/mL) | APPI Fold Increase | Name |
|---|---|---|---|
| 131 | 10 | 3.64 | 5-chloro-N-{(S,S)-1-[(4-chlorophenyl)(hydroxy)methyl]-2-methylbutyl}thiophene-2-sulfonamide |
| 132 | 10 | 1.68 | 5-chloro-N-{(S)-2-hydroxy-4-methyl-1-[(S)-1-methylpropyl]pent-3-enyl}thiophene-2-sulfonamide |
| 133 | 10 | 2.51 | 5-chloro-N-{(S)-2-hydroxy-3-methyl-1-[(S)-1-methylpropyl]but-3-enyl}thiophene-2-sulfonamide |
|  |  | 1.68 |  |
| 134 | 10 | 2.42 | 5-chloro-N-{(S,S)-1-[hydroxy(4-methoxyphenyl)methyl]-2-methylbutyl}thiophene-2-sulfonamide |
| 135 | 10 | 1.93 | 5-chloro-N-{(S,E)-2-hydroxy-3-methyl-1-[(S)-1-methylpropyl]pent-3-enyl}thiophene-2-sulfonamide |
|  | 10 | 1.75 |  |
| 136 | 10 | 2.13 | 5-chloro-N-{(S)-4-(1,3-dioxan-2-yl)-2-hydroxy-1-[(S)-1-methylpropyl]butyl}thiophene-2-sulfonamide |
| 137 | 10 | 1.96 | 5-chloro-N-{(S)-2-hydroxy-1-[(S)-1-methylpropyl]hex-5-enyl}thiophene-2-sulfonamide |
| 138 | 10 | 3.54 | 5-chloro-N-((S,S)-1-{hydroxy[4-(methylthio)phenyl]methyl}-2-methylbutyl)thiophene-2-sulfonamide |
| 139 | 10 | 3.97 | 5-chloro-N-{(S,S)-1-[[4-(dimethylamino)phenyl](hydroxy)methyl]-2-methylbutyl}thiophene-2-sulfonamide |
| 140 | 10 | 2.57 | N-{(S,S)-1-[cyclopentyl(hydroxy)methyl]-2-methylbutyl}thiophene-2-sulfonamide |
| 141 | 10 | 4.2 | N-{(S)-2-hydroxy-1-[(S)-1-methylpropyl]octyl}thiophene-2-sulfonamide |
| 142 | 10 | 3.59 | N-{(S)-2-hydroxy-1-[(S)-1-methylpropyl]heptyl}thiophene-2-sulfonamide |
| 143 | 10 | 1.64 | N-{(S)-2-hydroxy-1-[(S)-1-methylpropyl]hexyl}thiophene-2-sulfonamide |
| 144 | 10 | 1.51 | N-{(S,S)-1-[hydroxy(2-methylphenyl)methyl]-2-methylbutyl}thiophene-2-sulfonamide |
| 145 | 10 | 1.72 | N-{(S)-2-hydroxy-3,3-dimethyl-1-[(S)-1-methylpropyl]butyl}thiophene-2-sulfonamide |
| 146 | 10 | 1.83 | N-{(S)-2-hydroxy-1-[(S)-1-methylpropyl]but-3-enyl}thiophene-2-sulfonamide |
| 147 | 10 | 2.04 | N-{(S)-2-hydroxy-1-[(S)-1-methylpropyl]pent-4-enyl}thiophene-2-sulfonamide |
| 148 | 10 | 1.52 | N-{(S)-2-hydroxy-1-[(S)-1-methylpropyl]butyl}thiophene-2-sulfonamide |
| 149 | 10 | 1.62 | N-{(S,S)-1-[hydroxy(4-methoxyphenyl)methyl]-2-methylbutyl}thiophene-2-sulfonamide |
| 150 | 10 | 1.6 | N-{(S)-4-(1,3-dioxan-2-yl)-2-hydroxy-1-[(S)-1-methylpropyl]butyl}thiophene-2-sulfonamide |
| 151 | 10 | 1.94 | N-{(S)-2-hydroxy-1-[(S)-1-methylpropyl]hex-5-enyl}thiophene-2-sulfonamide |
| 152 | 10 | 1.51 | N-{(S)-2-hydroxy-1-[(S)-1-methylpropyl]pent-3-ynyl}thiophene-2-sulfonamide |
| 153 | 10 | 2.09 | N-((S,S)-1-{hydroxy[4-(methylthio)phenyl]methyl}-2-methylbutyl)thiophene-2-sulfonamide |
| 154 | 10 | 4.23 | N-{(S,S)-1-[[4-dimethylamino)phenyl](hydroxy)methyl]-2-methylbutyl}thiophene-2-sulfonamide |
| 155 | 20 | 4.2 | 5-chloro-N-{(S,S)-1-[(S)-cyclohex-2-en-1-yl(hydroxy)methyl]-2-methylbutyl}thiophene-2-sulfonamide |
|  | 20 | 2.6 |  |
| 156 | 20 | 5.3 | 5-chloro-N-{(S,S,E)-2-hydroxy-1-[(S)-1-methylpropyl]hex-4-enyl}thiophene-2-sulfonamide |
|  | 20 | 5.9 |  |
| 157 | 20 | 6.7 | 5-chloro-N-{(S,R,E)-2-hydroxy-1-[(S)-1-methylpropyl]hex-4-enyl}thiophene-2-sulfonamide |
|  | 20 | 6.8 |  |
| 158 | 20 | 1.6 | 5-chloro-N-{(S,R,E)-2-hydroxy-1-[(S)-1-methylpropyl]hept-4-enyl}thiophene-2-sulfonamide |
|  | 20 | 5.4 |  |
| 159 | 20 | 3.8 | 5-chloro-N-{(S,S)-2-hydroxy-4-methyl-1-[(S)-1-methylpropyl]pent-4-enyl}thiophene-2-sulfonamide |
|  | 20 | 3.2 |  |
| 160 | 20 | 4 | 5-chloro-N-{(S,R)-2-hydroxy-4-methyl-1-[(S)-1-methylpropyl]pent-4-enyl}thiophene-2-sulfonamide |
|  | 20 | 3.3 |  |
| 161 | 20 | 2.6 | 5-chloro-N-{(S,E)-2-hydroxy-1-[(S)-1-methylpropyl]-5-phenylpent-4-enyl}thiophene-2-sulfonamide |
| 162 | 10 | 2.6 | 5-chloro-N-[(S,S)-1-(1-hydroxy-1-methylethyl)-2-methylbutyl]thiophene-2-sulfonamide |
| 163 | 10 | 3.3 | 5-chloro-N-{(S)-2-hydroxy-1-[(S)-1-methylpropyl]-2-pentylheptyl}thiophene-2-sulfonamide |
| 164 | 10 | 1.72 | 5-chloro-N-{(S,S)-1-[hydroxy(diphenyl)methyl]-2-methylbutyl}thiophene-2-sulfonamide |
| 165 | 10 | 1.73 | N-{(S)-2-allyl-2-hydroxy-1-[(S)-1-methylpropyl]pent-4-enyl}-5-chlorothiophene-2-sulfonamide |

TABLE 23-continued

| Ex # | Conc (μg/mL) | APPI Fold Increase | Name |
|---|---|---|---|
| 166 | 10 | 1.78 | 5-chloro-N-{(S)-2-ethyl-2-hydroxy-1-[(S)-1-methylpropyl]butyl}thiophene-2-sulfonamide |
| 167 | 10 | 3.42 | N-{(S,S)-1-[bis(4-chlorophenyl)(hydroxy)methyl]-2-methylbutyl}-5-chlorothiophene-2-sulfonamide |
| 168 | 10 | 5.87 | 5-chloro-N-{(S)-2-hydroxy-2-isopropenyl-3-methyl-1-[(S)-1-methylpropyl]but-3-enyl}thiophene-2-sulfonamide |
|  | 10 | 1.6 |  |
|  | 3 | 1.5 |  |
| 169 | 10 | 1.51 | 5-chloro-N-((S,S)-1-{hydroxy[bis(4-methoxyphenyl)]methyl}-2-methylbutyl)thiophene-2-sulfonamide |
| 170 | 10 | 1.95 | 5-chloro-N-{(S,E)-2-hydroxy-3-methyl-2-[(E)-1-methylprop-1-enyl]-1-[(S)-1-methylpropyl]pent-3-enyl}thiophene-2-sulfonamide |
| 171 | 10 | 5.32 | N-{(S)-2-but-3-enyl-2-hydroxy-1-[(S)-1-methylpropyl]hex-5-enyl}-5-chlorothiophene-2-sulfonamide |
| 172 | 10 | 2 | 5-chloro-N-((S,S)-1-{hydroxy[di(1-naphthyl)]methyl}-2-methylbutyl)thiophene-2-sulfonamide |
| 173 | 10 | 1.5 | 5-bromo-N-{(S)-2-ethyl-2-hydroxy-1-[(S)-1-methylpropyl]butyl}thiophene-2-sulfonamide |
| 174 | 10 | 1.75 | 5-bromo-N-{(S)-2-hydroxy-2-isopropenyl-3-methyl-1-[(S)-1-methylpropyl]but-3-enyl}thiophene-2-sulfonamide |
| 175 | 10 | 2.27 | 5-bromo-N-{(S,E)-2-hydroxy-3-methyl-2-[(E)-1-methylprop-1-enyl]-1-[(S)-1-methylpropyl]pent-3-enyl}thiophene-2-sulfonamide |
|  | 10 | 1.7 |  |
|  | 20 | 3.3 |  |
| 176 | 10 | 1.52 | 5-bromo-N-{(S)-2-but-3-enyl-2-hydroxy-1-[(S)-1-methylpropyl]hex-5-enyl}thiophene-2-sulfonamide |
| 177 | 20 | 5.1 | 5-chloro-N-[1-(hydroxymethyl)cyclohexyl]thiophene-2-sulfonamide |
|  | 20 | 3.7 |  |
| 178 | 20 | 2.3 | 5-chloro-N-[2-(hydroxymethyl)bicyclo[2.2.1]hept-2-yl]thiophene-2-sulfonamide |
| 179 | 20 | 8.3 | 5-chloro-N-[1-(hydroxymethyl)-2,3-dihydro-H-inden-1-yl]thiophene-2-sulfonamide |
| 180 | 20 | 2.3 | 5-chloro-N-[2-(hydroxymethyl)-2,3-dihydro-H-inden-2-yl]thiophene-2-sulfonamide |
| 181 | 20 | 2.6 | 5-bromo-N-[1-(hydroxymethyl)cyclohexyl]thiophene-2-sulfonamide |
| 182 | 20 | 4.2 | 5-bromo-N-[2-(hydroxymethyl)bicyclo[2.2.1]hept-2-yl]thiophene-2-sulfonamide |
| 183 | 20 | 3.7 | 5-bromo-N-[2-(hydroxymethyl)-2,3-dihydro-H-inden-2-yl]thiophene-2-sulfonamide |
| 184 | 20 | 3.7 | 5-chloro-N-{(S,S)-1-[(S)-1-hydroxyethyl]-2-methylbutyl}thiophene-2-sulfonamide |
|  | 20 | 2.7 |  |
| 185 | 20 | 2.4 | 5-chloro-N-{(S,S)-1-[R-1-hydroxyethyl]-2-methylbutyl}thiophene-2-sulfonamide |
|  | 20 | 5.4 |  |
| 186 | 20 | 6.3 | 5-chloro-N-{(S,S)-2-hydroxy-1-[(S)-1-methylpropyl]pentyl}thiophene-2-sulfonamide |
|  | 20 | 2.4 |  |
| 187 | 20 | 5.7 | 5-chloro-N-{(S,R)-2-hydroxy-1-[(S)-1-methylpropyl]pentyl}thiophene-2-sulfonamide |
|  | 20 | 3 |  |
| 188 | 20 | 6.3 | 5-chloro-N-{(S,S)-2-hydroxy-1-[(S)-1-methylpropyl]pent-4-enyl}thiophene-2-sulfonamide |
|  | 20 | 3.6 |  |
|  | 20 | 3.6 |  |
| 189 | 20 | 8.1 | 5-chloro-N-{(S,R)-2-hydroxy-1-[(S)-1-methylpropyl]pent-4-enyl}thiophene-2-sulfonamide |
|  | 20 | 7.9 |  |
|  | 20 | 7.2 |  |
|  | 20 | 4.4 |  |
| 190 | 20 | 4.4 | 5-bromo-N-{(S,S)-1-[(S)-1-hydroxyethyl]-2-methylbutyl}thiophene-2-sulfonamide |
|  | 20 | 2.6 |  |
| 191 | 20 | 5.4 | 5-bromo-N-{(S,S)-1-[R-1-hydroxyethyl]-2-methylbutyl}thiophene-2-sulfonamide |
|  | 20 | 4.8 |  |
| 192 | 20 | 2.2 | 5-bromo-N-{(S,S)-2-hydroxy-1-[(S)-1-methylpropyl]pentyl}thiophene-2-sulfonamide |
|  | 20 | 1.9 |  |
|  | 20 | 1.7 |  |
| 193 | 20 | 8.5 | 5-bromo-N-{(S,R)-2-hydroxy-1-[(S)-1-methylpropyl]pentyl}thiophene-2-sulfonamide |
|  | 20 | 4.5 |  |
|  | 20 | 3 |  |
| 194 | 20 | 9 | 5-bromo-N-{(S,S)-2-hydroxy-1-[(S)-1-methylpropyl]pent-4-enyl}thiophene-2-sulfonamide |
|  | 20 | 5.3 |  |
| 195 | 20 | 4.2 | 5-bromo-N-{(S,R)-2-hydroxy-1-[(S)-1-methylpropyl]pent-4-enyl}thiophene-2-sulfonamide |
|  | 20 | 6.7 |  |
| 196 | 20 | 20.7 | 5-chloro-N-[(S,S)-2-methyl-1-(2,2,2-trifluoro-1-hydroxyethyl)butyl]thiophene-2-sulfonamide |
| 197 | 20 | 3.4 | 5-chloro-N-[1-(1-hydroxybut-3-enyl)cyclohexyl]thiophene-2-sulfonamide |
|  | 20 | 1.8 |  |

TABLE 23-continued

| Ex # | Conc (μg/mL) | APPI Fold Increase | Name |
|---|---|---|---|
| 198 | 20 | 4.4 | 5-chloro-N-[1-(1-hydroxy-3-methylbut-3-enyl)cyclohexyl]thiophene-2-sulfonamide |
| 199 | 20 | 2.8 | 5-chloro-N-[(S)-2-hydroxy-1-(4-methoxycyclohexyl)ethyl]thiophene-2-sulfonamide |
| 199A | 20 | 2.4 | 5-Chloro-N-[(S)-2-hydroxy-1-(4-hydroxycyclohexyl)ethyl]thiophene-2-sulfonamide |
| 200 | 20 | 2 | 5-chloro-N-[(S)-2-hydroxy-1-(4-propoxycyclohexyl)ethyl]thiophene-2-sulfonamide |
| 201 | 20 | 2.2 | N-{(S)-1-[4-(allyloxy)cyclohexyl]-2-hydroxyethyl}-5-chlorothiophene-2-sulfonamide |
| 202 | 20 | 2 | N-{(S)-1-[4-(benzyloxy)cyclohexyl]-2-hydroxyethyl}-5-chlorothiophene-2-sulfonamide |
| 203 | 20 | 1.5 | N-[1-acetyl-4-(hydroxymethyl)piperidin-4-yl]-5-chlorothiophene-2-sulfonamide |
| 204 | 20 | 2.8 | 5-chloro-N-[(1S,2S)-1-(hydroxymethyl)-2-methylbutyl]-2-furansulfonamide |
|  | 20 | 2.5 |  |
| 205 | 20 | 2.6 | N[(1S)-2-butyl-1-(hydroxymethyl)hexyl]-5-chloro-2-thiophenesulfonamide |
| 206 | 20 | 1.8 | N-[(1S,2S)-1-(hydroxymethyl)-2-methylbutyl]-2-furansulfonamide |
| 207 | 20 | 5.6 | N-[(1S,2S)-1-(hydroxymethyl)-2-methylbutyl]-5-iodo-2-thiophenesulfonamide |
| 208 | 20 | 16.5 | 5-fluoro-N[(1S,2S)-1-(hydroxymethyl)-2-methylbutyl]-2-thiophenesulfonamide |
| 209 | 20 | 2.1 | 4-[1-(5-chloro-thiophene-2-sulfonylamino)-2-hydroxy-ethyl]-piperidine-1-carboxylic acid tert-butyl ester |
| 210 | 20 | 7.7 | N-[(1S,2S)-1-(hydroxymethyl)-2-methylbutyl]thiophene-2-sulfonamide |
| 211 | 20 | 1.9 | 5-chloro-N-[(S)-2-hydroxy-1-(4-benzylaminocyclohexyl)ethyl]thiophene-2-sulfonamide |
| 212 | 20 | 1.7 | 5-chloro-N-[(S)-2-hydroxy-1-(4-methylaminocyclohexyl)ethyl]thiophene-2-sulfonamide |
| 213 | 20 | 1.6 | 5-chloro-N-[(S)-2-hydroxy-1-(4-ethylaminocyclohexyl)ethyl]thiophene-2-sulfonamide |
| 214 | 20 | 2.1 | 5-chloro-N-[(S)-2-hydroxy-1-(4-npropylaminocyclohexyl)ethyl]thiophene-2-sulfonamide |
| 215 | 20 | 2.0 | 5-chloro-N-[(S)-2-hydroxy-1-(4-allylaminocyclohexyl)ethyl]thiophene-2-sulfonamide |
| 216 | 20 | 1.5 | 5-chloro-N-[(S)-2-hydroxy-1-(4-(3-pyridyl)methylaminocyclohexyl)ethyl]thiophene-2-sulfonamide |
| 217 | 20 | 1.8 | 5-chloro-N-[(S)-2-hydroxy-1-(4-morpholinocyclohexyl)ethyl]thiophene-2-sulfonamide |
| 218 | 20 | 2.8 | 5-chloro-N-[(S)-2-hydroxy-1-(4-(4-pyridyl)methylaminocyclohexyl)ethyl]thiophene-2-sulfonamide |
| 219 | 20 | 2.3 | 5-chloro-N-[(S)-2-hydroxy-1-(4-(2-pyridyl)methylaminocyclohexyl)ethyl]thiophene-2-sulfonamide |
| 220 | 20 | 2.5 | 5-chloro-N-[(S)-2-hydroxy-1-(4-(carboethoxymethyl)aminocyclohexyl)ethyl]thiophene-2-sulfonamide |
| 221 | 20 | 4.9 | 5-chloro-N-[(S)-2-ethyl-1-formylbutyl]thiophene-2-sulfonamide |
| 222 | 20 | 7.2 | 5-chloro-N-[(S)-2-ethyl-1-(1-hydroxyethyl)butyl]thiophene-2-sulfonamide |
|  | 20 | 9.7 |  |
| 223 | 20 | 5.6 | 5-chloro-N-[(S)-2-ethyl-1-(1-hydroxy-1-methylethyl)butyl]thiophene-2-sulfonamide |
|  | 20 | 8.4 |  |
| 224 | 20 | 7.2 | 5-chloro-N-(2-hydroxy-1-tetrahydro-H-thiopyran-4-ylethyl)thiophene-2-sulfonamide |
| 225 | 20 | 8.0 | 5-chloro-N-[(S)-2-hydroxy-1-piperidin-4-ylethyl]thiophene-2-sulfonamide |
| 226 | 20 | 7.6 | N-[(S)-2-ethyl-1-(hydroxymethyl)butyl]thiophene-2-sulfonamide |
| 227 | 20 | 26.3 | N-[(S)-2-ethyl-1-(hydroxymethyl)butyl]-5-fluorothiophene-2-sulfonamide |
| 228 | 20 | 9.9 | 5-chloro-N[(S)-1-(2,3-dihydro-H-inden-2-yl)-2-hydroxyethyl]thiophene-2-sulfonamide |
| 229 | 20 | 6.3 | 5-chloro-N-{(S,S)-1-[(Z)-(hydroxyimino)methyl]-2-methylbutyl}thiophene-2-sulfonamide |
| 230 | 20 | 4.8 | 5-chloro-N-{(S,S)-1-[(E)-(hydroxyimino)methyl]-2-methylbutyl}thiophene-2-sulfonamide |

What is claimed is:

1. A method of determining levels of β-amyloid in a subject, said method comprising:
(i) administering a compound of formula I to said subject, wherein said compound of formula I is of the structure:

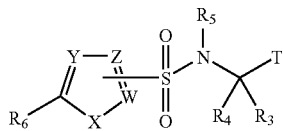

wherein:
R$_1$ and R$_2$ are independently selected from the group consisting of hydrogen, alkyl, substituted alkyl, CF$_3$, alkenyl, substituted alkenyl, alkynyl, substituted alkynyl, cycloalkyl, substituted cycloalkyl, phenyl, substituted phenyl, and (CH$_2$)$_n$(1,3)dioxane;
n is 2 to 5;
R$_3$ is selected from the group consisting of hydrogen, alkyl, and substituted alkyl;
R$_4$ is selected from the group consisting of hydrogen, alkyl, substituted alkyl, alkylcycloalkyl, substituted alkylcycloalkyl, phenyl(substituted)alkyl, alkylOH, substituted alkylOH, alkylOBn, substituted alkylOBn, alkylpyridyl, substituted alkylpyridyl, alkylfuranyl, substituted alkylfuranyl, CH(OH)phenyl, CH(OH)substituted phenyl, alkenyl, substituted alkenyl, cycloalkyl, substituted cycloalkyl, N-substituted-piperidinyl, piperidinyl, substituted piperidinyl, tetrahydrothiopyran, substituted tetrahydrothiopyran, 2-indane, substituted 2-indane, phenyl, substituted phenyl, alkylNHR$_7$, and substituted alkylNHR$_7$;
with the proviso that R$_3$ and R$_4$ are not both hydrogen;
R$_7$ is alkyl, substituted alkyl, cycloalkyl, substituted cycloalkyl, benzyl, substituted benzyl, alkylOH, substituted alkylOH, alkylSR$_8$, or substituted alkylSR$_8$;
R$_8$ is alkyl, substituted alkyl, benzyl, or substituted benzyl;
or R$_3$ and R$_4$ may be joined to form a ring;
R$_5$ is selected from the group consisting of hydrogen, lower alkyl, substituted lower alkyl, alkenyl, substituted alkenyl, alkynyl, substituted alkynyl, CH$_2$cycloalkyl, substituted CH$_2$cycloalkyl, beuzyl, substituted benzyl, and CH$_2$CH$_2$QR$_9$;
Q is O, NH or S;
R$_9$ is lower alkyl, substituted lower alkyl, phenyl, or substituted phenyl;
R$_6$ is selected from the group consisting of hydrogen, halogen and CF$_3$;
T is selected from the group consisting of

 and 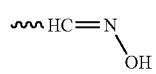

W, Y and Z are independently selected from the group consisting of C and CR$_{10}$;
R$_{10}$ is selected from the group consisting of hydrogen and halogen, with the proviso that at least one of W, Y and Z must be C;
X is selected from the group consisting of S;
R$_{11}$ is selected from the group consisting of hydrogen, lower alkyl, substituted lower alkyl, benzyl, substituted benzyl, phenyl, and substituted phenyl;
provided that when the compound contains one or more chiral centers, at least one of the chiral centers must be of S-stereochemistry;
(ii) assaying a sample from said subject.

2. The method according to claim 1, wherein said assaying comprises contacting said sample with an antibody to said compound of formula I.

3. The method according to claim 2, wherein said assay is an enzyme linked immunosorbent assay.

4. The method according to claim 2, wherein said assay is a radioimmunoassay.

5. The method according to claim 1, wherein the compound is selected from the group consisting of
3-bromo-5-chloro-N-[(1S,2S)-1-(hydroxymethyl)-2-methylbutyl]thiophene-2-sulfonamide;
5-bromo-N-[(1S,2S)-1-(hydroxymethyl)-2-methylbutyl]thiophene-2-sulfonamide;
4-bromo-5-chloro-N-[(1S,2S)-1-(hydroxymethyl)-2-methylbutyl]thiophene-2-sulfonamide;
5-chloro-N-[(1S,2S)-1-(hydroxymethyl)-2-methylbutyl]thiophene-2-sulfonamide;
2,5-dichloro-N-[(1S,2S)-1-(hydroxymethyl)-2methylbutyl]thiophene-3-sulfonamide;
4,5-dichloro-N-[(1S,2S)-1-(hydroxymethyl)-2-methylbutyl]thiophene-2-sulfonamide;
N-[(1S,2S)-1-(hydroxymethyl)-2-methylbutyl]thiophene-2-sulfonamide;
5-chloro-N-[(1S)-1-(hydroxymethyl)-2-methylpropyl]thiophene-2-sulfonamide;
5-bromo-N-[(1S)-1-(hydroxymethyl)-2-methylpropyl]thiophene-2-sulfonamide;
5-bromo-N-[(1R)-1-(hydroxymethyl)-2-methylpropyl]thiophene-2-sulfonamide;
4,5-dibromo-N-[(1S)-1-(hydroxymethyl)-2-methylpropyl]thiophene-2-sulfonamide;
5-chloro-N-[(1S)-1-cyclohexyl-2-hydroxyethyl]thiophene-2-sulfonamide;
5-bromo-N-[(1S)-1-cyclohexyl-2-hydroxyethyl]thiophene-2-sulfonamide;
5-chloro-N-[1-(hydroxymethyl)-2-phenylpropyl]thiophene-2-sulfonamide;
5-bromo-N-[1-(hydroxymethyl)-2-phenylpropyl]thiophene-2-sulfonamide;
5-chloro-N-[(1S,2R)-1-(hydroxymethyl)-2-methylbutyl]thiophene-2-sulfonamide;
5-bromo-N-[(1S,2R)-1-(hydroxymethyl)-2-methylbutyl]thiophene-2-sulfonamide;
5-bromo-N-[(1S,2S)-1-(hydroxymethyl)-2-methylbutyl]thiophene-2-sulfonamide 1,1-dioxide;
5-chloro-N-[1-(hydroxymethyl)-2,3-dimethylpentyl]thiophene-2-sulfonamide;
5-chloro-N-[1-(hydroxymethyl)-2-methylpentyl]thiophene-2-sulfonamide;
5-chloro-N-[2-ethyl-1-(hydroxymethyl)hexyl]thiophene-2-sulfonamide;
5-chloro-N-[2-hydroxy-1-(2,4,6-trimethylcyclohex-3-en-1-yl)ethyl]thiophene2-sulfonamide;

5-chloro-N-(1-cyclohex-3-en-1-yl-2-hydroxyethyl) thiophene-2-sulfonamide;
5-chloro-N-(1-cyclopentyl-2-hydroxyethyl)thiophene-2-sulfonamide;
5-bromo-N-[(1S)-1-(hydroxymethyl)-1,2-dimethylpropyl]thiophene-2-sulfonamide;
5-chloro-N-[(1S)-1-(hydroxymethyl)-1,2-dimethylpropyl]thiophene-2-sulfonamide;
5-chloro-N-[(1S,2R)-1-(hydroxymethyl)-2,4-dimethylpentyl]thiophene-2-sulfonamide;
5-chloro-N-[(1S,2R)-1-(hydroxymethyl)-2-(4-methoxyphenyl)propyl]thiophene-2-sulfonamide;
5-chloro-N-[(1S,2R)-1-(hydroxymethyl)-2-methyloctyl] thiophene-2-sulfonamide;
5-chloro-N-[(1S)-2-ethyl-1-(hydroxymethyl)butyl] thiophene-2-sulfonamide;
5-chloro-N-[(1S,2R)-2-ethyl-1-(hydroxymethyl)-4-methylpentyl]thiophene-2-sulfonamide;
5-chloro-N-[(1S,2R)-1-(hydroxymethyl)-2-(4-methoxyphenyl)butyl]thiophene-2-sulfonamide;
5-chloro-N-[(1S,2S)-1-(hydroxymethyl)-2-methylpentyl] thiophene-2-sulfonamide;
5-chloro-N-[(1S,2S)-2-ethyl-1-(hydroxymethyl)pentyl] thiophene-2-sulfonamide;
5-chloro-N-[(1S,2R)-1-(hydroxymethyl)-4-methyl-2-propylpentyl]thiophene-2-sulfonamide;
5-chloro-N-[(1S,2R)-1-(hydroxymethyl)-2-(4-methoxyphenyl)pentyl]thiophene-2-sulfonamide;
5-chloro-N-[(1S,2R)-1-(hydroxymethyl)-2-propyloctyl] thiophene-2-sulfonamide;
5-chloro-N-[(1S,2R)-1-(hydroxymethyl)-2-phenylpentyl] thiophene-2-sulfonamide;
5-chloro-N-[(1S,2S)-1-(hydroxymethyl)-2-methylheptyl] thiophene-2-sulfonamide;
5-chloro-N-[(1S)-2-propyl-1-(hydroxymethyl)pentyl] thiophene-2-sulfonamide;
5-chloro-N-[(1S,2S)-2-ethyl-1-(hydroxymethyl)heptyl] thiophene-2-sulfonamide;
5-chloro-N-[(1S,2R)-1-(hydroxymethyl)-2-isobutylheptyl]thiophene-2-sulfonamide;
5-chloro-N-[(1S,2R)-1-(hydroxymethyl)-2-(4-methoxyphenyl)heptyl]thiophene-2-sulfonamide;
5-chloro-N-[(1S,2R)-1-(hydroxymethyl)-2-pentyloctyl] thiophene-2-sulfonamide;
5-chloro-N-[(1S,2R)-1-(hydroxymethyl)-2-phenylheptyl] thiophene-2-sulfonamide;
5-chloro-N-[(1S,2S)-1-(hydroxymethyl)-2-phenylpropyl] thiophene-2-sulfonamide;
5-chloro-N-[(1S,2S)-1-(hydroxymethyl)-4-methyl-2-phenylpentyl]thiophene-2-sulfonamide;
5-chloro-N-[(1S,2R)-2-(2-furyl)-1-(hydroxymethyl)propyl]thiophene-2-sulfonamide;
5-chloro-N-[(1S,2R)-2-(2-furyl)-1-(hydroxymethyl)butyl]thiophene-2-sulfonamide;
5-chloro-N-[(1S,2R)-2-(2-furyl)-1-(hydroxymethyl)-4-methylpentyl]thiophene-2-sulfonamide;
5-chloro-N-[(1S,2R)-2-(2-furyl)-1-(hydroxymethyl)octyl]thiophene-2-sulfonamide;
5-chloro-N-[(1S,2S)1-(hydroxymethyl)-2-isopropyloctyl] thiophene-2-sulfonamide;
N-[(1S,2S)-2-[1,1'-biphenyl]-4-yl-1-(hydroxymethyl) propyl]-5-chlorothiophene-2-sulfonamide;
N-[(1S,2S)-2-[1,1'-biphenyl]-4-yl-1-(hydroxymethyl)butyl]-5-chlorothiophene-2-sulfonamide;
N-[(1S,2S)-2-[1,1'-biphenyl]-4-yl-1-(hydroxymethyl)-4-methylpentyl]-5-chlorothiophene-2-sulfonamide;
5-bromo-N-[(1S,2R)-1-(hydroxymethyl)-2,4-dimethylpentyl]thiophene-2-sulfonamide;
5-bromo-N-[(1S,2R)-1-(hydroxymethyl)-2-methyloctyl] thiophene-2-sulfonamide;
5-bromo-N-[(1S)-2-ethyl-1-(hydroxymethyl)butyl] thiophene-2-sulfonamide;
5-bromo-N-[(1S,2R)-2-ethyl-1-(hydroxymethyl)-4-methylpentyl]thiophene-2-sulfonamide;
5-bromo-N-[(1S,2S)-2-ethyl-1-(hydroxymethyl)pentyl] thiophene-2-sulfonamide;
5-bromo-N-[(1S,2R)-1-(hydroxymethyl)-4-methyl-2-propylpentyl]thiophene-2-sulfonamide;
5-bromo-N-[(1S,2S)-2-ethyl-1-(hydroxymethyl)heptyl] thiophene-2-sulfonamide;
5-bromo-N-[(1S,2R)-1-(hydroxymethyl)-2-isobutylheptyl]thiophene-2-sulfonamide;
5-bromo-N-[(1S,2R)-1-(hydroxymethyl)-2-(4-methoxyphenyl)heptyl]thiophene-2-sulfonamide;
5-bromo-N-[(1S,2R)-1-(hydroxymethyl)-2-pentyloctyl] thiophene-2-sulfonamide;
5-bromo-N-[(1S,2S)-1-(hydroxymethyl)-2-phenylpropyl] thiophene-2-sulfonamide;
5-bromo-N-[1S,2S)-1-(hydroxymethyl)-2-phenylbutyl] thiophene-2-sulfonamide;
5-bromo-N-[(1S,2S)-1-(hydroxymethyl)-4-methyl-2-phenylpentyl]thiophene-2-sulfonamide;
5-bromo-N-[(1S,2S)-1-(hydroxymethyl)-4-methyl-2-pyridin-3-ylpentyl]thiophene-2-sulfonamide;
5-bromo-N-[(1S,2R)-2-(2-furyl)-1-(hydroxymethyl)propyl]thiophene-2-sulfonamide;
5-bromo-N-[(1S,2R)-2-(2-furyl)-1-(hydroxymethyl)butyl]thiophene-2-sulfonamide;
5-bromo-N-[(1S,2R)-2-(2-furyl)-1-(hydroxymethyl)-4-methylpentyl]thiophene-2-sulfonamide;
5-bromo-N-[(1S,2R)-2-(2-furyl)-1-(hydroxymethyl)octyl]thiophene-2-sulfonamide;
5-bromo-N-[(1S,2S)-2-ethyl-1-(hydroxymethyl)-3-methylbutyl]thiophene-2-sulfonamide;
5-bromo-N-[(1S,2S)-1-(hydroxymethyl)-2-isopropyl-4-methylpentyl]thiophene-2-sulfonamide;
N-[(1S,2S)-2-[1,1'-biphenyl]-4-yl-1-(hydroxymethyl)butyl]-5-bromothiophene-2-sulfonamide;
5-chloro-N-[(1S,2S)-2-ethyl-1-(hydroxymethyl)octyl] thiophene-2-sulfonamide;
5-chloro-N-[(1S,2S)-2-ethyl-1-(hydroxymethyl)octyl] thiophene-2-sulfonamide;
5-bromo-N-[(1S,2R)-2-ethyl-1-(hydroxymethyl)octyl] thiophene-2-sulfonamide;
5-bromo-N-[(1S,2S)-2-ethyl-1-(hydroxymethyl)octyl] thiophene-2-sulfonamide;
5-chloro-N-[(1S)-1-(hydroxymethyl)-2-(methylamino) butyl]2thiophenesulfonamide;
5-chloro-N-[(1S)-2-(ethylamino)-2-(hydroxymethyl)propyl]-2-thiophenesulfonamide;
5-chloro-N-[(1S)-2-[(2-hydroxyethyl)amino]-1-(hydroxymethyl)propyl]-2-thiophenesulfonamide;
5-chloro-N-[(1S)-2-[(2-hydroxyethyl)amino]-1-(hydroxymethyl)butyl]-2-thiophenesulfonamide;
5-chloro-N-[(1S)-2-[(2-hydroxyethyl)amino]-1-(hydroxymethyl)heptyl]-2-thiophenesulfonamide;
N-[(1S)-2-(benzylamino)-1-(hydroxymethyl)propyl]-5-chloro-2-thiophenesulfonamide;
N-[(1S)-2-(benzylamino)-1-(hydroxymethyl)butyl]-5-chloro-2-thiophenesulfonamide;
5-chloro-N-[(1S)-2-(cyclopentylamino)-1-(hydroxymethyl)propyl]-2-thiophenesulfonamide;

5-chloro-N-[(1S,2S)-1-(hydroxymethyl)-2-methylbutyl]-N-(2-phenoxyethyl)thiophene-2-sulfonamide;
5-chloro-N-(3-chlorobenzyl)-N-[(1S,2S)-1-(hydroxymethyl)-2-methylbutyl]thiophene-2-sulfonamide;
5-chloro-N-[(S)-2-hydroxy-1-phenylethyl]thiophene-2-sulfonamide;
5-chloro-N-[(S)-1-(hydroxymethyl)-3-methylbutyl]thiophene-2-sulfonamide;
5-chloro-N-[1-(hydroxymethyl)pentyl]thiophene-2-sulfonamide;
5-chloro-N-(2-hydroxy-1,1-dimethylethyl)thiophene-2-sulfonamide;
N-[1,1-bis(hydroxymethyl)propyl]-5-chlorothiophene-2-sulfonamide;
5-chloro-N-[1-(hydroxymethyl)cyclopentyl]thiophene-2-sulfonamide;
5-chloro-N-[(S)-2-cyclohexyl-1-(hydroxymethyl)ethyl]thiophene-2-sulfonamide;
N-[(S)-1-benzyl-2-hydroxyethyl]-5-chlorothiophene-2-sulfonamide;
5-chloro-N-[1-(hydroxymethyl)butyl]thiophene-2-sulfonamide;
5-chloro-N-[(S)-1-(hydroxymethyl)-2,2-dimethylpropyl]thiophene-2-sulfonamide;
5-chloro-N-[(R,R)-2-hydroxy-1-(hydroxymethyl)-2-(4-nitrophenyl)ethyl]thiophene-2-sulfonamide;
5-chloro-N-[(S)-1-(hydroxymethyl)propyl]thiophene-2-sulfonamide;
N-[R-2-(benzylthio)-1-(hydroxymethyl)ethyl]-5-chlorothiophene-2-sulfonamide;
N-[(R,S)-2-(benzyloxy)-1-(hydroxymetyl)propyl]-5-chlorothiophene-2-sulfonamide;
5-chloro-N-[(R,R)-2-hydroxy-1-(hydroxymethyl)propyl]thiophene-2-sulfonamide;
5-bromo-N-[(S)-2-hydroxy-1-phenylethyl]thiophene-2-sulfonamide;
5-bromo-N-[(S)-1-(hydroxymethyl)-3-methylbutyl]thiophene-2-sulfonamide;
5-bromo-N-[1-(hydroxymethyl)pentyl]thiophene-2-sulfonamide;
5-bromo-N-(2-hydroxy-1,1-dimethylethyl)thiophene-2-sulfonamide;
N-[1,1-bis(hydroxymethyl)propyl]-5-bromothiophene-2-sulfonamide
5-bromo-N-[1-(hydroxymethyl)cyclopentyl]thiophene-2-sulfonamide
5-bromo-N-[(S)-2-cyclohexyl-1-(hydroxymethyl)ethyl]thiophene-2-sulfonamide;
5-bromo-N-[(S)-1-(hydroxymethyl)-3-(methylthio)propyl]thiophene-2-sulfonamide;
5-bromo-N-[1-(hydroxymethyl)butyl]thiophene-2-sulfonamide;
5-bromo-N-[(S)-1-(hydroxymethyl)-2,2-dimothylpropyl]thiophene-2-sulfonamide;
N-[R-2-(benzylthio)-1-(hydroxymethyl)ethyl]-5-bromothiophene-2-sulfonamide;
5-bromo-N-(R-2-hydroxy-1-{[(3-metylbenzyl)thio]methyl}ethyl)thiophene-2-sulfonamide;
N-{(S)-1-[4-(benzyloxy)benzyl]-2-hydroxyethyl}-5-bromothiophene-2-sulfonamide;
5-bromo-N-[(R,R)-2-hydroxy-1-(hydroxymethyl)propyl]thiophene-2-sulfonamide;
5-chloro-N-[(S,S)-1-(1-hydroxyethyl)-2-methylbutyl]thiophene-2-sulfonamide;
5-chloro-N-{(S,S)-1-[cyclopentyl(hydroxy)methyl]-2-methylbutyl}thiophene-2-sulfonamide;
5-chloro-N-{(S)-2-hydroxy-1-[(S)-1-methylpropyl]octyl}thiophene-2-sulfonamide;
5-chloro-N-{(S)-2-hydroxy-1-[(S)-1-methylpropyl]heptyl}thiophene-2-sulfonamide;
5-chloro-N-{(S)-2-hydroxy-1-[(S)-1-methylpropyl]hexyl}thiophene-2-sulfonamide;
5-chloro-N-{(S)-2-hydroxy-3-methyl-1-[(S)-1-methylpropyl]butyl}thiophene-2-sulfonamide;
5-chloro-N-{(S)-2-hydroxy-3,3-dimethyl-1-[(S)-1-methylpropyl]butyl}thiophene-2-sulfonamide;
5-chloro-N-{(S)-2-hydroxy-4-methyl-1-[(S)-1-methylpropyl]pentyl}thiophene-2-sulfonamide;
5-chloro-N-{(S)-2-hydroxy-1-[(S)-1-methylpropyl]but-3-enyl}thiophene-2-sulfonamide;
5-chloro-N-{(S)-2-hydroxy-1-[(S)-1-methylpropyl]pent-4-enyl}thiophene-2-sulfonamide;
5-chloro-N-{(S)-2-hydroxy-1-[(S)-1-methylpropyl]butyl}thiophene-2-sulfonamide;
5-chloro-N-{(S,S)-1-[(4-fluorophenyl)(hydroxy)methyl]-2-methylbutyl}thiophene-2-sulfonamide;
5-chloro-N-{(S,S)-1-[(4-chlorophenyl)(hydroxy)methyl]-2-methylbutyl}thiophene-2-sulfonamide;
5-chloro-N-{(S)-2-hydroxy-4-methyl-1-[(S)-1-methylpropyl]pent-3-enyl}thiophene-2-sulfonamide;
5-chloro-N-{(S)-2-hydroxy-3-methyl-1-[(S)-1-methylpropyl]but-3-enyl}thiophene-2-sulfonamide;
5-chloro-N-{(S,S)-1-[hydroxy(4-methoxyphenyl)methyl]-2-methylbutyl}thiophene-2-sulfonamide;
5-chloro-N-{(S,E)-2-hydroxy-3-methyl-1-[(S)-1-methylpropyl]pent-3-enyl}thiophene-2-sulfonamide;
5-chloro-N-{(S)-4-(1,3-dioxan-2-yl)-2-hydroxy-1-[(S)-1-methylpropyl]butyl}thiophene-2-sulfonamide;
5-chloro-N-{(S)-2-hydroxy-1-[(S)-1-methylpropyl]hex-5-enyl}thiophene-2-sulfonamide;
5-chloro-N-((S,S)-1-{hydroxy[4-(methylthio)phenyl]methyl}-2-methylbutyl)thiophene-2-sulfonamide;
5-chloro-N-{(S,S)-1-[[4-(dimethylamino)phenyl](hydroxy)methyl]-2-methylbutyl}thiophene-2-sulfonamide;
N-{(S,S)-1-[cyclopentyl(hydroxy)methyl]-2-methylbutyl}thiophene-2-sulfonamide;
N-{(S)-2-hydroxy-1-[(S)-1-methylpropyl]octyl}thiophene-2-sulfonamide;
N-{(S)-2-hydroxy-1-[(S)-1-methylpropyl]heptyl}thiophene-2-sulfonamide;
N-{(S)-2-hydroxy-1-[(S)-1-methylpropyl]hexyl}thiophene-2-sulfonamide;
N-{(S,S)-1-[hydroxy(2-methylphenyl)methyl]-2-methylbutyl}thiophene-2-sulfonamide;
N-{(S)-2-hydroxy-3,3-dimethyl-1-[(S)-1-methylpropyl]butyl}thiophene-2-sulfonamide;
N-{(S)-2-hydroxy-1-[(S)-1-methylpropyl]but-3-enyl}thiophene-2-sulfonamide;
N-{(S)-2-hydroxy-1-[(S)-1-methylpropyl]pent-4-enyl}thiophene-2-sulfonamide;
N-{(S)-2-hydroxy-1-[(S)-1-methylpropyl]butyl}thiophene-2-sulfonamide;
N-{(S,S)-1-[hydroxy(4-methoxyphenyl)methyl]-2-methylbutyl}thiophene-2-sulfonamide;
N-{(S)-4-(1,3-dioxan-2-yl)-2-hydroxy-1-[(S)-1-methylpropyl]butyl}thiophene-2-sulfonamide;
N-{(S)-2-hydroxy-1-[(S)-1-methylpropyl]hex-5-enyl}thiophene-2-sulfonamide;
N-{(S)-2-hydroxy-1-[(S)-1-methylpropyl]pent-3-ynyl}thiophene-2-sulfonamide;
N-((S,S)-1-{hydroxy[4-(methylthio)phenyl]methyl}-2-methylbutyl)thiophene-2-sulfonamide;

N-{(S,S)-1-[[4-(dimethylamino)phenyl](hydroxy)methyl]-2-methylbutyl}thiophene-2-sulfonamide;
5-chloro-N-{(S,S)-1-[(S)-cyclohex-2-en-1-yl(hydroxy)methyl]-2-methylbutyl}thiophene-2-sulfonamide;
5-chloro-N-{(S,S,E)-2-hydroxy-1-[(S)-1-methylpropyl]hex-4-enyl}thiophene-2-sulfonamide;
5-chloro-N-{(S,R,E)-2-hydroxy-1-[(S)-1-methylpropyl]hex-4-enyl}thiophene-2-sulfonamide;
5-chloro-N-{(S,R,E)-2-hydroxy-1-[(S)-1-methylpropyl]hept-4-enyl}thiophene-2-sulfonamide;
5-chloro-N-{(S,S)-2-hydroxy-4-methyl-1-[(S)-1-methylpropyl]pent-4-enyl}thiophene-2-sulfonamide;
5-chloro-N-{(S,R)-2-hydroxy-4-methyl-1-[(S)-1-methylpropyl]pent-4-enyl}thiophene-2-sulfonamide;
5-chloro-N-{(S,E)-2-hydroxy-1-[(S)-1-methylpropyl]-5-phenylpent-4-enyl}thiophene-2-sulfonamide;
5-chloro-N-[(S,S)-1-(1-hydroxy-1-methylethyl)-2-methylbutyl]thiophene-2-sulfonamide;
5-chloro-N-{(S)-2-hydroxy-1-[(S)-1-methylpropyl]-2-pentylheptyl}thiophene-2-sulfonamide;
5-chloro-N-{(S,S)-1-[hydroxy(diphenyl)methyl]-2-methylbutyl}thiophene-2-sulfonamide;
N-{(S)-2-allyl-2-hydroxy-1-[(S)-1-methylpropyl]pent-4-enyl}-5-chlorothiophene-2-sulfonamide;
5-chloro-N-{(S)-2-ethyl-2-hydroxy-1-[(S)-1-methylpropyl]butyl}thiophene-2-sulfonamide;
N-{(S,S)-1-[bis(4-chlorophenyl)(hydroxy)methyl]-2-methylbutyl}-5-chlorothiophene-2-sulfonamide;
5-chloro-N-{(S)-2-hydroxy-2-isopropenyl-3-methyl-1-[(S)-1-methylpropyl]but-3-enyl}thiophene-2-sulfonamide;
5-chloro-N-((S,S)-1-{hydroxy[bis(4-methoxyphenyl)]methyl}-2-methylbutyl)thiophene-2-sulfonamide;
5-chloro-N-{(S,E)-2-hydroxy-3-methyl-2-[(E)-1-methylprop-1-enyl]-1-[(S)-1-methylpropyl]pent-3-enyl}thiophene-2-sulfonamide;
N-{(S)-2-but-3-enyl-2-hydroxy-1-[(S)-1-methylpropyl]hex-5-enyl}-5-chlorothiophene-2-sulfonamide;
5-chloro-N-((S,S)-1-{hydroxy[di(1-naphthyl)]methyl}-2-methylbutyl)thiophene-2-sulfonamide;
5-bromo-N-{(S)-2-ethyl-2-hydroxy-1-[(S)-1-methylpropyl]butyl}thiophene-2-sulfonamide;
5-bromo-N-{(S)-2-hydroxy-2-isopropenyl-3-methyl-1-[(S)-1-methylpropyl]but-3-enyl}thiophene-2-sulfonamide;
5-bromo-N-{(S,E)-2-hydroxy-3-methyl-2-[(E)-1-methylprop-1-enyl]-1-[(S)-1-methylpropyl]pent-3-enyl}thiophene-2-sulfonamide;
5-bromo-N-{(S)-2-but-3-enyl-2-hydroxy-1-[(S)-1-methylpropyl]hex-5-enyl}thiophene-2-sulfonamide;
5-chloro-N-[1-(hydroxymethyl)cyclohexyl]thiophene-2-sulfonamide;
5-chloro-N-[2-(hydroxymethyl)bicyclo[2.2.1]hept-2-yl]thiophene-2-sulfonamide;
5-chloro-N-[1-(hydroxymethyl)-2,3-dihydro-H-inden-1-yl]thiophene-2-sulfonamide;
5-chloro-N-[2-(hydroxymethyl)-2,3-dihydro-H-inden-2-yl]thiophene-2-sulfonamide;
5-bromo-N-[1-(hydroxymethyl)cyclohexyl]thiophene-2-sulfonamide   5-bromo-N-[2-(hydroxymethyl)bicyclo[2.2.1]hept-2-yl]thiophene-2-sulfonamide;
5-bromo-N-[2-(hydroxymethyl)-2,3-dihydro-H-inden-2-yl]thiophene-2-sulfonamide;
5-chloro-N-{(S,S)-1-[(S)-1-hydroxyethyl]-2-methylbutyl}thiophene-2-sulfonamide;
5-chloro-N-{(S,S)-1-[R-1-hydroxyethyl]-2-methylbutyl}thiophene-2-sulfonamide;
5-chloro-N-{(S,S)-2-hydroxy-1-[(S)-1-methylpropyl]pentyl}thiophene-2-sulfonamide;
5-chloro-N-{(S,R)-2-hydroxy-1-[(S)-1-methylpropyl]pentyl}thiophene-2-sulfonamide;
5-chloro-N-{(S,S)-2-hydroxy-1-[(S)-1-methylpropyl]pent-4-enyl}thiophene-2-sulfonamide;
5-chloro-N-{(S,R)-2-hydroxy-1-[(S)-1-methylpropyl]pent-4-enyl}thiophene-2-sulfonamide;
5-bromo-N-{(S,S)-1-[(S)-1-hydroxyethyl]-2-methylbutyl}thiophene-2-sulfonamide;
5-bromo-N-{(S,S)-1-[R-1-hydroxyethyl]-2-methylbutyl}thiophene-2-sulfonamide;
5-bromo-N-{(S,S)-2-hydroxy-1-[(S)-1-methylpropyl]pentyl}thiophene-2-sulfonamide;
5-bromo-N-{(S,R)-2-hydroxy-1-[(S)-1-methylpropyl]pentyl}thiophene-2-sulfonamide;
5-bromo-N-{(S,S)-2-hydroxy-1-[(S)-1-methylpropyl]pent-4-enyl}thiophene-2-sulfonamide;
5-bromo-N-{(S,R)-2-hydroxy-1-[(S)-1-methylpropyl]pent-4-enyl}thiophene-2-sulfonamide;
5-chloro-N-[(S,S)-2-methyl-1-(2,2,2-trifluoro-1-hydroxyethyl)butyl]thiophene-2-sulfonamide;
5-chloro-N-[1-(1-hydroxybut-3-enyl)cyclohexyl]thiophene-2-sulfonamide;
5-chloro-N-[1-(1-hydroxy-3-methylbut-3-enyl)cyclohexyl]thiophene-2-sulfonamide;
5-chloro-N-[(S)-2-hydroxy-1-(4-methoxycyclohexyl)ethyl]thiophene-2-sulfonamide;
5-chloro-N-[(S)-2-hydroxy-1-(4-propoxycyclohexyl)ethyl]thiophene-2-sulfonamide;
N-{(S)-1-[4-(allyloxy)cyclohexyl]-2-hydroxyethyl}-5-chlorothiophene-2-sulfonamide;
N-{(S)-1-[4-(benzyloxy)cyclohexyl]-2-hydroxyethyl}-5-chlorothiophene-2-sulfonamide;
N-[1-acetyl-4-(hydroxymethyl)piperidin-4-yl]-5-chlorothiophene-2-sulfonamide;
N-[(1S)-2-butyl-1-(hydroxymethyl)hexy]-5-chloro-2-thiophenesulfonamide;
N-[(1S,2S)-1-(hydroxymethyl)-2-methylbutyl]-5-iodo-2-thiophenesulfonamide;
5-fluoro-N-[(1S,2S)-1-(hydroxymethyl)-2-methylbutyl]-2-thiophenesulfonamide;
N-[(1S,2S)-1-(hydroxymethyl)-2-methylbutyl]thiophene2sulfonamide;
5-chloro-N-[(S)-2-hydroxy-1-(4-benzylaminocyclohexyl)ethyl]thiophene-2-sulfonamide;
5-chloro-N-[(S)-2-hydroxy-1-(4-methylaminocyclohexyl)ethyl]thiophene-2-sulfonamide;
5-chloro-N-[(S)-2-hydroxy-1-(4-ethylaminocyclohexyl)ethyl]thiophene-2-sulfonamide;
5-chloro-N-[(S)-2-hydroxy-1-(4-npropylaminocyclohexyl)ethyl]thiophene-2-sulfonamide;
5-chloro-N-[(S)-2-hydroxy-1-(4-allylaminocyclohexyl)ethyl]thiophene-2-sulfonamide;
5-chloro-N-[(S)-2-hydroxy-1-(4-(3-pyridyl)methylaminocyclohexyl)ethyl]thiophene-2-sulfonamide;
5-chloro-N-[(S)-2-hydroxy-1-(4-morpholinocyclohexyl)ethyl]thiophene-2-sulfonamide;
5-chloro-N-[(S)-2-hydroxy-1-(4-(4-pyridyl)methylaminocyclohexyl)ethyl]thiophene-2-sulfonamide;
5-chloro-N-[(S)-2-hydroxy-1-(4-(2-pyridyl)methylaminocyclohexyl)ethyl]thiophene-2-sulfonamide;
5-chloro-N-[(S)-2-hydroxy-1-(4-(carboethoxymethyl)aminocyclohexyl)ethyl]thiophene-2sulfonamide;
5-chloro-N-[(S)-2-hydroxy-1-(4-hydroxycyclohexyl)ethyl]thiophene-2-sulfonamide 5-chloro-N-[(S)-2-ethyl-1-(1-hydroxyethyl)butyl]thiophene-2-sulfonamide;

5-chloro-N-[(S)-2-ethyl-1-(1-hydroxy-1-methylethyl)butyl]thiophene-2-sulfonamide;

5-chloro-N-(2-hydroxy-1-tetrahydro-H-thiopyran-4-yl-ethyl)thiophene-2-sulfonamide;

5-chloro-N-[(S)-2-hydroxy-1-piperidin-4-ylethyl]thiophene-2-sulfonamide;

N-[(S)-2-ethyl-1-(hydroxymethyl)butyl]thiophene-2-sulfonamide;

N-[(S)-2-ethyl-1-(hydroxymethyl)butyl]-5-fluorothiophene-2-sulfonamide;

5-chloro-N-[(S)-1-(2,3-dihydro-H-inden-2-yl)-2-hydroxyethyl]thiophene-2-sulfonamide;

5-chloro-N-{(S,S)-1-[(Z)-(hydroxyimino)methyl]-2-methylbutyl}thiophene-2-sulfonamide; and 5-chloro-N-{(S,S)-1-[(E)-(hydroxyimino)methyl]-2-methylbutyl}thiophene-2-sulfonamide.

6. The method according to claim 1, wherein the compound is 4-[1-(5-chloro-thiophene-2-sulfonylamino)-2hydroxyethyl]-piperidine-1-carboxylic acid tert-butyl ester.

7. The method according to claim 1, wherein $R_6$ is halogen, $R_4$ is lower alkyl of S-stereochemistry, $R_3$ is hydrogen, $R_5$ is hydrogen, and $R_1$ and $R_2$ are each hydrogen.

8. The method according to claim 1, wherein $R_6$ is halogen.

9. The method according to claim 1, wherein T is C(OH)$R_1R_2$ and $R_1$ and $R_2$ are each hydrogen.

10. The method according to claim 1, wherein W and Z are both C.

11. The method according to claim 1, wherein $R_4$ is lower alkyl of S-stereochemistry.

12. The method according to claim 1, wherein X is S, W is C, Z is C, $R_6$ is halogen, $R_4$ is lower alkyl of S-stereochemistry, $R_3$ is hydrogen, $R_5$ is hydrogen, and $R_1$ and $R_2$ are each hydrogen.

13. The method according to claim 1, wherein $R_3CR_4$ is cyclohexyl.

14. The method according to claim 1, wherein said subject has abnormal levels of β-amyloid.

15. The method according to claim 14, wherein said subject has elevated levels of β-amyloid.

16. The method according to claim 15, wherein said compound of formula I reduces said elevated levels of β-amyloid.

* * * * *